(12) United States Patent
Yano et al.

(10) Patent No.: US 10,842,807 B2
(45) Date of Patent: Nov. 24, 2020

(54) METHODS OF TREATING NEURODEGENERATIVE DISORDERS COMPRISING DNA METHYLTRANSFERASE INHIBITORS

(71) Applicants: Hiroko Yano, St. Louis, MO (US); Albert Kim, St. Louis, MO (US)

(72) Inventors: Hiroko Yano, St. Louis, MO (US); Albert Kim, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 16/309,796

(22) PCT Filed: Jun. 13, 2017

(86) PCT No.: PCT/US2017/037276
§ 371 (c)(1),
(2) Date: Dec. 13, 2018

(87) PCT Pub. No.: WO2017/218551
PCT Pub. Date: Dec. 12, 2017

(65) Prior Publication Data
US 2019/0307782 A1 Oct. 10, 2019

Related U.S. Application Data

(60) Provisional application No. 62/349,484, filed on Jun. 13, 2016.

(51) Int. Cl.
| | | |
|---|---|---|
| *A61K 31/706* | (2006.01) |
| *A61P 25/28* | (2006.01) |
| *A61K 9/00* | (2006.01) |
| *A61K 31/7068* | (2006.01) |
| *A61P 31/00* | (2006.01) |
| *A61P 29/00* | (2006.01) |
| *A61P 25/00* | (2006.01) |
| *A61P 35/00* | (2006.01) |

(52) U.S. Cl.
CPC .......... *A61K 31/706* (2013.01); *A61K 9/0019* (2013.01); *A61K 31/7068* (2013.01); *A61P 25/00* (2018.01); *A61P 25/28* (2018.01); *A61P 29/00* (2018.01); *A61P 31/00* (2018.01); *A61P 35/00* (2018.01)

(58) Field of Classification Search
CPC ............ A61K 31/7052; A61K 31/7056; A61K 31/706; A61K 31/7064; A61K 31/7068; A61P 25/00; A61P 25/14; A61P 25/16; A61P 35/00; A61P 35/02; A61P 35/04
See application file for complete search history.

(56) References Cited

U.S. PATENT DOCUMENTS

| | | | |
|---|---|---|---|
| 2005/0037992 A1* | 2/2005 | Lyons ................. | A61K 31/165 514/49 |
| 2008/0300205 A1* | 12/2008 | Tsai ..................... | A61K 31/164 514/44 A |
| 2014/0187430 A1 | 7/2014 | Hu | |
| 2015/0368221 A1 | 12/2015 | Holson et al. | |

FOREIGN PATENT DOCUMENTS

| | | |
|---|---|---|
| WO | 2012038417 A1 | 3/2012 |
| WO | 2017218551 A1 | 12/2017 |

OTHER PUBLICATIONS

Ferrante, R. et al "Chemotherapy for the brain . . . " J. Neuroscience, vol. 24, No. 46, pp. 10335-10342. (Year: 2004).*
Lin, R. et al "Mithramycin A inhibits DNA transferase . . . " Anti-Cancer Drugs, vol. 18, pp. 1157-1164. (Year: 2007).*
Nguyen, C. et al "Histone H3-lysine 9 methylation is associated with aberrant gene silencing . . . " Cancer Res., vol. 62, pp. 6456-6461. (Year: 2002).*
Hatters, D. et al "Protein misfolding inside cells . . . " Life, vol. 60, No. 11, pp. 724-729. (Year: 2008).*
Sontag, E. et al "Methylene blue modulates huntingtin aggregation . . . " J. Neurosci., vol. 32, No. 32, pp. 11109-11119. (Year: 2012).*
Bauer, P. et al "Harnessing chaperone-mediated autophagy . . . " Nature Biotechnol., vol. 28, No. 3, pp. 256-263. (Year: 2010).*
Mangiarini, L. et al., "Exon 1 of the HD Gene with an Expanded CAG Repeat Is Sufficient to Cause a Progressive Neurological Phenotype in Transgenic Mice," Cell, Nov. 1, 1996, pp. 493-506, vol. 87.
Mao, D. et al., "A CDC20-APC/SOX2 Signaling Axis Regulates Human Glioblastoma Stem-like Cells," Cell Reports, Jun. 23, 2015, pp. 1809-1821, vol. 11.
Martinowich, K. et al., "DNA Methylation-Related Chromatin Remodeling in Activity-Dependent Bdnf Gene Regulation," Sci., Oct. 31, 2003, pp. 890-893, vol. 302, No. 5646.
McFarland, K. et al., "Genome-Wide Histone Acetylation Is Altered in a Transgenic Mouse Model of Huntington's Disease," PLoS One, Jul. 2012, pp. 1-16, vol. 7, No. 7, e41423.
McFarland, K. et al., "Genome-Wide Increase in Histone H2A Ubiquitylation in a Mouse Model of Huntington's Disease," J. Huntington's Dis., 2013, pp. 263-277, vol. 2, No. 3.
Menalled, L. et al., "Systematic behavioral evaluation of Huntington's disease transgenic and knock-in mouse models," UKPMC Funders Group Author Manuscript, Mar. 1, 2010, pp. 1-36, published in final edited form as: Neurobiol. Dis., Sep. 2009, pp. 319-336, vol. 35, No. 3.
Mielcarek, M. et al., "HDAC4 Reduction: A Novel Therapeutic Strategy to Target Cytoplasmic Huntingtin and Ameliorate Neurodegeneration," PLoS Biol, Nov. 2013, pp. 1-16, vol. 11, No. 11, e1001717.

(Continued)

Primary Examiner — Leigh C Maier
(74) Attorney, Agent, or Firm — Polsinelli PC

(57) ABSTRACT

The present disclosure provides a method of treating a neurodegenerative disorder, the method comprising administering a DNA methyltransferase inhibitor.

11 Claims, 28 Drawing Sheets
(4 of 28 Drawing Sheet(s) Filed in Color)
Specification includes a Sequence Listing.

(56) References Cited

OTHER PUBLICATIONS

Moore, L. et al., "DNA Methylation and Its Basic Function," Neuropsychopharmacol., Rev., advance online publication, Jul. 11, 2012, pp. 1-16, published in final form as: Neuropsychopharmacol., 2013, pp. 23-38, vol. 38.

Ng C. et al., "Extensive changes in DNA methylation are associated with expression of mutant huntingtin," PNAS, Feb. 5, 2013, pp. 2354-2359, vol. 110, No. 6.

Pan, Y. et al., "Inhibition of DNA Methyltransferases Blocks Mutant Huntingtin-Induced Neurotoxicity," Scientific Reports, 2016, pp. 1-16, vol. 6, No. 31022.

Pavese, N. et al., "Progressive striatal and cortical dopamine receptor dysfunction in Huntington's disease: a PET study," Brain, 2003, pp. 1127-1135, vol. 126.

Pruunsild, P. et al., "Dissecting the human BDNF locus: bidirectional transcription, complex splicing, and multiple promoters," Genomics, 2007, pp. 397-406, vol. 90, Elsevier.

Quintas-Cardama, A. et al., "Therapy with azanucleosides for myelodysplastic syndromes," Nat. Rev. Clin. Oncol., Aug. 2010, pp. 433-444, vol. 7.

Rogstad, D. et al., "Chemical Decomposition of 5-Aza-2'-deoxycytidine (Decitabine): Kinetic Analyses and Identification of Products by NMR, HPLC, and Mass Spectrometry," Chem. Res. Toxicol., 2009, pp. 1194-1204, vol. 22, No. 6.

Rose, N. et al., "Understanding the relationship between DNA methylation and histone lysine methylation," Biochim. Biophys. Acta, 2014, pp. 1362-1372, vol. 1839.

Ross, C. et al., "Huntington disease: natural history, biomarkers and prospects for therapeutics," Nat. Rev. Neurol., 2014, pp. 204-216, vol. 10.

Ryu, H. et al., "ESET/SETDB1 gene expression and histone H3 (K9) trimethylation in Huntington's disease," PNAS, Dec. 12, 2006, pp. 19176-19181, vol. 103, No. 50.

Sadri-Vakili, G. et al., "Mechanisms of Disease: histone modifications in Huntington's disease," Nat. Clin. Pract. Neurol., Jun. 2006, pp. 330-338, vol. 2, No. 6.

Sadri-Vakili, G. et al., "Histones associated with downregulated genes are hypo-acetylated in Huntington's disease models," Hum. Mol. Genet., 2007, pp. 1293-1306, vol. 16, No. 11.

Sathasivam, K. et al., "Aberrant splicing of HTT generates the pathogenic exon 1 protein in Huntington disease," PNAS, Feb. 5, 2013, pp. 2366-2370, vol. 110, No. 6.

Seredenina, T. et al., "What have we learned from gene expression profiles in Huntington's disease?," Neurobiol. Dis., Jan. 2012, pp. 83-98, vol. 45, No. 1.

Simmons, D. et al., "A Small Molecule TrkB Ligand Reduces Motor Impairment and Neuropathology in R6/2 and BACHD Mouse Models of Huntington's Disease," J. Neurosci., Nov. 27, 2013, pp. 18712-18727, vol. 33, No. 48.

Strand, A. et al., "Expression Profiling of Huntington's Disease Models Suggests That Brain-Derived Neurotrophic Factor Depletion Plays a Major Role in Striatal Degeneration," J. Neurosci., Oct. 24, 2007, pp. 11758-11768, vol. 27, No. 43.

Stresemann, C. et al., "Modes of action of the DNA methyltransferase inhibitors azacytidine and decitabine," Int. J. Cancer, 2008, pp. 8-13, vol. 123, Wiley-Liss, Inc.

Sugars, K. et al., "Transcriptional abnormalities in Huntington disease," Trends Genet., May 2003, pp. 233-238, vol. 19, No. 5.

Tahiliani, M. et al., "Conversion of 5-Methylcytosine to 5-Hydroxymethylcytosine in Mammalian DNA by MLL Partner TET1," Sci., May 15, 2009, pp. 930-935, vol. 324, No. 5929.

Taiwo, O. et al., "Methylome analysis using MeDIP-seq with low DNA concentrations," Nat. Protoc., 2012, pp. 617-636, vol. 7, No. 4.

Tao, X. et al., "A Calcium-Responsive Transcription Factor, CaRF, that Regulates Neuronal Activity-Dependent Expression of BDNF," Neuron, Jan. 31, 2002, pp. 383-395, vol. 33.

Thomas, E., "Striatal Specificity of Gene Expression Dysregulation in Huntington's Disease," J. Neurosci. Res., Nov. 2006, pp. 1151-1164, vol. 84, No. 6.

Tognini, P. et al., "Experience-dependent DNA methylation regulates plasticity in the developing visual cortex," Nat. Neurosci., May 2015, pp. 956-958, vol. 18.

Tuesta, L. et al., "Mechanisms of epigenetic memory and addiction," EMBO J., 2014, pp. 1091-1103, vol. 33, No. 10.

Valor, L. et al., "Genomic Landscape of Transcriptional and Epigenetic Dysregulation in Early Onset Polyglutamine Disease," J. Neurosci., Jun. 19, 2013, pp. 10471-10482, vol. 33, No. 25.

Valor, L. et al., "What's wrong with epigenetics in Huntington's disease?," Neuropharmacol., 2014, 2-14, pp. 103-114, vol. 80.

Vashishtha, M. et al., "Targeting H3K4 trimethylation in Huntington disease," PNAS, Jul. 19, 2013, pp. E3027-E3036, vol. 110.

Veldic, M. et al., "DNA-methyltransferase 1 mRNA is selectively overexpressed in telencephalic GABAergic interneurons of schizophrenia brains," PNAS, Jan. 6, 2004, pp. 348-353, vol. 101, No. 1.

Walker, F., "Huntington's disease," Lancet, 2007, pp. 218-228, vol. 369.

Wang, F. et al., "Genome-wide loss of 5-hmC is a novel epigenetic feature of Huntington's disease," Hum. Mol. Genet., 2013, pp. 3641-3653, vol. 22, No. 18.

Wang, F. et al., "Epigenetic modifications as novel therapeutic targets for Huntington's disease," Epigenomics, 2014, pp. 287-297, vol. 6, No. 3.

Weeks, R. et al., "Striatal D1 and D2 Dopamine Receptor Loss in Asymptomatic Mutation Carriers of Huntington's Disease," Ann. Neurol., Jul. 1996, pp. 49-54, vol. 40, No. 1.

Wild, E. et al., "Targets for Future Clinical Trials in Huntington's Disease: What's in the Pipeline?," Movement Disorders, 2014, pp. 1434-1445, vol. 29, No. 11.

Wu, H. et al., "Mechanisms and functions of Tet protein-mediated 5-methylcytosine oxidation," Genes Dev., 2011, pp. 2436-2452, vol. 25, Cold Spring Harbor Laboratory Press.

Xie, Y. et al., "BDNF Overexpression in the Forebrain Rescues Huntington's Disease Phenotypes in YAC128 Mice," J. Neurosci., Nov. 3, 2010, pp. 14708-14718, vol. 30, No. 44.

Yano, H. et al., "Inhibition of mitochondrial protein import by mutant huntingtin," Nat. Neurosci., 2014, pp. 822-831, vol. 17.

Yoo, C. et al., "Epigenetic therapy of cancer: past, present and future," Nat. Rev. Drug Discov., Jan. 2006, pp. 37-50, vol. 5.

Zuccato, C. et al., "Loss of Huntingtin-Mediated BDNF Gene Transcription in Huntington's Disease," Sci., Jul. 20, 2001, pp. 493-498, vol. 293, No. 5529.

Zuccato, C. et al., "Role of brain-derived neurotrophic factor in Huntington's disease," Prog. Neurobiol., 2007, pp. 294-330, Vol. vol. 81.

Zuccato, C. et al., "Systematic Assessment of BDNF and Its Receptor Levels in Human Cortices Affected by Huntington's Disease," Brain Pathol., 2008, pp. 225-238, vol. 18.

Zuccato, C. et al., "Molecular Mechanisms and Potential Therapeutical Targets in Huntington's Disease," Physiol. Rev., 2010, pp. 905-981, vol. 90.

Abel, T. et al., "Epigenetic targets of HDAC inhibition in neurodegenerative and psychiatric disorders," NIH Public Access Author Manuscript, Feb. 1, 2009, pp. 1-13, published in final edited form as: Curr. Opin. Pharmacol., Feb. 2008, pp. 57-64, vol. 8, No. 1.

Aid, T. et al., "Mouse and Rat BDNF Gene Structure and Expression Revisited," J. Neurosci. Res., 2007, pp. 525-535, vol. 85, Wiley-Liss, Inc.

Bates, G., "Huntingtin aggregation and toxicity in Huntington's disease," Lancet, May 10, 2003, pp. 1642-1644, vol. 361, No. 9369.

Baydyuk, M. et al., "BDNF signaling and survival of striatal neurons," Frontiers Cell. Neurosci., Aug. 2014, pp. 1-10, vol. 8, No. 254.

Bird, A., "DNA methylation patterns and epigenetic memory," Genes Dev., 2002, pp. 6-21, vol. 16, Cold Spring Harbor Laboratory Press.

Canals, J. et al., "Brain-Derived Neurotrophic Factor Regulates the Onset and Severity of Motor Dysfunction Associated with Enkephalinergic Neuronal Degeneration in Huntington's Disease," J. Neurosci., Sep. 1, 2004, pp. 7727-7739, vol. 24, No. 35.

(56) References Cited

OTHER PUBLICATIONS

Cedar, H. et al., "Linking DNA methylation and histone modification: patterns and paradigms," Nat. Rev. Genet., May 2009, pp. 295-304, vol. 10, Macmillian Publishers Limited.
Cha, J-H. et al., "Altered brain neurotransmitter receptors in transgenic mice expressing a portion of an abnormal human Huntington disease gene," PNAS, May 1998, pp. 6480-6485, vol. 95.
Cha, J-H., "Transcriptional Signatures in Huntington's Disease," NIH Public Access Author Manuscript, Jul. 10, 2008, pp. 1-32, published in final edited form as: Prog. Neurobiol., Nov. 2007, pp. 228-248, vol. 83, No. 4.
Chabot, G. et al., "Plasma and Cerebrospinal Fluid Pharmacokinetics of 5-Aza-2'-deoxycytidine in Rabbits and Dogs," Cancer Res., Feb. 1983, pp. 592-597, vol. 43.
Chen, W. et al., "Derepression of BDNF Transcription Involves Calcium-Dependent Phosphorylation of MeCP2," Sci., Oct. 31, 2003, pp. 885-889, vol. 302, No. 5646.
Creusot, F. et al., "Inhibition of DNA Methyltransferase and Induction of Friend Erythroleukemia Cell Differentiation by 5-Azacytidine and 5-Aza-2'-deoxycytidine," J. Biol. Chem., Feb. 25, 1982, pp. 2041-2048, vol. 257, No. 4.
Crook, Z. et al., "Huntington's Disease: Can Mice Lead the Way to Treatment?," Neuron, Feb. 10, 2011, pp. 423-435, vol. 69, Elsevier Inc.
Day, J. et al., "DNA methylation and memory formation," Nat. Neurosci., Nov. 2010, pp. 1319-1323, vol. 13, No. 11.
Day, J. et al., "DNA methylation regulates associative reward learning," Nat. Neurosci., Oct. 2013, pp. 1445-1452, vol. 16, No. 10.
Difiglia, M. et al., "Aggregation of Huntingtin in Neuronal Intranuclear Inclusions and Dystrophic Neurites in Brain," Sci., Sep. 26, 1997, pp. 1990-1993, vol. 277, No. 5334.
Falkenberg, K. et al., "Histone deacetylases and their inhibitors in cancer, neurological diseases and immune disorders," Nat. Rev. Drug Discov., Sep. 2014, pp. 673-691, vol. 13.
Feng, J. et al., "Dynamic Expression of De Novo DNA Methyltransferases Dnmt3a and Dnmt3b in the Central Nervous System," J. Neurosci. Res., 2005, pp. 734-746, vol. 79.
Feng, J. et al., "Dnmt1 and Dnmt3a maintain DNA methylation and regulate synaptic function in adult forebrain neurons," Nat. Neurosci., Apr. 2010, pp. 423-430, vol. 13, No. 4.
Gambazzi, L. et al., "Diminished Activity-Dependent Brain-Derived Neurotrophic Factor Expression Underlies Cortical Neuron Microcircuit Hypoconnectivity Resulting from Exposure to Mutant Huntingtin Fragments," JPET, 2010, pp. 13-22, vol. 335, No. 1.
Gavin, D. et al., "Histone modifications, DNA methylation, and Schizophrenia," NIH Public Access Author Manuscript, May 1, 2011, pp. 1-15, published in final edited form as: Neurosci. Biobehav. Rev., May 2010, pp. 882-888, vol. 34, No. 6.
Glajch, K. et al., "Epigenetic Mechanisms Involved in Huntington's Disease Pathogenesis," J. Huntingtons Dis., 2015, pp. 1-15, vol. 4, No. 1, IOS Press.
Gnyszka, A. et al., "DNA Methyltransferase Inhibitors and Their Emerging Role in Epigenetic Therapy of Cancer," Anticancer Res., 2013, pp. 2989-2996, vol. 33.
Gorbunova, V. et al., "Genome-wide demethylation destabilizes CTG-CAG trinucleotide repeats in mammalian cells," Hum. Mol. Genet., 2004, pp. 2979-2989, vol. 13, No. 23.
Gray, M. et al., "Full-Length Human Mutant Huntingtin with a Stable Polyglutamine Repeat Can Elicit Progressive and Selective Neuropathogenesis in BACHD Mice," J. Neurosci., Jun. 11, 2008, pp. 6182-6195, vol. 28, No. 24.
Grayson, D. et al., "The Dynamics of DNA Methylation in Schizophrenia and Related Psychiatric Disorders," Neuropsychopharmacol. Rev., Sep. 5, 2012, advance online publication, pp. 1-29, final published form as: Neuropscholpharmacol., 2013, pp. 138-166, vol. 38.
Greenberg, M. et al., "New Insights in the Biology of BDNF Synthesis and Release: Implications in CNS Function," J. Neurosci., Oct. 14, 2009, pp. 12764-12767, vol. 29, No. 41.

Guo, J. et al., "Hydroxylation of 5-Methylcytosine by TET1 Promotes Active DNA Demethylation in the Adult Brain," Cell, Apr. 29, 2011, pp. 423-434, vol. 145, Elsevier Inc.
Heyward, F. et al., "DNA Methylation in Memory Formation: Emerging Insights," Neuroscientist, 2015, pp. 475-489, vol. 21, No. 5.
Hodges, A. et al., "Regional and cellular gene expression changes in human Huntington's disease brain," Hum. Mol. Genet., 2006, pp. 965-977, vol. 15, No. 6.
Inano, K. et al., "Maintenance-Type DNA Methyltransferase is Highly Expressed in Post-Mitotic Neurons and Localized in the Cytoplasmic Compartment," J. Biochem., 2000, pp. 315-321, vol. 128.
International Search Report and Written Opinion dated Aug. 16, 2017 from related Patent Application No. PCT/US2017/037276; 9 pgs.
Jakovcevski, M. et al., "Epigenetic mechanisms in neurodevelopmental and neurodegenerative disease," NIH Public Access Author Manuscript, Aug. 1, 2013, pp. 1-27, published in final edited form as: Nat. Med., Aug. 2012, pp. 1194-1204, vol. 18, No. 8.
Jiang, M. et al., "Small-molecule TrkB receptor agonists improve motor function and extend survival in a mouse model of Huntington's disease," Hum. Mol. Genet., 2013, pp. 2462-2470, vol. 22, No. 12.
Kaas, G. et al., "TET1 Controls CNS 5-Methylcytosine Hydroxylation, Active DNA Demethylation, Gene Transcription, and Memory Formation," Neuron, Sep. 18, 2013, pp. 1086-1093, vol. 79, Elsevier Inc.
Karahoca, M. et al., "Pharmacokinetic and pharmacodynamic analysis of 5-aza-2'-deoxycytidine (decitabine) in the design of its dose-schedule for cancer therapy," Clin. Epigenetics, 2013, pp. 1-16, vol. 5, No. 3.
Kelly, T. et al., "Epigenetic Modifications as Therapeutic Targets," HHS Public Access Author Manuscript, Apr. 1, 2012, pp. 1-22, published in final edited form as: Nat. Biotechnol., Oct. 2010, pp. 1069-1078, vol. 28, No. 10.
Kim, M-O. et al., "Altered Histone Monoubiquitylation Mediated by Mutant Huntingtin Induces Transcriptional Dysregulation," J. Neurosci., Apr. 9, 2008, pp. 3947-3957, vol. 28, No. 15.
Kriaucionis, S. et al., "The Nuclear DNA Base 5-Hydroxymethylcytosine Is Present in Purkinje Neurons and the Brain," Sci., May 15, 2009, pp. 929-930, vol. 324, No. 5929.
Landles, C. et al., "Proteolysis of Mutant Huntingtin Produces an Exon 1 Fragment That Accumulates as an Aggregated Protein in Neuronal Nuclei in Huntington Disease," J. Biol. Chem., Mar. 19, 2010, pp. 8808-8823, vol. 285, No. 12.
Lardenoije, R. et al., "The epigenetics of aging and neurodegeneration," Prog. Neurobiol., Aug. 2015, pp. 21-64, vol. 131.
Lee, J. et al., "Epigenetic Mechanisms of Neurodegeneration in Huntington's Disease," Neurotherapeutics, 2013, pp. 664-676, vol. 10, Springer.
Li, H. et al., "Amino-terminal fragments of mutant huntingtin show selective accumulation in striatal neurons and synaptic toxicity," Nat. Genet., Aug. 2000, pp. 385-389, vol. 25.
Li, S-H. et al., "Interaction of Huntington Disease Protein with Transcriptional Activator Sp1," Mol. Cell. Biol., Mar. 2002, pp. 1277-1287, vol. 22, No. 5.
Li, D. et al., "Combining MeDIP-seq and MRE-seq to investigate genome-wide CpG methylation," Methods, 2015, pp. 29-40, vol. 72.
Lu, H. et al., "DNA methylation, a hand behind neurodegenerative diseases," Front. Aging Neurosci., Dec. 2013, pp. 1-16, vol. 5, No. 85.
Lunkes, A. et al., "Proteases Acting on Mutant Huntingtin Generate Cleaved Products that Differentially Build Up Cytoplasmic and Nuclear Inclusions," Mol. Cell, Aug. 2002, pp. 259-269, vol. 10.
Luthi-Carter, R. et al., "Decreased expression of striatal signaling genes in a mouse model of Huntington's disease," Hum. Mol. Genet., 2000, pp. 1259-1271, vol. 9, No. 9, Ocford University Press.
Luthi-Carter, R. et al., "Dysregulation of gene expression in the R6/2 model of polyglutamine disease: parallel changes in muscle and brain," Hum. Mol. Genet., 2002, pp. 1911-1926, vol. 11, No. 17, Oxford University Press.

(56) References Cited

OTHER PUBLICATIONS

MacDonald, M. et al., "A Novel Gene Containing a Trinucleotide Repeat That Is Expanded and Unstable on Huntington's Disease Chromosomes," Cell, Mar. 26, 1993, pp. 971-983, vol. 72, No. 6.

* cited by examiner

FIG. 3A  FIG. 3B

METHODS OF TREATING NEURODEGENERATIVE DISORDERS COMPRISING DNA METHYLTRANSFERASE INHIBITORS

CROSS REFERENCE TO RELATED APPLICATIONS

This application claims the benefit of of PCT Application PCT/US2017/37276, filed Jun. 13, 2017, which claims priority from U.S. Provisional Application No. 62/349,484, filed Jun. 13, 2016, the disclosures of which are hereby incorporated by reference in their entirety.

GOVERNMENTAL RIGHTS

This invention was made with government support under AG033724 awarded by the National Institutes of Health. The government has certain rights in the invention.

FIELD OF THE INVENTION

The present invention encompasses compositions and methods of treatment for neurodegenerative disorders.

BACKGROUND OF THE INVENTION

Neurodegenerative disorders are a collection of conditions which primarily affect the neurons in the human brain. These disorders are characterized by a progressive loss of structure or function of neurons, including death of neurons. Many neurodegenerative disorders, including amyotrophic lateral sclerosis, Parkinson's, Alzheimer's, and Huntington's occur as a result of neurodegenerative processes.

Huntington's disease (HD) in particular is a progressive and invariably fatal, autosomal-dominant neurodegenerative disorder characterized by progressive loss of selective neurons in the striatum and cortex, leading to movement, cognitive, and psychiatric disorders. HD is caused by an abnormal expansion of polyglutamine repeats in the huntingtin (Htt) protein. Formation of Htt aggregates is a hallmark of HD. How the toxic mutant protein drives neuronal dysfunction and death remains poorly understood, and no curative treatment exists for this disease. There is need in the art for better understanding and treatment of HD.

SUMMARY OF THE INVENTION

In one aspect the disclosure provides a method to reduce symptoms associated with neurodegenerative disorder in a subject, by administering a DNA methylation inhibitor to the subject. The neurodegenerative disorder treated may be HD. The DNA methylation inhibitor may be nucleoside analog DNA methyltransferase (DNMT) inhibitor. The DNA methylation inhibitor may be administered by the intracerebroventricular (icv) route.

In an aspect the disclosure provides a method to reduce mutant Htt-induced neurotoxicity, by contacting a nucleoside analog DNMT inhibitor to a neuronal cell. The DNMT inhibitor may be decitabine or FdCyd. The DNMT inhibitor may decrease the levels of mutant Htt aggregates.

In an aspect the disclosure provides a method of preventing the development of the symptoms associated with neurodegenerative disorder in a subject, the method comprising administering to the subject at risk of developing the neurodegenerative disorder with a DNA methylation inhibitor. The neurodegenerative disorder may be HD, and the subject may be at risk of developing HD. The DNMT inhibitor may be decitabine or FdCyd. The DNMT inhibitor may decrease the levels of mutant Htt aggregates.

BRIEF DESCRIPTION OF THE FIGURES

The application file contains at least one drawing executed in color. Copies of this patent application publication with color drawing(s) will be provided by the Office upon request and payment of the necessary fee.

FIG. 1A illustrates the schematic of epigenetic drug library screen using a primary neuron model. FIG. 1B depicts DIV 5 cortical neurons transduced with Htt-expressing lentivirus were treated with decitabine or DMSO (=0 μM), and subjected to MTS assay at DIV 14. Decitabine increased the viability of Htt-72Q-expressing neurons (ANOVA, *P<0.0001 vs. Htt-25Q (0 μM), # P<0.0001 vs. Htt-72Q (0 μM), n=18). FIG. 1C depicts the chemical structure of decitabine. FIG. 1D depicts cortical neurons were fixed at DIV14 and subjected to NF immunofluorescence. Immunofluorescence intensity was quantified. Decitabine blocked Htt-72Q-induced neurite degeneration (ANOVA, *P<0.0001 vs. Htt-25Q (0 μM), # P<0.0001 vs. Htt-72Q (0 μM), n=11-24). FIG. 1E depicts representative NF immunofluorescence images of transduced neurons treated with decitabine (0.2 μM) or vehicle. Bar, 100 μm. FIG. 1F and FIG. 1G depicts cortical neurons that were subjected to nuclear staining (Hoechst 33342). Cell death was assessed by nuclear morphology. Decitabine blocked Htt-72Q induced cell death (ANOVA, *P<0.0001 vs. Htt-25Q, # P<0.0001 vs. Htt-72Q (0 μM), n=16). Representative nuclear images of transduced neurons. Arrows show examples of condensed or fragmented nuclei, indicating dead cells. Bar, 50 μm. FIG. 1H-J illustrate results with FdCyd. FIG. 1G illustrates cortical neurons transduced were treated with FdCyd and subjected to MTS assay. FIG. 1J. illustrates cortical neurons transduced were treated with FdCyd and subjected to NF immunofluorescence at DIV 14. FIG. 1I illustrates the chemical structure of FdCyd. FdCyd increased the viability of Htt-72Q-expressing neurons (ANOVA, *P<0.0001 vs. Htt-72Q (0 μM), n=11-24). FdCyd protected neurons from Htt-72Q-induced neurite degeneration (ANOVA, *P<0.0001 vs. Htt-72Q (0 μM); n=12-24). FIG. 1K-L illustrate DIV 4 striatal neurons were transduced and treated with the indicated DNMT inhibitor. FIG. 1K illustrates treatment with decitabine, and FIG. 1L illustrates treatment with FdCyd. Seven days later, neurons were fixed and subjected to NF immunofluorescence. Decitabine and FdCyd protected neurons from mutant Htt-induced neurite degeneration (ANOVA, *P<0.0001 vs. Htt-25Q (0 μM), # P<0.0001 vs. Htt-72Q (0 μM), n=13-17; *P=0.0002 and # P=0.003 vs. Htt-72Q (0 μM), n=9-16). Data are presented as mean+SEM.

FIG. 2A illustrates DIV 5 cortical neurons were transduced with two Dnmt3a shRNAs (1 and 2) or control luciferase (Luci) lentivirus; 5 days later, cell lysates were subjected to immunoblotting using indicated antibodies. FIG. 2B illustrates cortical neurons transduced with two Dnmt1 shRNAs (1 and 2) or control LacZ lentivirus and subjected to immunoblotting. FIG. 2C illustrates DIV 5 cortical neurons co-transduced with Htt-expressing lentivirus along with Dnmt3a or control shRNA lentivirus and subjected to MTS assay at DIV14.

Knockdown of DNMT3A in mutant Htt-expressing neurons was neuroprotective (ANOVA, *P<0.0001 compared to Htt-72Q plus control RNAi, n=17-20 wells per group, 5 independent experiments). FIG. 2D illustrates Cortical neurons co-transduced with Htt lentivirus and Dnmt1 or control shRNA lentivirus and subjected to MTS assay. Knockdown of DNMT1 in mutant Htt-expressing neurons was neuroprotective (ANOVA, *P<0.0001 and # P=0.0001 compared to Htt-72Q plus control RNAi, n=11-15 wells per group, 4 independent experiments). Data are presented as mean+ SEM in FIG. 2C and FIG. 2D.

FIG. 3A-3I illustrate inhibition of DNMTs restored the expression of Bdnf exon IV and VI transcripts in primary cortical neurons. FIG. 3A shows results of DIV 5 cortical neurons infected with Htt lentivirus. RNA was harvested 5 days later and subjected to qRT-PCR for total Bdnf (coding exon IX) using β-actin and 18S rRNA as reference genes. Htt-72Q decreased the expression of total Bdnf transcripts (Mann-Whitney U test, *P=0.008 vs. Htt-25Q, n=5). FIG. 3B shows a graph of the result of cortical neurons transduced and cultured with recombinant BDNF (50 ng/ml) and subjected to MTS assay at DIV 14. BDNF increased the viability of Htt-72Q-expressing neurons (ANOVA, *P<0.0001 vs. Htt-72Q with vehicle, n=9-15). FIG. 3C depicts the schematic of the mouse Bdnf locus and the relative RNA levels of the Bdnf exons. White boxes, non-coding exons; gray box, coding exon. qRT-PCR was performed as in using exon-specific Bdnf primers. Htt-72Q decreased the expression of exon IV and VI transcripts (Mann-Whitney U test, *P=0.008 vs. Htt-25Q, n=5). FIG. 3D-F show results of cortical neurons transduced with Htt lentivirus treated with indicated DNMT inhibitor or vehicle and processed. Both decitabine and FdCyd increased the expression of Bdnf exon IV, VI, and IX transcripts in Htt-72Q-expressing neurons (ANOVA, *P<0.005 vs. Htt-72Q plus vehicle, n=5-7 (D); *P<0.05 vs. Htt-72Q plus vehicle, n=5 (FIG. 3E); *P<0.05 vs. Htt-72Q plus vehicle, n=7 (FIG. 3F)). (FIG. 3G, FIG. 3H) Cortical neurons were co-transduced with lenti viruses expressing Htt and indicated shRNA and processed as in (FIG. 3C). Knockdown of DNMT3A or DNMT1 restored the expression of Bdnf exon IV and VI (ANOVA, *P<0.05 vs. Htt-72Q plus vehicle, n=4 (FIG. 3G); *P<0.01 vs. Htt-72Q plus vehicle, n=4 (FIG. 3H)). (FIG. 3I) Primary cortical neurons from BACHD mice were treated with decitabine (0.2 µM) or vehicle for 3.5 days. qRT-PCR was performed using β-actin as a reference gene. Decitabine increased expression of Bdnf exon IV, exon VI, and IX transcripts (unpaired t-test, *P<0.0001 and # P=0.0012 vs. vehicle treated). Data are presented as mean+SEM.

(FIG. 4A) Schematic of the mouse Bdnf exon IV regulatory region near the TSS. The positions of CpG sites are indicated relative to the TSS. (FIG. 4B) DIV 5 primary cortical neurons were infected with lentivirus expressing Htt-25Q or Htt-72Q exon 1 fragment; 5 days later, genomic DNA was purified and subjected to bisulfite sequencing analysis. The data show percentage of cytosine residues that were methylated in Htt25Q- and Htt-72Q-expressing neurons. Increased DNA methylation was found in mutant Htt-expressing neurons compared to WT Htt-expressing neurons. 28-30 clones from 7 independent experiments were analyzed (See FIG. 11A) for the bisulfite sequencing data from each clone). The number above the black bar (Htt-72Q) represents the fold changes in methylated cytosine relative to the white bar (Htt-25Q) at the indicated position. (FIG. 4C) Genomic DNA was purified from primary cortical neurons transduced as in (B) and subjected to MeDIP with anti-5-mC antibody followed by qPCR. The levels of 5-mC in the exon IV promoter region was higher in Htt-72Q-expressing neurons compared to that in Htt-25Q neurons (Mann-Whitney U test, *P<0.05, n=6). (FIG. 4D) Cortical neurons were transduced as in (FIG. 4B) and 5 days later were subjected to ChIP with anti-H3K4me3 antibody. H3K4me3 levels in the exon IV promoter region were lower in Htt-72Q-expressing neurons compared to Htt-25Q neurons. (unpaired t-test, *P<0.05, n=5). (FIG. 4E, FIG. 4F) Cortical neurons were processed and subjected to MeDIP as in (FIG. 4C) using Htt-72Q-expressing neurons treated with DNMT inhibitors (0.2 µM) or DMSO. Treatment with decitabine or FdCyd decreased levels of 5-mC in Bdnf promoter IV region (Mann-Whitney U test, *P=0.002, n=6 (FIG. 4E); *P=0.008, n=5 (FIG. 4F)). (FIG. 4G, FIG. 4H) Cortical neurons co-transduced with lentiviruses expressing Htt-72Q and indicated shRNA were processed as in (FIG. 4C) for MeDIP. Knockdown of DNMT3A or DNMT1 could decrease the levels of Bdnf promoter IV methylation (ANOVA, *P<0.05 vs. Htt-72Q plus vehicle, n=6). Data are presented as mean+SEM in (FIG. 4C-FIG. 4H).

(FIG. 5A) DIV 5 mouse primary striatal neurons were infected with lentivirus expressing Htt-25Q or Htt-72Q exon1 fragment; 5 days later, RNA was prepared and subjected to qRT-PCR analysis. β-actin and Hprt were used as reference genes. Decitabine restored the expression of downregulated genes in mutant Htt-expressing striatal neurons (ANOVA, *P<0.05, n=3 compared to Htt-72Q plus vehicle. Similar results were observed when Htt-72Q-expressing neurons were treated with FdCyd (data not shown). Data are presented as mean+SEM. (FIG. 5B) Procedure for the treatment of mice with FdCyd. A mini-osmotic pump containing FdCyd (0.1 mM in saline) was implanted subcutaneously on the back of mice at 6 weeks of age, and the drug was infused into the right ventricle through a stereotactically placed catheter. One week later, the striatum was dissected for qRT-PCR analysis. ICV, intracerebroventricular. (FIG. 5C-F) FdCyd was delivered into R6/2 or WT mouse brain by icv infusion at 6 weeks of age. Saline was used as control. One week after drug infusion was initiated; RNA was extracted from the striatum and subjected to qRT-PCR analysis. β-actin was used as a reference gene. Levels of Drd2 (FIG. 5C), Ppp1r1b (FIG. 5D), Rasd2 (FIG. 5E), and Adora2a (FIG. 5F) mRNA were restored in R6/2 mice after FdCyd treatment. FdCyd treatment showed a trend towards increasing Penk RNA in R6/2 striatum. (ANOVA, *P<0.005 compared to WT-saline, # P<0.05 compared to R6/2-saline, n=7-9 mice per group). The vertical bars represent the range of values.

(FIG. 7A) Tenovin-1 (p53 activator), one of the top three positive compounds from the cell-based screen (FIG. 1A), was subjected to cell viability assay using MTS.

Treatments with tenovin-1 did not significantly increase the viability of mutant Htt-expressing neurons (ANOVA, *P<0.0001 compared to Htt-25Q (0 µM); P=0.591, Htt-72Q (0.02 µM) vs Htt-72Q (0 µM); P=0.355, Htt-72Q (0.2 µM) vs. Htt-72Q (0 µM); P=0.168, Htt-72Q (2 µM) vs Htt-72Q (0 µM); n=6-12 wells per group). (FIG. 7B) AG-014699 (PARP1 inhibitor), another screen hit, was subjected to cell viability assay as in (FIG. 7A). There is no significant difference in survival between the AG-014699- and vehicle-treated Htt-72Q neurons (ANOVA,*P<0.0001 compared to Htt-25Q (0 µM); P=0.142, Htt-72Q (0.02 µM) vs Htt-72Q (0 µM); P=0.254, Htt-72Q (0.2 µM) vs Htt-72Q (0 µM); P=0.781, Htt-72Q (2 µM) vs Htt-72Q (0 µM); n=12 wells per groups). Data are presented as mean+SEM.

(FIG. 8A) DIV 5 mouse primary cortical neurons were infected with Htt-72Q lentivirus and treated with decitabine or vehicle (DMSO). RNA was prepared at DIV 10 and subjected to qRT-PCR analysis for Htt-72Q (human). β-actin and Hprt were used as reference genes. Decitabine did not decrease the levels of Htt-72Q mRNA compared to vehicle (ANOVA, n=6 independent experiments). (FIG. 8B) DIV 5cortical neurons were infected with Htt lentivirus and treated with decitabine (0.2 µM) or DMSO. Neurons were fixed at DIV 11-12 and subjected to indirect immunofluorescence with a specific mouse monoclonal Htt antibody EM48, which preferentially detects aggregated mutant protein. Nuclei were labeled with Hoechst 33342. Images were captured using an Operetta high-content imaging system (PerkinElmer) with a 20× objective lens. Bar 100 µm. (FIG. 8C) EM48 immunofluorescence intensity in (FIG. 8B) was quantified using an ImageJ-based macro. Decitabine significantly decreased the levels of mutant Htt aggregates in Htt-72Q-expressing primary cortical neurons (ANOVA, *P<0.0001 vs. Htt-72Q-DMSO, n=18 wells from 6 independent experiments). (FIG. 8D) Cortical neurons transduced and processed as in (FIG. 8A) were directly harvested in SDS sample buffer at DIV 10 and subjected to immunoblotting with anti-Htt EM48 monoclonal antibody. Blot was reprobed with anti-β-actin antibody. Representative immunoblot from 3 independent experiments is shown. Decitabine could decrease the levels of aggregated high molecular weight mutant Htt in a stacking gel (*). Data in (FIG. 8A) and (FIG. 8C) are presented as mean+SEM.

(FIG. 9A) DIV 5 cortical neurons transduced with lentivirus expressing Htt-72Q or Htt-25Qfragment were treated with the indicated drugs or DMSO (=0 µM) and subjected to MTS assay at DIV 14. Decitabine, but not zebularine, increased the viability of mutant Htt-expressing neurons (ANOVA, *P<0.0001 compared to Htt-72Q (0 µM); no significant difference in survival between zebularine and vehicle-treated Htt-72Q neurons; n=8-18 wells per group, 3 independent experiments). FIG. 9B illustrates the chemical structure of zebularine. (FIG. 9C) Primary cortical neurons transduced and treated with 5-azacytidinewere subjected to MTS assay as in (A). There was no significant difference in survival between 5-azacytidine- and vehicle-treated Htt-72Q neurons (ANOVA, n=6-15 wells per group, 3 independent experiments). (FIG. 9D) Primary cortical neurons were transduced and treated as in (FIG. 9A) and subjected to neurofilament (NF) immunofluorescence. There was no significant difference in NF immunofluorescence intensity between 5-azacytidine- and vehicle-treated Htt-72Q cortical neurons (ANOVA, n=6-15 wells per group, 3 independent experiments)(D) Primary striatal neurons transduced with Htt-25Q or Htt-72Q lentivirus at DIV 4 were treated with 5-azacytidineor DMSO. Seven days later, neurons were subjected to NF immunofluorescence. There was no significant difference in NF immunofluorescence intensity between 5-azacytidine- and vehicle-treated Htt-72Q striatal neurons (ANOVA, n=9-17 wells, 3 independent experiments). Data are presented as mean+SEM. FIG. 9F illustrates the chemical structure of Azacytidine.

(FIG. 10A) DIV 5 cortical neurons were transduced with lentivirus expressing Dnmt3ashRNA (shDnmt3a-1 or -2) or control shRNA along with Htt-72Q virus; 5 days later, RNA was prepared and subjected to qRT-PCR analysis. Dnmt3aRNAi did not significantly reduce the levels of Dnmt1mRNA in mutant Htt-expressing neurons, showing the specificity of these shRNAs (ANOVA, n=3 independent experiments). (FIG. 10B) Cortical neurons were transduced with lentivirus expressing Dnmt1shRNA (shDnmt1-1 or -2) or control shRNA along with Htt-72Q virus and processed as in (A). Dnmt1RNAi did not decrease the levels of Dnmt3amRNA in mutant Htt-expressing neurons, showing the specificity of these shRNAs (ANOVA, n=3 independent experiments). Data are presented as mean+SEM.

(FIG. 11A) Primary cortical neurons were transduced with Htt-25Q or Htt-72Qat DIV5. Five days later, genomic DNA was prepared and subjected to bisulfite DNA sequencing analysis on the 13 CpG sites in the regulatory region of Bdnfexon IV. The positions of CpG sites are indicated relative to the TSS. Data are pooled from 7 independent experiments. Percentage of methylated cytosine residues was calculated and presented in FIG. 4B. (FIG. 11B) Primary cortical neurons were transduced and processed for bisulfite DNA sequencing analysis on the 17 CpG sites in the regulatory region of Bdnf exon VI as in (FIG. 11A). Data are pooled from 3 independent experiments. The CpG sites in this region were mostly unmethylated in Htt-25Q- and Htt-72Q-expressing neurons.

(FIG. 12A) Decitabine (0.2 mM in saline) was first incubated at 37° C. for indicated number of days in vitro and then added to the culture media at a final concentration 0.2 µM of DIV 5 primary neurons transduced with Htt-25Q or Htt-72Q lentivirus. The neuroprotective activity of decitabine was tested using MTS assay at DIV 14. Decitabine lost its activity when tested after 11 days of incubation (ANOVA, *P<0.0001 compared to Htt-72Q plus vehicle, no difference between Htt-72Q plus vehicle vs. Htt-72Q plus decitabine preincubated for 11 days, n=9 wells, 3 independent experiments). (FIG. 12B) Similar experiments were performed with FdCyd as in (FIG. 12A). In contrast to decitabine, FdCyd preincubated for 11 or 45 days showed neuroprotective effects comparable to FdCyd with no preincubation (ANOVA, *P<0.0001 compared to Htt-72Q plus vehicle, n=9 wells, 3 independent experiments). Data are presented as mean+SEM.

DETAILED DESCRIPTION OF THE INVENTION

The disclosure encompasses methods to treat neurodegenerative disorders in a subject by administering DNA methylation inhibitors. In particular, the disclosure provides methods of use for nucleoside analog DNA methyltransferase inhibitors to reduce the symptoms of and/or treat neurodegenerative disorder such as Huntington's disease (HD).

Various aspects of the invention are described in further detail in the following subsections.

I. Composition

In one aspect the disclosure encompasses a composition comprising a DNA methyltransferase inhibitor. DNA methyltransferase inhibitors inhibit DNA methylation as catalyzed by a DNA methyltransferase. The term DNA methylation as used herein refers to the addition of a methyl group to the cytosine of a nucleotide. DNA methylation is catalyzed by members of the DNA methyltransferase (DNMT) family of enzymes, including DNMT1, DNMT3A, and DNMT3B.

Non-limiting examples of suitable DNA methyltransferase inhibitors may include decitabine, 5-fluoro-2'-deoxycytidine (FdCyd), azacitidine (also known as Vidaza™), zebularine, caffeic acid, chlorogenic acid, epigallocatechin gallate, hydralazine hydrochloride, procainamide hydrochloride, procaine hydrochloride, and N-phthalyl-L-tryptophan. In some embodiments, DNA methyltransferase inhibitors of the present disclosure may be nucleoside analog inhibitors. For instance, DNA methyltransferase inhibitors of the invention may be decitabine, FdCyd, azacitidine (also known as Vidaza™), or zebularine.

Figure 1A:
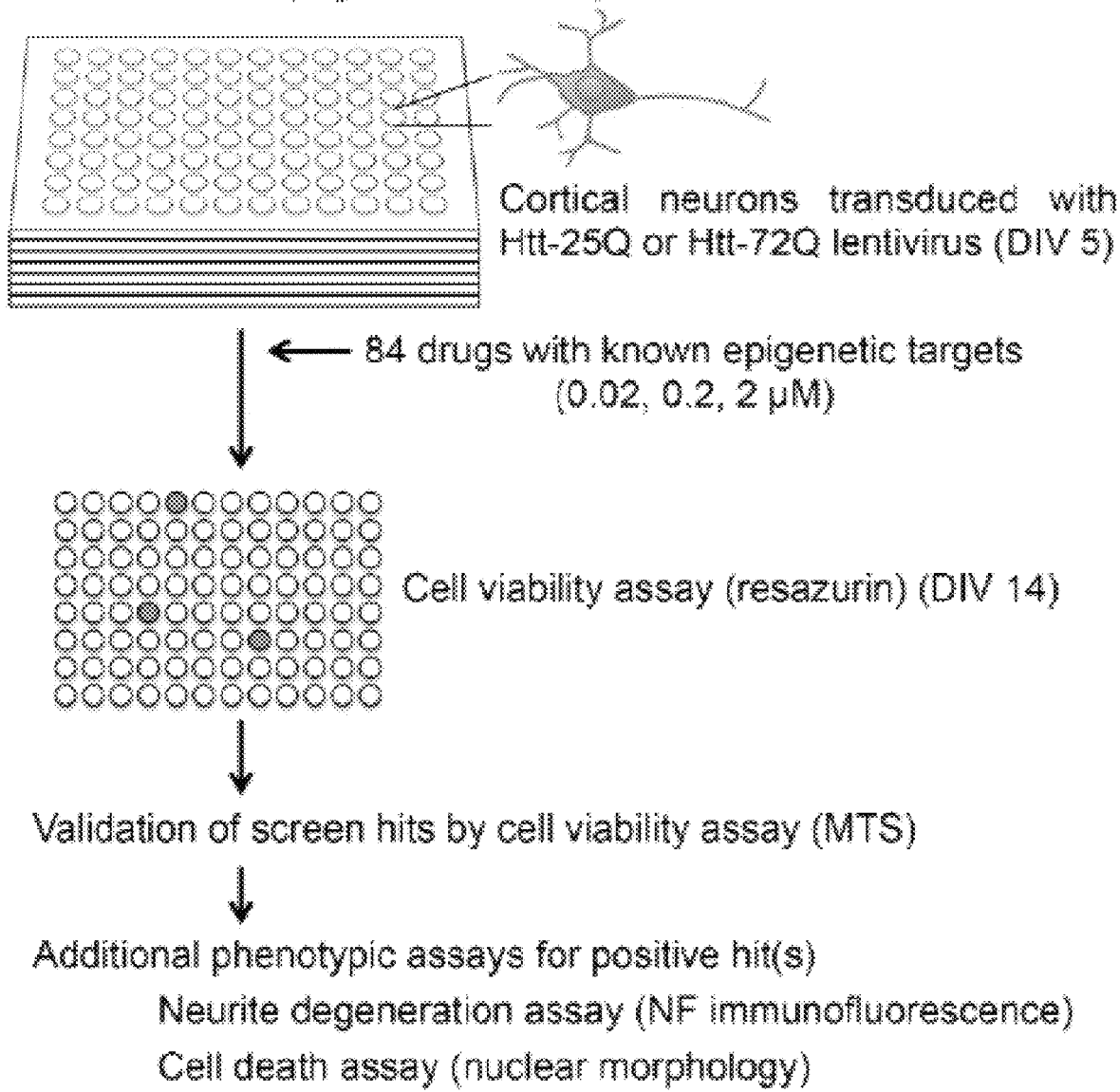
FIG. 1A-1L illustrate that DNMT inhibitors, decitabine and FdCyd, protect neurons from mutant Htt-induced toxicity in culture.
Figure 1B:
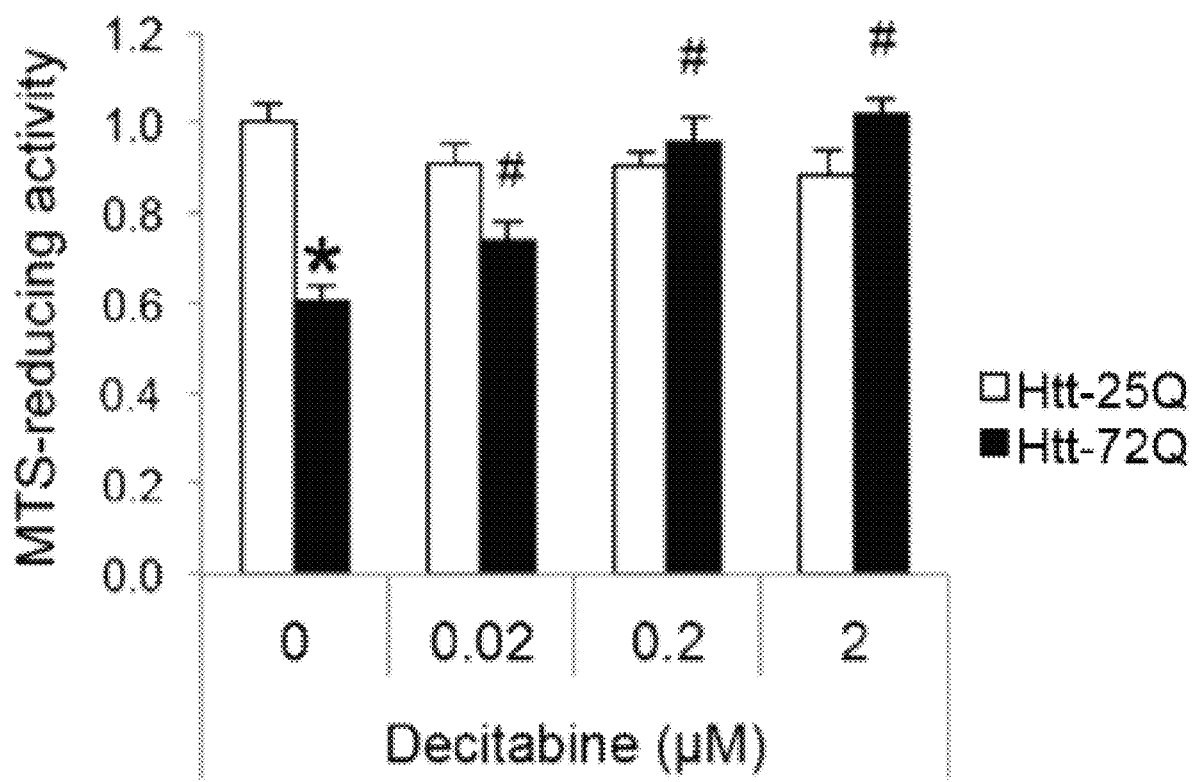
Figure 1C:
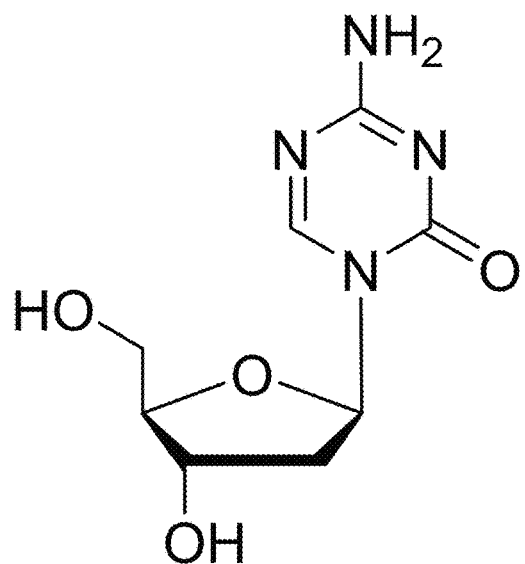

In an aspect, a DNA methylation inhibitor of a composition of the present disclosure is decitabine (FIG. 1C). A composition of the invention may comprise decitabine at a concentration of about 0.02 µM to about 20 µM. In various aspects, a composition of the invention may comprise decitabine at a concentration from about 0.01 µM to about 0.05 µM, about 0.04 µM to about 1 µM, from about 0.8 µM to about 3 µM, from about 1 uM to about 10 µM, from about 5 µM to about 15 µM, or from about 10 µM to about 25 µM. Preferably the composition of the invention may comprise decitabine at a concentration of 0.2 µM to 2 µM.

Figure 1D:
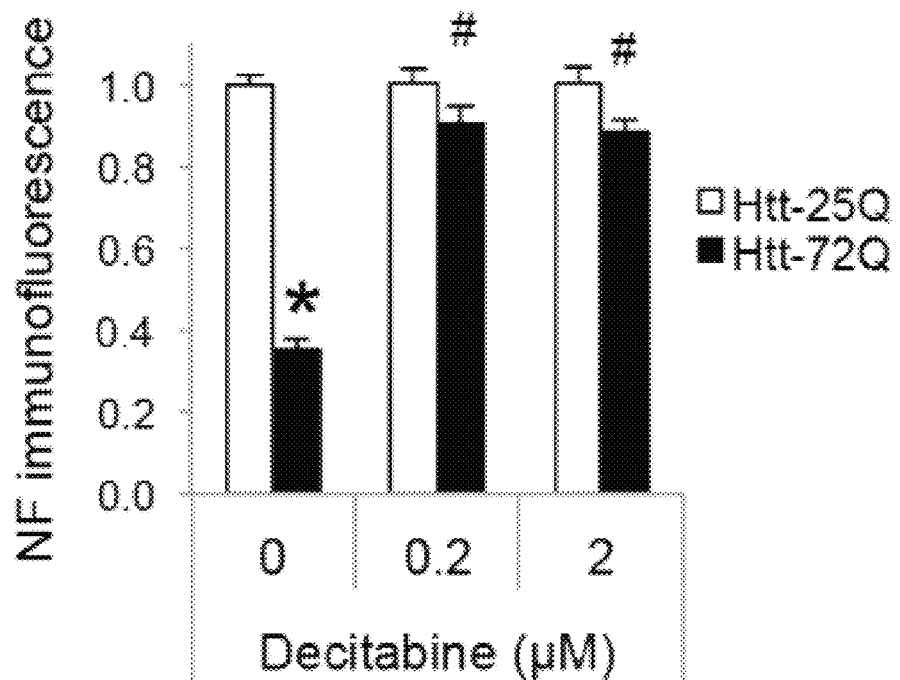
Figure 1E:
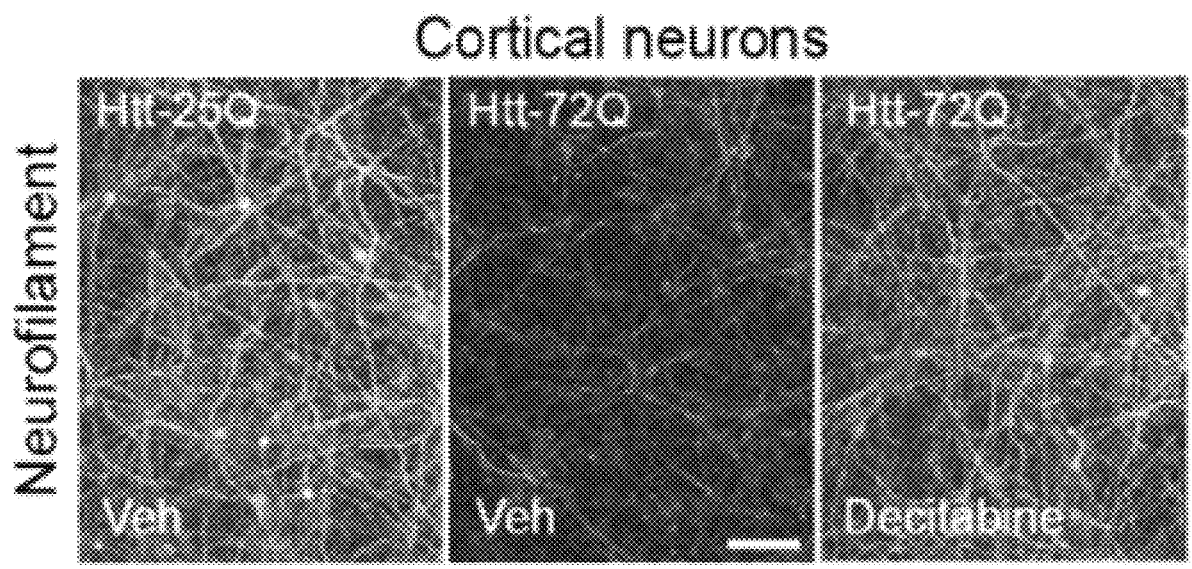
Figure 1F:
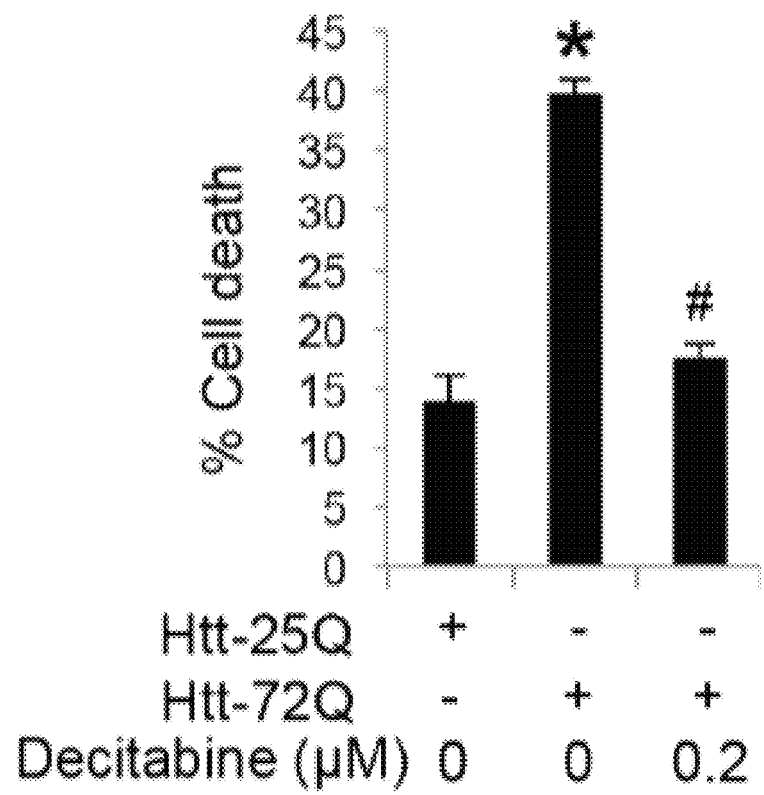
Figure 1G:
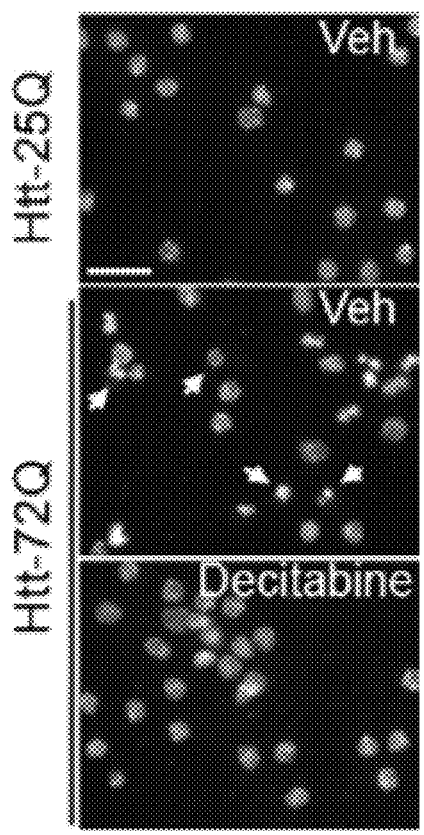
Figure 1H:
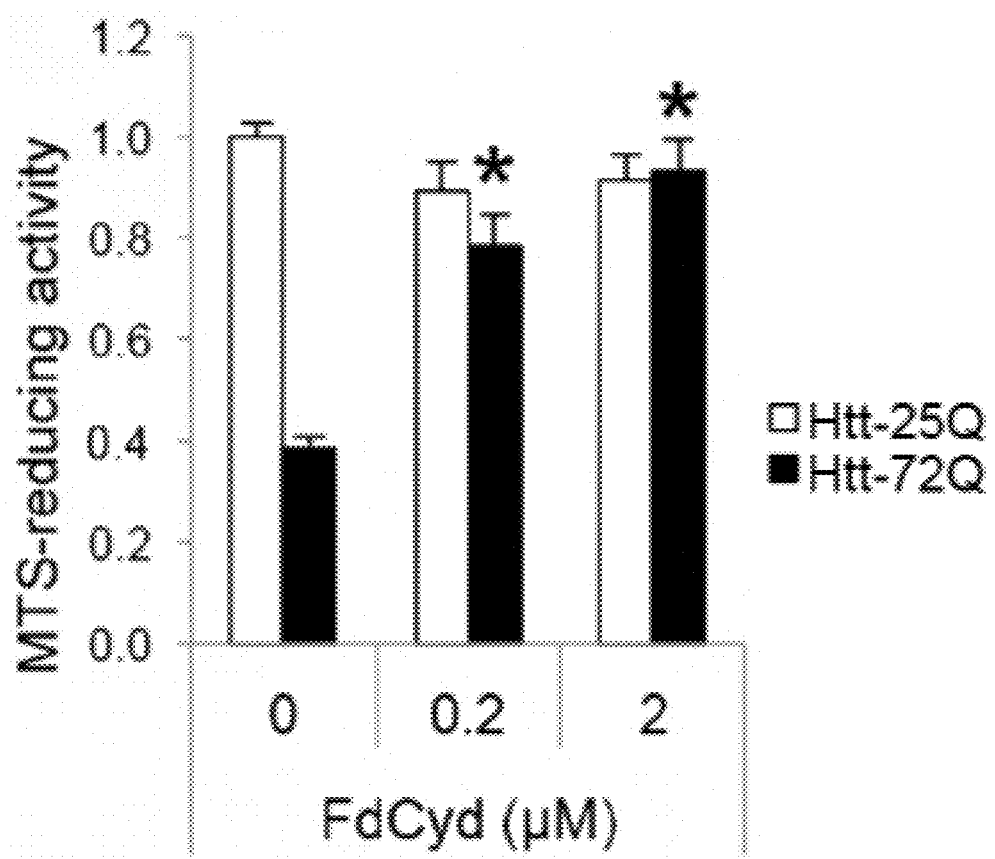
Figure 1I:
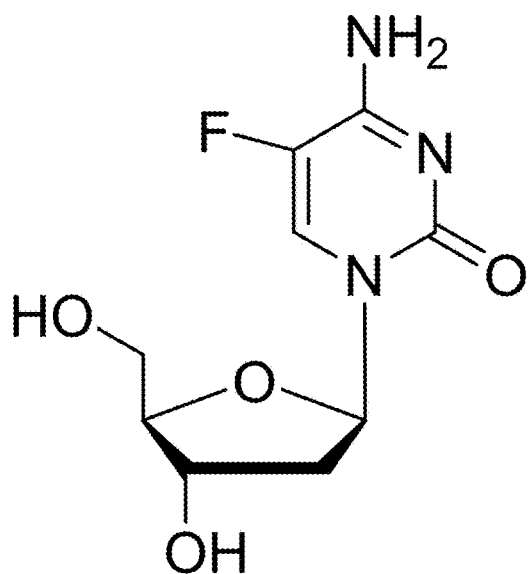
Figure 1J:
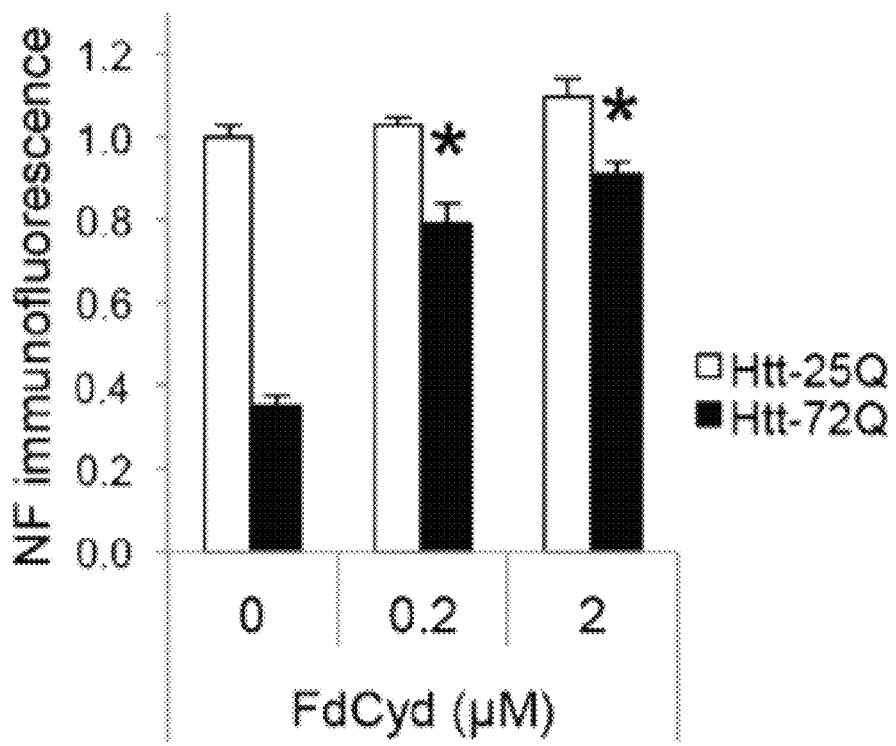

In another aspect, a DNA methylation inhibitor of a composition of the present disclosure is FdCyd (FIG. 1I). A composition of the invention may comprise FdCyd at a concentration of about 0.02 uM to about 20 uM. In various aspects, a composition of the invention may comprise FdCyd a concentration from about 0.01 µM to about 0.05 µM, about 0.04 µM to about 1 µM, from about 0.8 µM to about 3 µM, from about 1 uM to about 10 µM, from about 5 µM to about 15 µM, or from about 10 µM to about 25 µM. Preferably the composition of the invention may comprise FdCyd at a concentration of 0.2 µM to 2 µM.

In another aspect, a DNA methylation inhibitor of a composition of the present disclosure is azacitidine. A composition of the invention may comprise azacitidine at a concentration of about 0.02 uM to about 20 uM. In various aspects, a composition of the invention may comprise azacitidine a concentration from about 0.01 µM to about 0.05 µM, about 0.04 µM to about 1 µM, from about 0.8 µM to about 3 µM, from about 1 uM to about 10 µM, from about 5 µM to about 15 µM, or from about 10 µM to about 25 µM. Preferably the composition of the invention may comprise azacitidine at a concentration of 0.2 µM to 2 µM.

In another aspect, a DNA methylation inhibitor of a composition of the present disclosure is zebularine. A composition of the invention may comprise zebularine at a concentration of about 0.02 uM to about 20 uM. In various aspects, a composition of the invention may comprise zebularine a concentration from about 0.01 µM to about 0.05 µM, about 0.04 µM to about 1 µM, from about 0.8 µM to about 3 µM, from about 1 uM to about 10 µM, from about 5 µM to about 15 µM, or from about 10 µM to about 25 µM. Preferably the composition of the invention may comprise zebularine at a concentration of 0.2 µM to 2 uM.

In yet another aspect, a composition may include a combination of two or more DNA methyltransferase inhibitors. For instance, a composition may include two or more DNA methyltransferase inhibitors selected from the group consisting of decitabine, 5-fluoro-2'-deoxycytidine (FdCyd), azacitidine (also known as Vidaza™), and zebularine. In some embodiments, a composition may include three or more DNA methyltransferase inhibitors.

In yet another aspect a composition may include a DNA methyltransferase and a compound that increases the bioavailability or decreases the metabolism of the DNA methyltransferase. For instance, a composition may include a nucleoside analog DNA methyltransferase and a cytidine deaminase inhibitor that slows the metabolism of the nucleoside analog DNA methyltransferase to inactive metabolites. For instance, the composition may include FdCyd and a cytidine deaminase inhibitor tetrahydrouridine (THU) that inhibits metabolism and increases the bioavailability of FdCyd.

A suitable composition of the present disclosure may be a pharmaceutically acceptable composition. For instance, a composition may include a DNA methyltransferase inhibitor, and one or more pharmaceutically acceptable carriers, solvent, or excipients. For instance, suitable aqueous solvents may include any pharmaceutically acceptable aqueous solvent. In some embodiments, an aqueous solvent is sterile water for injection. In other embodiments, an aqueous solvent is a saline solution. Suitable saline solutions may be about 0.1% (w/v) to about 1% (w/v) sodium chloride. For example, a saline solution may be about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v) sodium chloride. These values can also be used to define a range, such as from about 0.1% (w/v) to about 0.5% (w/v) sodium chloride, about 0.25% (w/v) to about 0.75% (w/v) sodium chloride, or about 0.5% (w/v) to about 1% (w/v) sodium chloride. In yet other embodiments, an aqueous solvent is a dextrose solution. Suitable dextrose solutions may be about 2.5% (w/v) to about 5% (w/v) dextrose. For example, a saline solution may be about 2.5% (w/v), about 3% (w/v), about 3.5% (w/v), about 4% (w/v), about 4.5% (w/v), or about 5% (w/v). These values can also be used to define a range. In yet other embodiments, an aqueous solvent is Ringer's Injection or Lactated Ringer's Injection. In some embodiments, compositions of the invention may further comprise one or more pharmaceutically acceptable excipients suitable for parenteral administration and/or one or more additional active ingredients. Non-limiting examples of excipients may include preservatives, antioxidants, pH modifiers and buffers, chelating agents, antimicrobial agents, tonicity-adjusting agents, and combinations of any of these agents. The choice of suitable excipients will be influenced, in part, by the intended route of administration. Compositions formulated to be administered as a bolus in the intrathecal space typically will contain fewer, if any, preservatives, antioxidants, pH modifiers and buffers, chelating agents, antimicrobial agents, and tonicity-adjusting agents.

Non-limiting examples of preservatives or antioxidants may include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof. In an exemplary embodiment, the preservatives are an antioxidant, such as a-tocopherol or ascorbate, and antimicrobials, such as parabens, chlorobutanol or phenol.

Non-limiting examples of pH modifiers and buffers may include citric acid, acetic acid, tartaric acid, malic acid, fumaric acid, hydrochloric acid, lactic acid, phosphoric acid, sorbic acid, benzoic acid, sodium acetate, sodium borate, sodium carbonate, sodium bicarbonate, sodium phosphate, and potassium phosphate.

In some embodiments, a chelating agent may be included as an excipient to immobilize oxidative groups.

An antimicrobial agent may also be included as an excipient to minimize the degradation of the compound according to this disclosure by microbial agents, including but not limited to bacteria and fungi. Non-limiting examples of antimicrobials may include parabens, chlorobutanol, phenol, calcium propionate, sodium nitrate, sodium nitrite, Na₂EDTA, and sulfites including but not limited to sulfur dioxide, sodium bisulfite, and potassium hydrogen sulfite.

Non-limiting examples of tonicity agents may include, but are not limited to, mannitol, dextrose, sodium chloride, sorbitol and boric acid. NaCl, glucose, and sucrose.

The pH of a pharmaceutically acceptable composition of the present disclosure will be influenced, in part, by the intended route of administration. In some embodiments, the pH is about 3, about 3.5, about 4, about 4.5, about 5, about 5.5, about 6, about 6.5, about 7, about 7.5 about 8, about 8.5, of about 9. In other embodiments, the pH is between about 4 and about 8, or between about 5 and about 8, or between about 6 and about 8. In still other embodiments, the pH is between about 4.5 and about 8, or between about 4.5 and about 7.5. In yet other embodiments, the pH is between about 5 and about 7.5, or between about 5.5 and about 8. In alternative embodiments, the pH is between about 5.5 and about 7.5. The pH of a pharmaceutical composition may be adjusted with acids or bases such as hydrochloric acid or sodium hydroxide, or by the addition of a pH modifier, as described above.

In an aspect, a composition of the present disclosure may include carriers, excipients, or solvents that are suitable for parenteral routes of administration including intravenous, intramuscular, intraperitoneal, subcutaneous, intradermal, intracerebralventricular, or other suitable routes of administrations known in the art. For instance, a composition may be administered in carriers, excipients, or solvents that are suitable for intracerebralventricular (icy) administration. Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the compounds useful in this discovery, making them more lipophilic, for example, by encapsulating them in liposomes or by blocking polar groups.

In particular aspects of the present disclosure, a composition may include delivery vehicles designed to aid in crossing the blood-brain barrier of the subject, thereby increasing the availability of a composition to the neurons of a subject. Such delivery vehicles may include, for example, liposomes, lipophilic bubbles, and nanoparticles of different compositions known in the art. In further aspects, a composition may include components that increase the stability of the DNA methyltransferase inhibitors or minimize potential toxicity of an inhibitor. As will be appreciated by a skilled artisan, a variety of vehicles are suitable for delivering a composition of the present invention. Non-limiting examples of suitable delivery systems may include nanoparticles, liposomes, microemulsions, micelles, dendrimers and other phospholipid-containing systems. Methods of incorporating compositions into delivery vehicles are known in the art.

II. Methods of Treatment

Generally speaking, a method of the present application may be used to treat neurodegenerative disorders. Suitable neurodegenerative disorders are those characterized, in part, by DNA methylation differences when compared to individuals who do not suffer from such disorders. Examples of neurodegenerative disorders that may be treated by a method of the present disclosure include Huntington's disease (HD), Alzheimer's disease (AD), Parkinson's disease (PD), and amyotrophic lateral sclerosis (ALS). In an exemplary embodiment, the present application discloses a method to treat HD.

As used herein "treat" refers to reducing one or more symptoms of a neurodegenerative disorder. Non-limiting examples of specific neurodegenerative symptoms that may be reduced by a treatment of the present disclosure include motor, cognitive, and psychiatric symptoms. The motor symptoms of a neurodegenerative disorder may include involuntary muscle movement, impaired balance, impaired speech, and impaired eye movements. Cognitive symptoms may include impaired learning and thought processing. The psychiatric symptoms may include depression, insomnia, and fatigue.

The diagnosis of neurodegenerative disorders may be based, in part, on a physical and psychological examination by a physician, for the motor, cognitive, and psychiatric symptoms indicative of a neurodegenerative disorder. The diagnosis of a neurodegenerative disorder may also be aided by imaging techniques such as computerized tomography (CT) and magnetic resonance imaging (MRI) to detect cerebral abnormalities. Specific examples of such abnormalities may include neuronal atrophy or, for HD, Htt protein aggregates. The diagnosis of a neurodegenerative disorder may also be through functional neuroimaging with techniques such as fMRI and PET (Positron emission tomography) that reveals changes in brain activity due to neurodegeneration.

HD is also characterized by aggregation of the Huntingtin (Htt) protein. Aggregates of Htt may accumulate around the neurons of a subject with HD, and may lead to neurotoxicity. The neurotoxicity caused by the Htt aggregates, may lead to decreased function of the nervous system and may be responsible for the motor, cognitive, as well as psychiatric symptoms of HD.

The risk of developing neurodegenerative disorders may be evaluated by genetic testing, using a biological sample of a patient, such as blood. For HD, the HTT gene may be analyzed for an expansion mutation of the cytosine-adenine-guanine (CAG) triplet. The risk of developing HD may be evaluated especially in subjects whose parents have the disorder by genetic testing. The genetic testing for HD may also be performed prenatally using fetal amniotic fluid, in fetuses whose one or both parents have HD.

In an aspect, treatment may relieve the neurological symptoms associated with the neurodegenerative disorder. Treatment may result in partial or complete relief of symptoms motor, cognitive, or psychiatric symptoms. The decrease or relief of symptoms may be determined by a physical and psychological examination by a physician. The decrease in symptoms may also be determined by CT and/or MRI imaging or functional neuroimaging to determine decrease in neuronal atrophy, or improvement of brain functional activity. For instance, for HD, a decrease in symptoms may be represented by a decrease in Htt protein aggregates or improvement of brain functional activity.

In an aspect a method of treatment that prevents the development of symptoms of HD might be used. A subject evaluated at risk of development of HD may be administered the treatment as a preventive measure, to stop the development of symptoms, or to stop the progression of development of symptoms of HD.

In an aspect, treatment with a composition of the present disclosure may restore the expression of several key genes, including Bdnf. The treatment may restore the expression of Bdnf exon IX, IV and VI transcripts in neurons of the subject. In an aspect the treatment may upregulate the mRNA levels of key striatal genes known to be downregulated in HD. The striatal genes that may be upregulated by treatment are for example but not limited to brain derived neurotrophic factor (Bdnf), dopamine receptor D2 (Drd2), Protein phosphatase 1 regulatory inhibitor subunit IB (Ppp1r1b), and Adenosine A2a receptor (Adora2a). In an aspect the treatment may decrease Htt protein aggregates in a subject, the decrease in Htt protein aggregates may be evaluated by imaging techniques known in the art. A physician may assess the effectiveness of the treatment by evaluating cerebral images before and after treatment to evaluate the decrease of Htt protein aggregates in a subject.

In an aspect, the subject to be treated is a human subject. In other aspects, the subject to be treated may be any mammalian species that can exhibit symptoms of neurodegenerative disorder. For instance, the subject may be a human that exhibits symptoms of HD or be at risk of developing HD. Methods of identifying subjects that are suffering from a neurodegenerative disorder, or that are at risk of suffering from a neurodegenerative disorder, are known in the art.

In various methods of the present disclosure, a composition of the disclosure may be administered by intravenous, intramuscular, subcutaneous, intradermal, intraperitonial, or intranasal route of administration. In various methods of the present disclosure, a composition may also be administered into the brain of a subject by intraventricular route, by intracavitary route, into the interstitial system of the brain, or by intracerebral implantation. A composition may also be administered by any other route of administration known in the art that may contact a composition to cells of the brain. In preferred embodiments, a composition of the invention may be administered by methods that contacts one or more neurons of a subject. For instance, a composition of the invention may be administered by intraventricular, intracavitary, or into the interstitial system of the brain.

In a method of the present disclosure, a composition may be administered as a single injection (e.g. bolus administration), as a continuous infusion, or by an intracerebral implantation. In an aspect the interval between doses may be from less than about 1 day to about 4 days, from about 3 days to about 7 days, from about 5 days to about 10 days, from about 7 days to about 15 days, from about 14 days from about 28 days, from about 25 days to about 45 days, from about 30 days to about 60 days, and from about 50 days to about 70 days.

Generally, a compound will be administered in a therapeutically effective amount which includes prophylactic amounts or lower dosages for example, when combined with another agent. As used herein, "an effective amount" refers to doses of compound sufficient to provide circulating concentrations high enough to impart a beneficial effect on the recipient thereof. The precise amount to be administered can be determined by the skilled practitioner in view of desired dosages, side effects, and medical history of the patient.

In another aspect a method of treatment may include a combination therapy of the DNA methyltransferase inhibitors and other medications that reduce the motor, cognitive, and psychiatric symptoms of a neurodegenerative disorder. The other drugs used in combination may include for example but not limited to tetrabenazine, antipsychotic drugs, neuroleptics, mood stabilizers, and antidepressants. The treatment with DNA methyltransferase inhibitors may also be used in combination with other lifestyle therapies including for example but not limited to physical therapy and psychotherapy.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 7A:
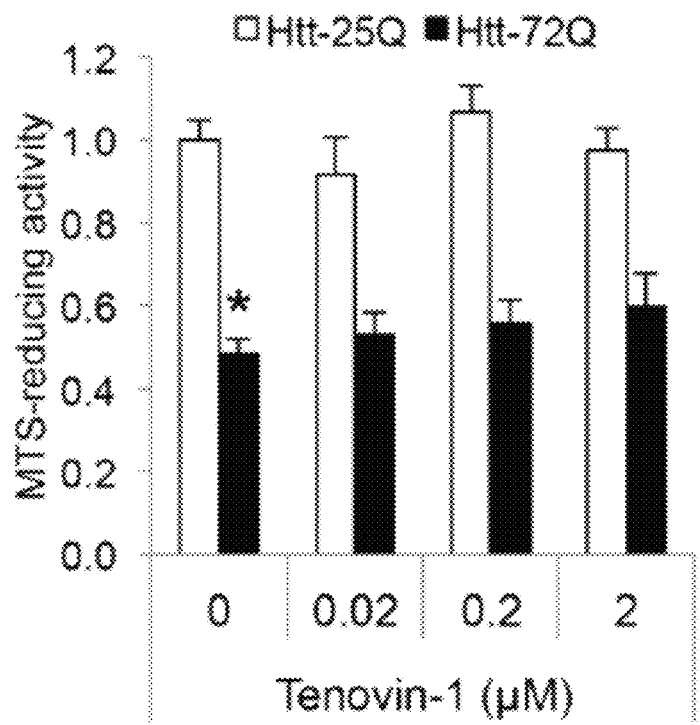
FIG. 7A-B illustrate the validation of hits from epigenetic drug screen.
Figure 7B:
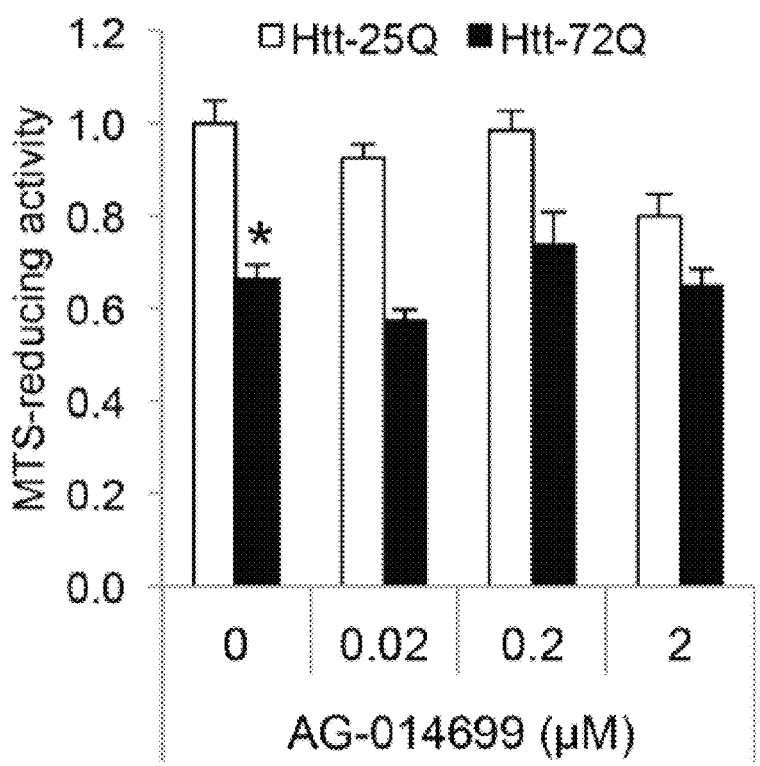
Figure 8A:
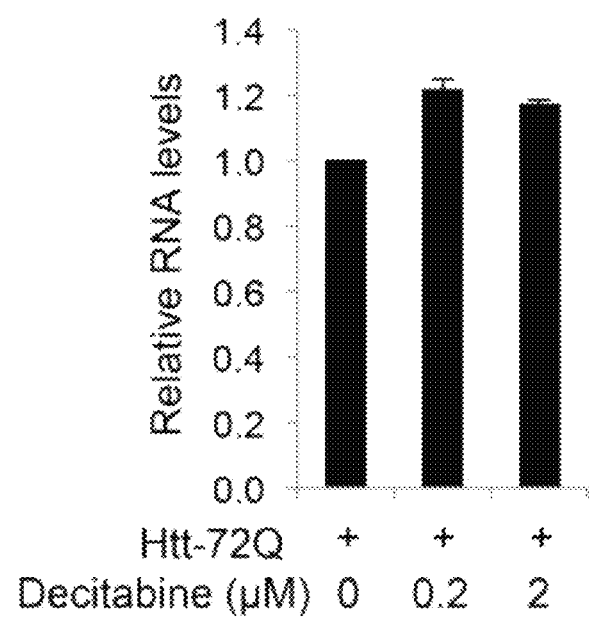
FIG. 8A-D illustrate that the inhibition of DNMTs attenuates mutant Htt aggregates in primary cortical neurons.
Figure 8B:
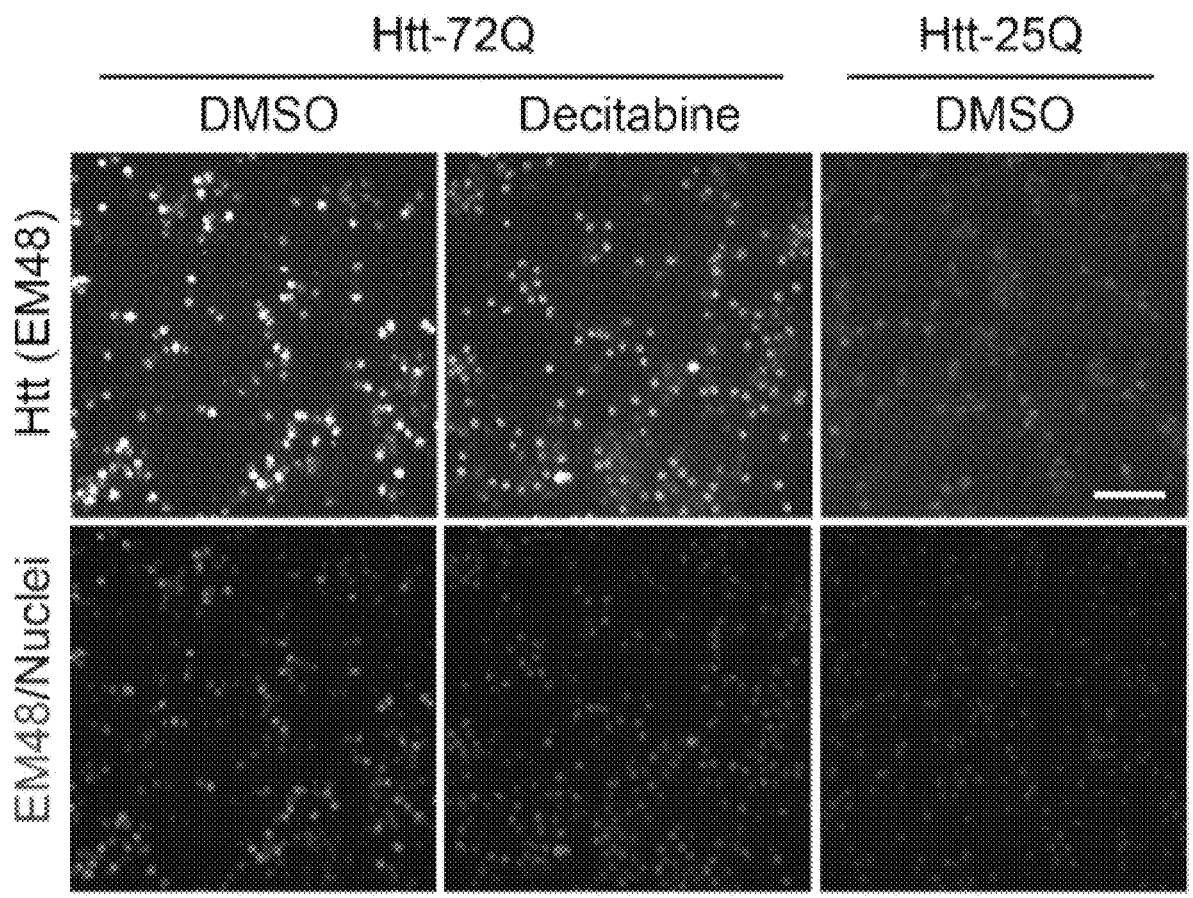
Figure 8C:
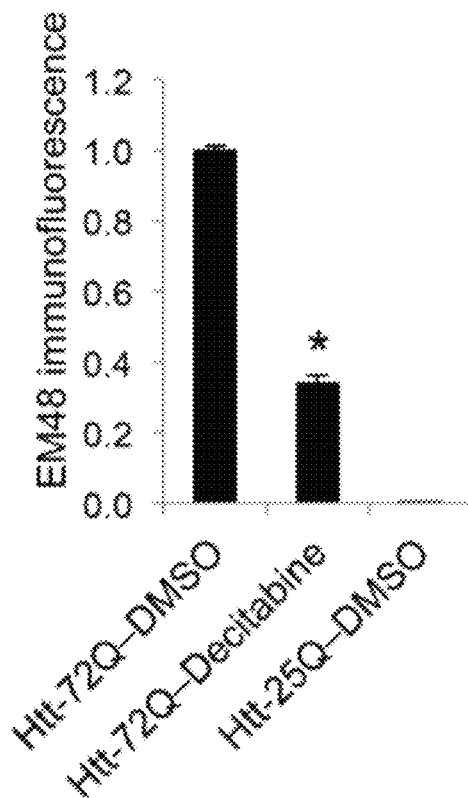
Figure 8D:
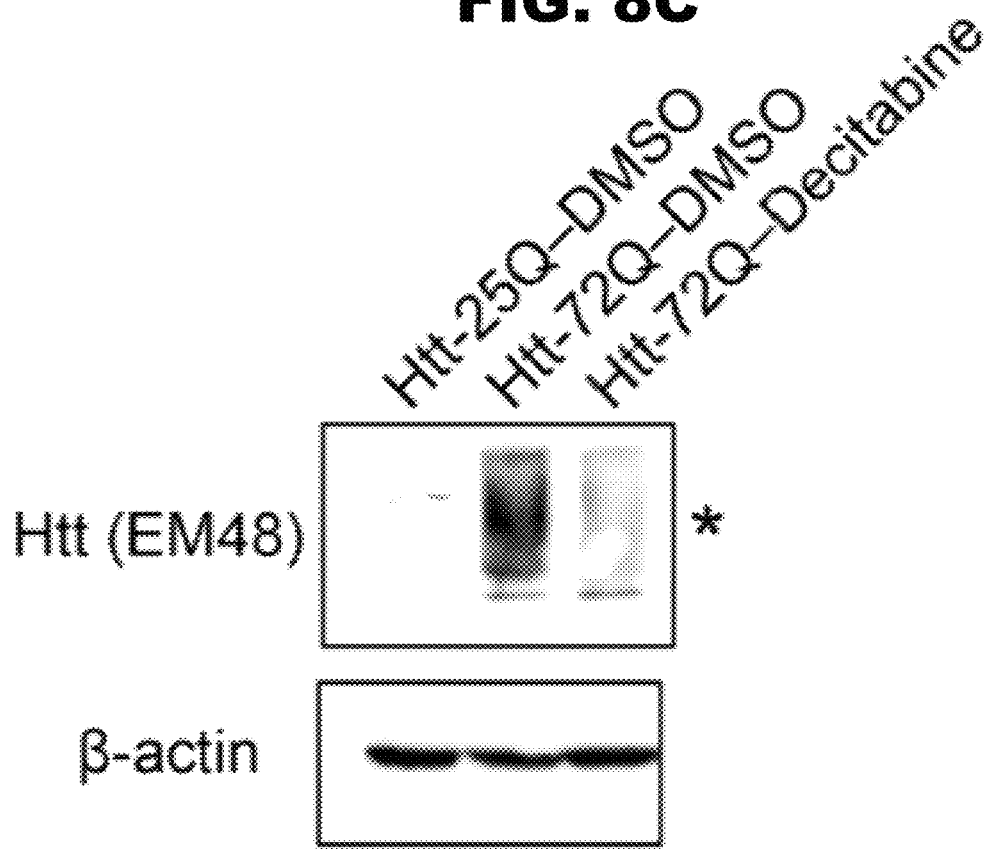

Example 1. DNA Demethylating Agents Protect Neurons from Mutant Htt-Induced Cytotoxicity To identify the critical epigenetic pathways that contribute to the death of mutant Htt-expressing neurons, we performed an epigenetic drug screen using a library composed of 84 epigenetic compounds with known targets, including writers, erasers, and readers of the epigenetic code (FIG. 1A and Table 1). As epigenetic gene regulation is a cell-type specific mechanism, we used a physiologically relevant, post-mitotic cortical neuron culture system for this screen. In this system, lentivirus-mediated expression of the exon 1-encoded N-terminal fragment of mutant Htt (Htt-72Q with a 72 glutamine repeat), but not wild-type (WT) Htt (Htt-25Q), induces neurotoxicity[38]. The N-terminal short fragments of mutant Htt, which can be generated in cells by proteolytic cleavage of the full-length Htt or alternative splicing, is known to be more cytotoxic than the full-length protein and is expressed in HD patients[39-44]. In the drug screen, the viability of Htt-expressing cortical neurons was determined by the resazurin (Alamar Blue) assay, a quantitative measurement of mitochondrial metabolic activity, which correlates with cell viability. Following validation assays of possible screen "hits" using the MTS assay, we identified the cytosine nucleoside-analog DNA methyltransferase (DNMT) inhibitor decitabine, as the most effective drug in our mutant Htt neuroprotection screen (FIG. 1B, FIG. 7A, and FIG. 7B). Remarkably, decitabine exhibited significant neuroprotection with concentrations as low dose as 0.02 µM with nearly full protection at 0.2 µM in our HD system (FIG. 1B). Decitabine, also known as 5-aza-2'-deoxycytidine or Dacogen™ (DAC), is a U.S. Food and Drug Administration (FDA)-approved drug and has been used clinically for the treatment of cancers, including myelodysplastic syndrome (MDS) and acute myeloid leukemia (AML)[26, 45], but not for neurodegenerative disorders. We further verified the protective effects of decitabine in mutant Htt-expressing primary cortical neurons using two additional assays: neurite degeneration by quantifying the loss of neurofilament (NF) immunofluorescence intensity, an early marker of neuronal toxicity (FIG. 1D and FIG. 1E), and cell death by scoring condensed or fragmented nuclei (FIG. 1F). Since decitabine is an epigenetic agent that affects gene expression, we confirmed that decitabine does not decrease the expression of Htt-72Q in our system compared to vehicle control by qRT-PCR (FIG. 8A). We then tested if treatment with decitabine affects the burden of mutant Htt aggregates—an HD pathological hallmark—in primary cortical neurons using an antibody that preferentially detects mutant Htt aggregates ((FIG. 8B-D). By both immunofluorescence and immunoblot analyses, we found that decitabine could decrease the levels of mutant Htt aggregates in Htt-72Q-expressing neurons. Given that misfolded and aggregated Htt may interfere with several important biological functions in neurons, its reduction may contribute to neuroprotection by decitabine.

To verify the effect of DNMT inhibition against mutant Htt toxicity, we next performed similar experiments with three other well-characterized nucleoside-analog DNMT inhibitors, 5-fluoro-2'-deoxycytidine (FdCyd), 5-azacytidine (azacitidine, 5-AC, Vidaza™), and zebularine. The latter two drugs are ribonucleoside analogs, which target primarily RNA rather than DNA, and small fractions of these drugs can be converted to their deoxyribose form in cells, thereby leading to inhibition of DNA methylation[46, 47]. 5-azacytidine, like decitabine, is a FDA-approved, potent anti-cancer drug that has been used for the treatment of MDS and AML. FdCyd was developed by the National Cancer Institute and is currently being investigated in ongoing clinical trials in solid tumors. Interestingly, the deoxyribonucleoside analog FdCyd, but not the ribonucleoside analogs, zebularine and 5-azacytidine, demonstrated neuroprotective effects against mutant Htt-induced toxicity in primary cortical neurons in cell viability and neurite degeneration assays (FIG. 1G, FIG. 1H, and FIG. 9A-9C), suggesting that the deoxyribonucleoside form of DNMT inhibitors, which act directly through DNA, exerts neuroprotective activity in HD neurons.

Figure 9A:
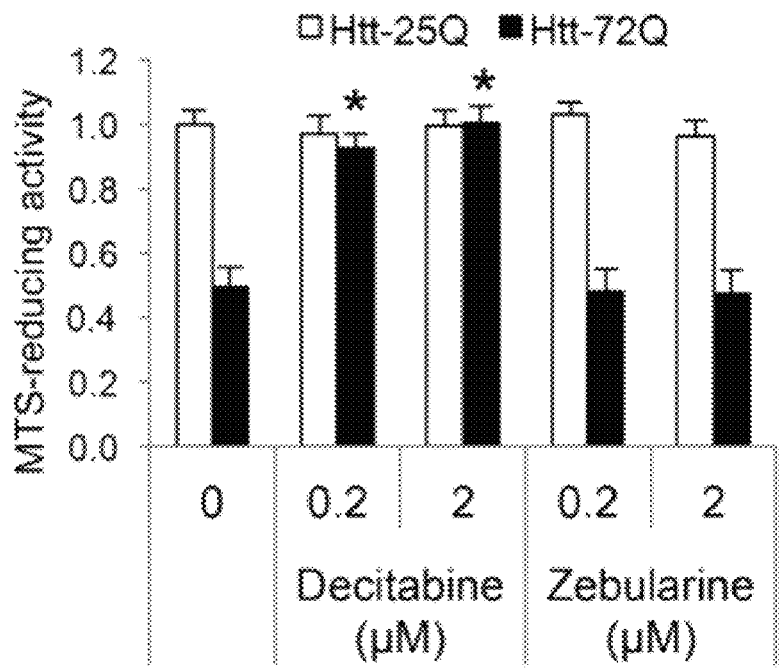
FIG. 9A-F illustrate the effects of nucleoside analog DNMT inhibitors on mutant Htt-induced toxicity in primary neurons.
Figure 9B:
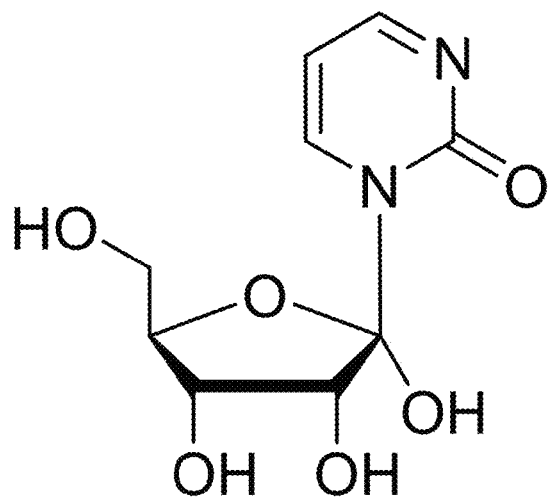
Figure 9C:
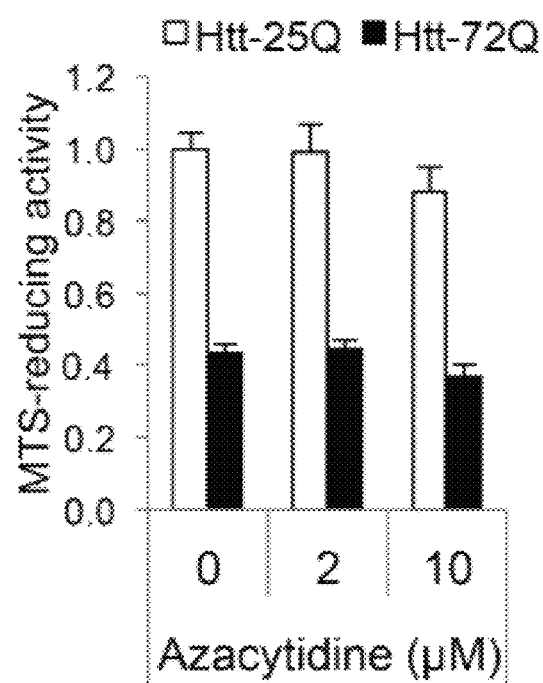
Figure 9D:
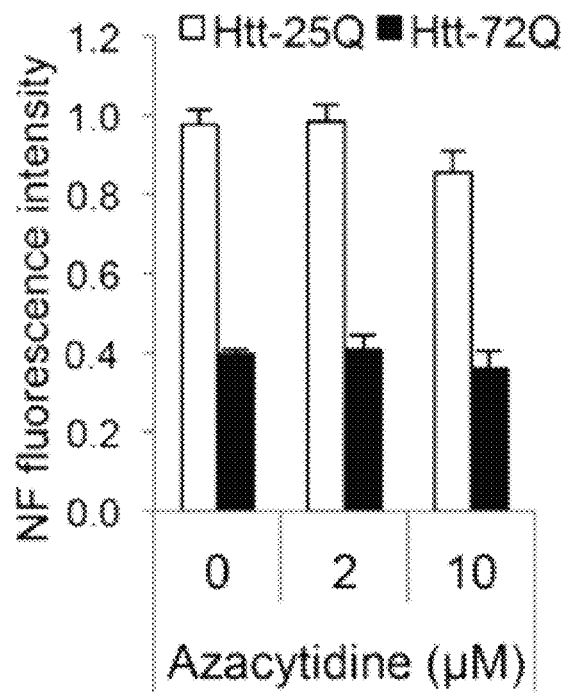
Figure 9E:
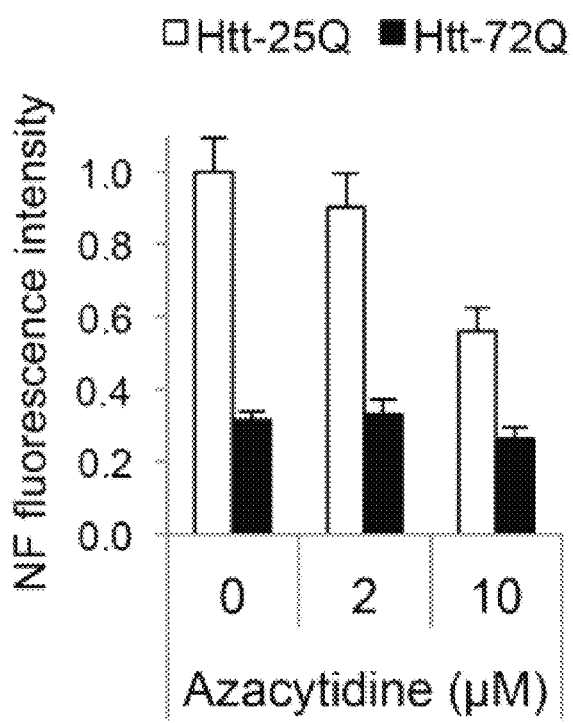
Figure 9F:
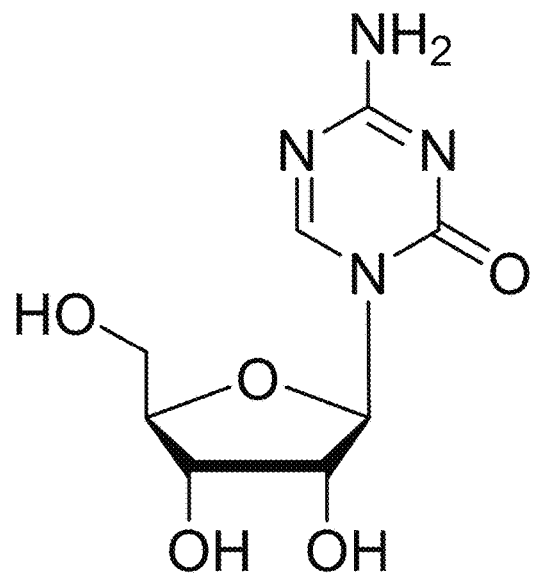
Figure 10A:
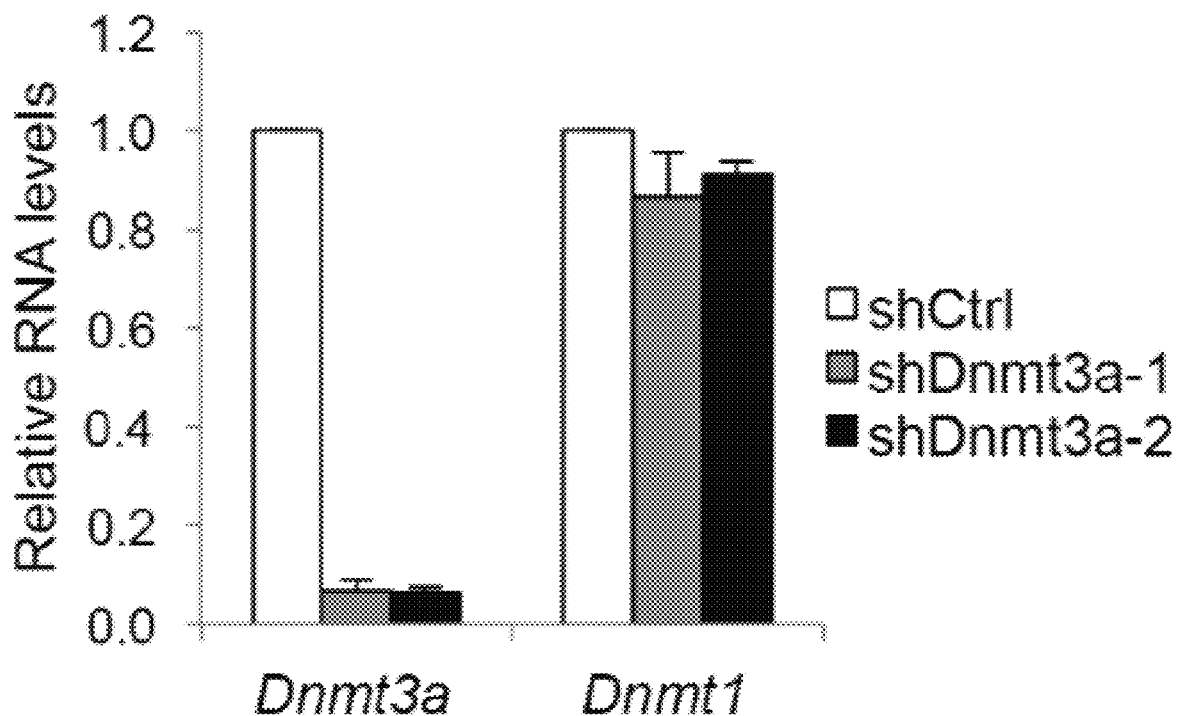
FIG. 10A-B illustrates knockdown of DNMT3A or DNMT1 did not decrease the expression of the other DNMTs.
Figure 10B:
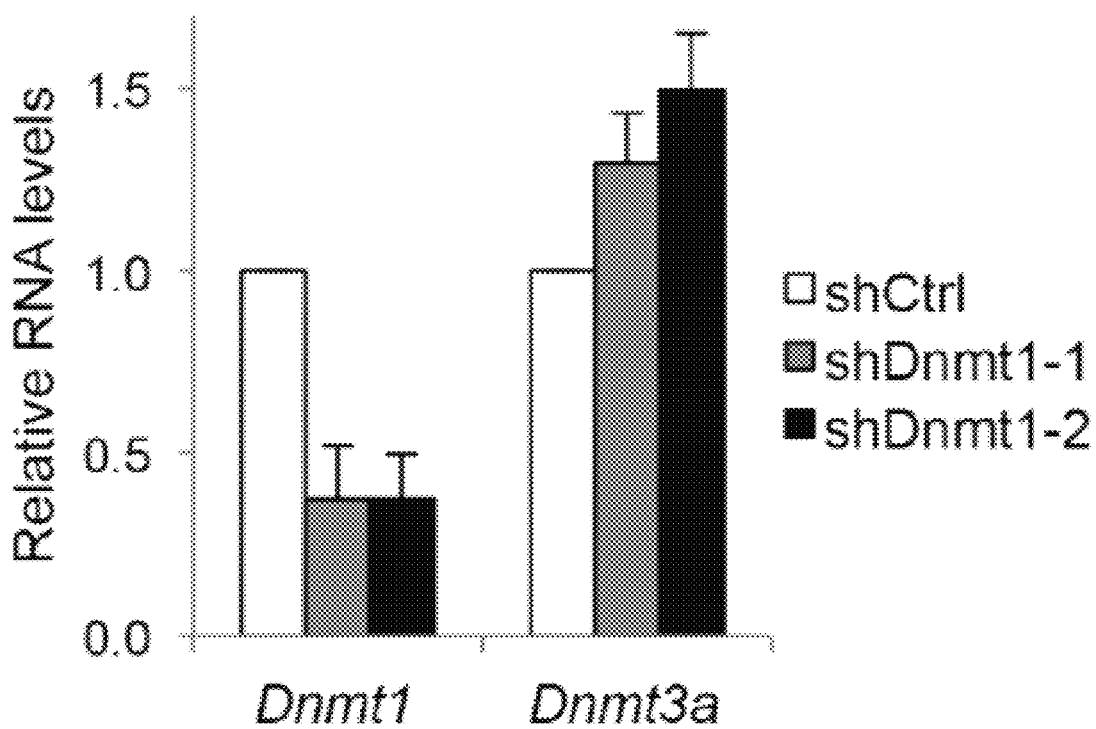

To test if DNMTs play a role in the HD striatal neurons, one of the most severely affected cell types in the disease, we established a cultured striatal neuron model, in which the N-terminal exon-1 fragment of mutant or WT Htt was expressed by lentiviral infection. Strikingly, treatment with decitabine or FdCyd also attenuated mutant Htt-induced striatal neurite degeneration (FIGS. 1H and 1I). Similar to cortical neurons, 5-azacytidine did not inhibit mutant Htt-induced neurite degeneration in striatal neurons (FIG. 9D). Together, results utilizing two disease-relevant neuronal cell types suggest that DNMTs play an important role in mutant Htt-induced neurodegeneration.

Example 2. Reduced DNMT3A or DNMT1 Expression Protects Neurons from Mutant Htt-Induced Toxicity Because inhibition of DNMTs by decitabine and FdCyd rescued neurons from mutant Htt-induced toxicity, we next determined if molecular inhibition of DNMTs by RNA interference (RNAi) attenuates neuronal death in the mutant Htt context. Among members of the DNMT family, post-mitotic neurons in the brain are known to highly express DNMT3A and DNMT1[27, 35, 36, 48]. Knockdown of either DNMT3A or DNMT1 protein by lentiviral delivery of two distinct short hairpin RNAs (shRNAs) for each DNMT significantly increased the viability of mutant Htt-expressing cortical neurons (FIG. 2A-2D). Knockdown of DNMT3A or DNMT1 did not decrease the levels of the other DNMT's mRNA or protein (FIG. 2A-B, FIG. 10A-B), demonstrating specificity of the shRNAs used. These findings indicate that both DNMT3A and DNMT1 are required for mutant Htt-induced neuronal death. Taken together, these results demonstrate that DNA methylation plays a causal role in mutant Htt-induced neurotoxicity, likely by repressing the transcription of genes important for neuronal survival and function.

Figure 3C:
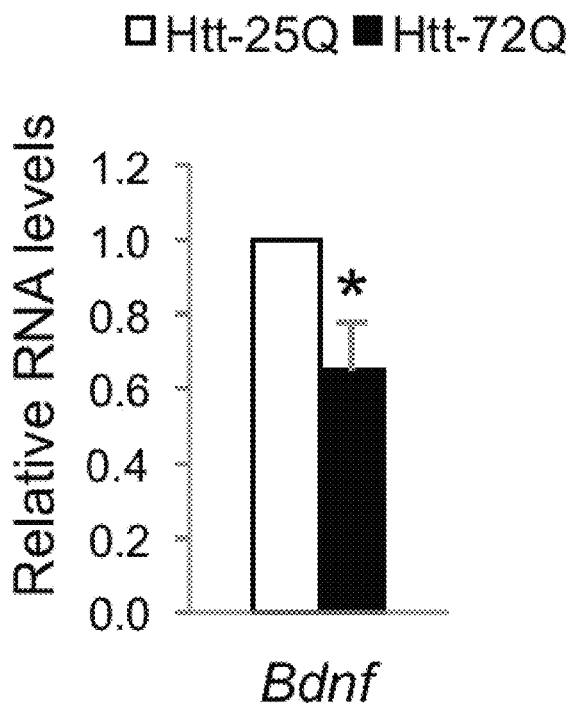
Figure 3C:
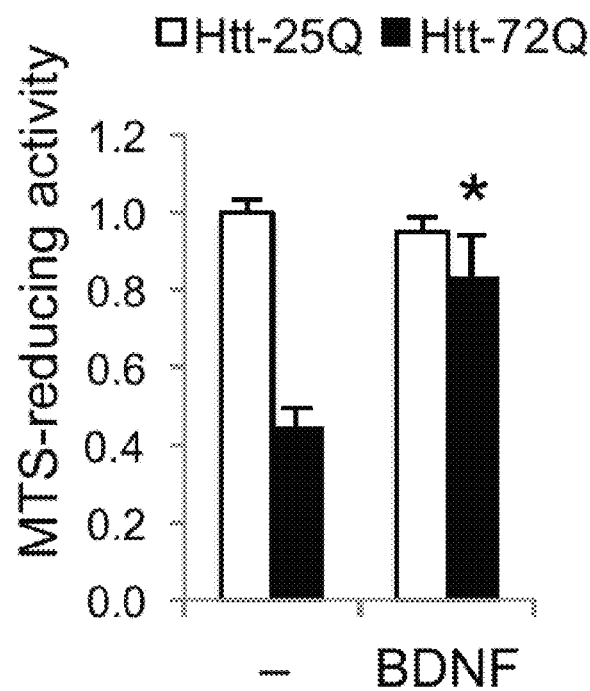
Figure 3C:
Figure 3C:
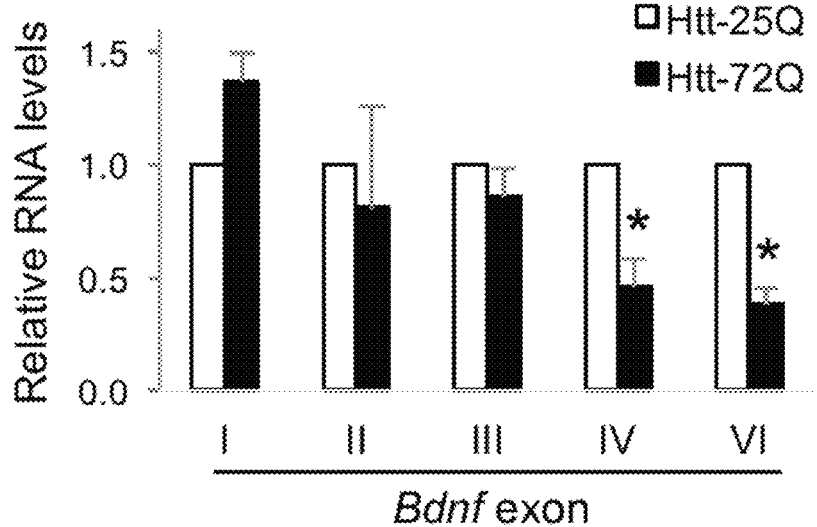

Example 3. Inhibition of DNMTs Restores Bdnf Gene Expression in Mutant Htt-Expressing Cortical Neurons BDNF is a major neurotrophic factor involved in fundamental brain processes, including neuronal survival, synaptic plasticity, and learning and memory. Bdnf mRNA and protein levels were found to be decreased in the brains of human HD patients and mouse models, which is thought to contribute to HD pathology[11, 12, 15]. Consistent with these observations, Bdnf expression was reduced by mutant Htt expression in primary cortical neurons (FIG. 3A). Addition of recombinant BDNF protein in the culture medium was sufficient to rescue cortical neurons from mutant Htt-induced toxicity (FIG. 3B), suggesting an important role for BDNF in the survival of mutant Htt-expressing neurons. Using Bdnf as a model gene, we next focused on determining if Bdnf transcriptional repression could be rescued by manipulating DNA methylation in mutant Htt-expressing neurons. As the Bdnf gene has a complex structure with multiple noncoding exons and a common protein coding exon, we first examined the differential expression of major exon-specific Bdnf transcripts in primary cortical neurons. Each noncoding exon has an independent promoter, and the expression of the exon-specific transcript is differentially regulated in response to diverse extracellular stimuli and signaling events (schematic in FIG. 3C)[49, 50]. Mutant Htt-expressing cortical neurons exhibited decreased expression of Bdnf mRNA at a time before neurons begin to die, specifically Bdnf exon IV- and VI-containing transcripts, compared to control neurons expressing WT Htt-25Q or the empty vector (FIG. 3C).

Figure 3D:
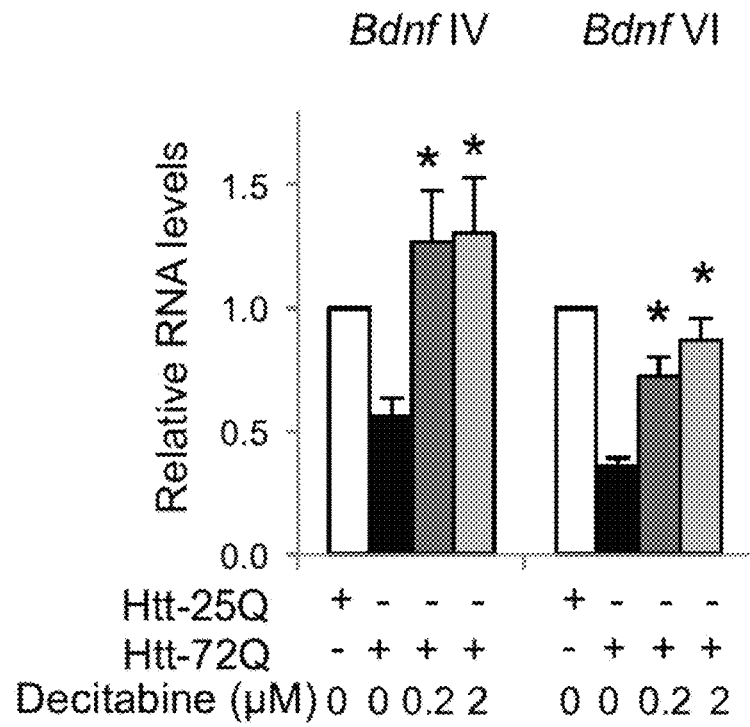
Figure 3E:
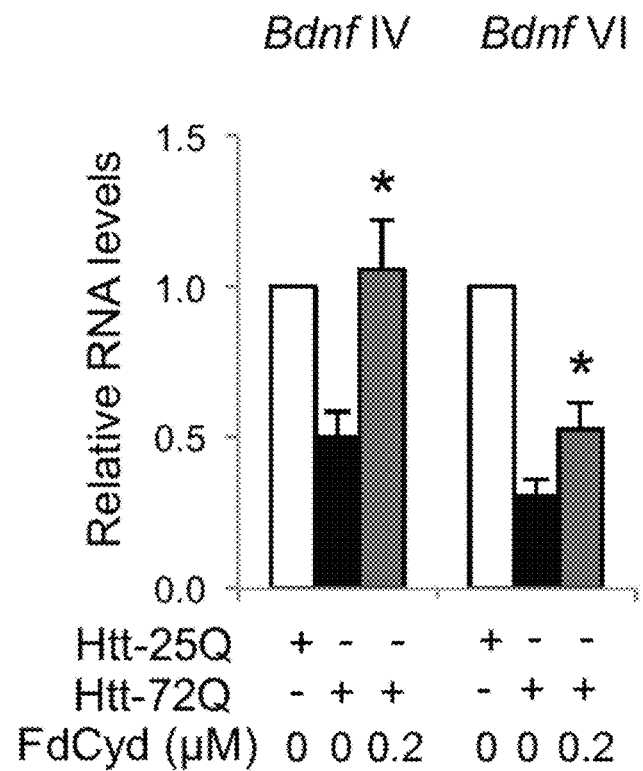
Figure 3F:
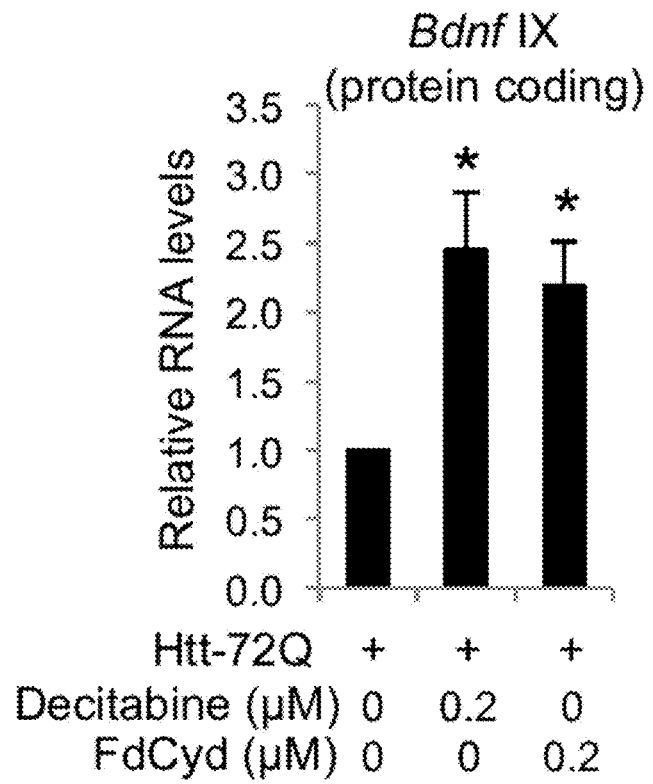
Figure 3G:
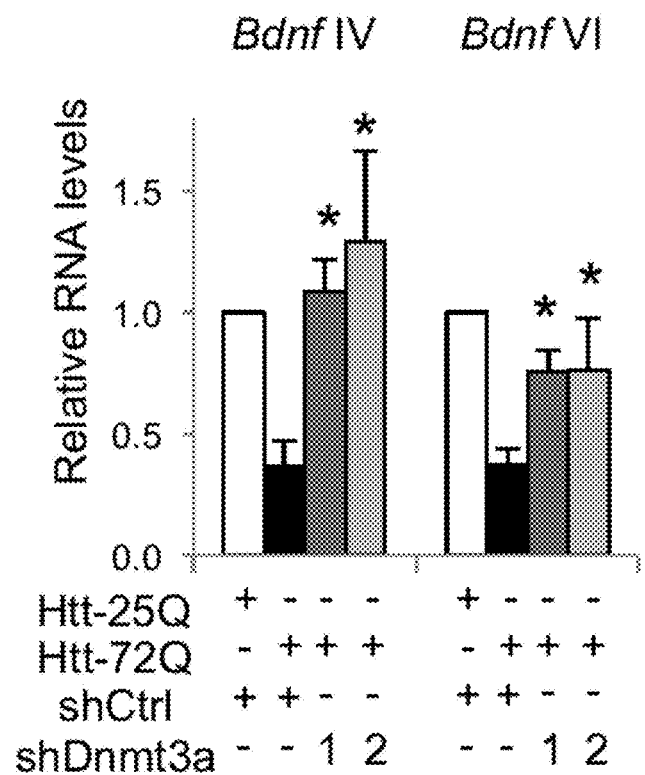
Figure 3H:
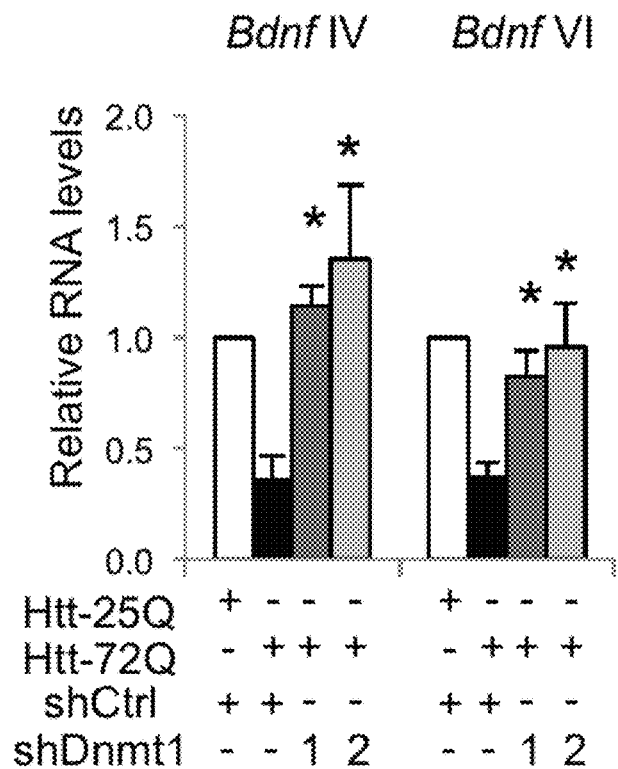

Next, to test the hypothesis that abnormal DNA methylation contributes to the downregulation of Bdnf mRNA, we examined if pharmacological inhibition of DNMTs could rescue the expression of Bdnf exon IV and VI-containing mRNAs in mutant Htt-expressing cortical neurons by qRT-PCR analysis (FIG. 3D-E). Intriguingly, both decitabine and FdCyd restored the levels of Bdnf exon IV and VI transcripts at doses effective for neuroprotection (FIG. 3D-E). These DNMT inhibitors also increased the levels of the common coding exon IX transcript (total Bdnf mRNA) in mutant Htt-expressing cortical neurons (FIG. 3F). Consistent with the effects of DNMT inhibitors on Bdnf transcription, knockdown of DNMT3A or DNMT1 in mutant Htt-expressing cortical neurons using two shRNAs targeting each DNMT reversed the mutant Htt-triggered decrease in Bdnf exon IV and VI mRNAs (FIG. 3G-H). These results suggest that both DNMTs contribute to downregulation of Bdnf mRNA in HD neurons.

Figure 3I:
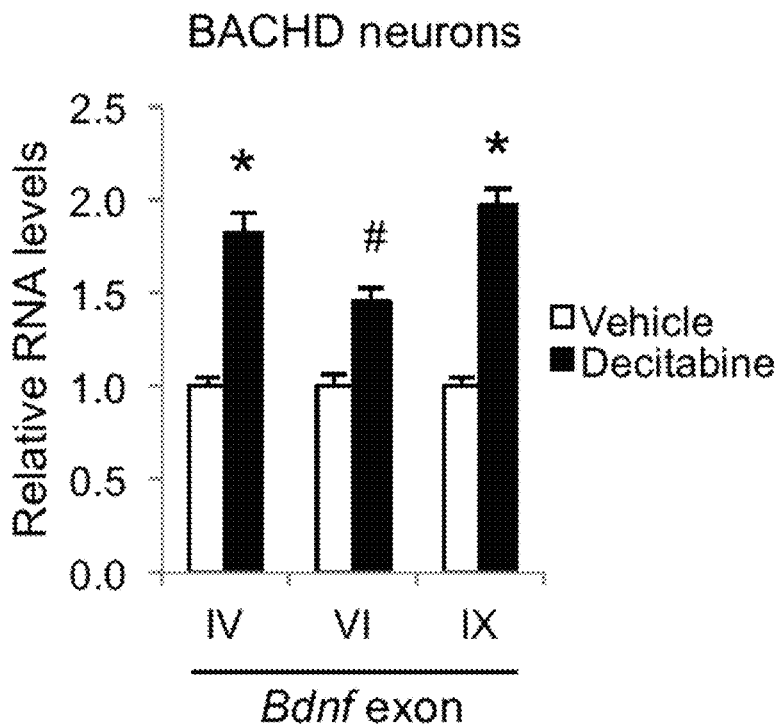

To verify these findings using an alternative HD model system, we next determined if decitabine could upregulate Bdnf mRNA expression in primary cortical neurons derived from bacterial artificial chromosome (BAC)-mediated HD transgenic (BACHD) mice, which express full-length mutant Htt[53]. BACHD mice exhibit progressive motor deficits and late-onset selective neuropathology in the cortex and striatum[53]. Inhibition of DNMTs by decitabine in BACHD mouse cortical neurons increased Bdnf exon IV- and VI-containing as well as total Bdnf (exon IX) mRNAs by qRT-PCR (FIG. 3I), supporting the findings obtained using neurons expressing the N-terminal fragment of mutant Htt (FIG. 3D). Collectively, these results suggest that DNMT inhibition exhibits neuroprotective effects in the context of mutant Htt in part through the upregulation of Bdnf.

Figure 4A:
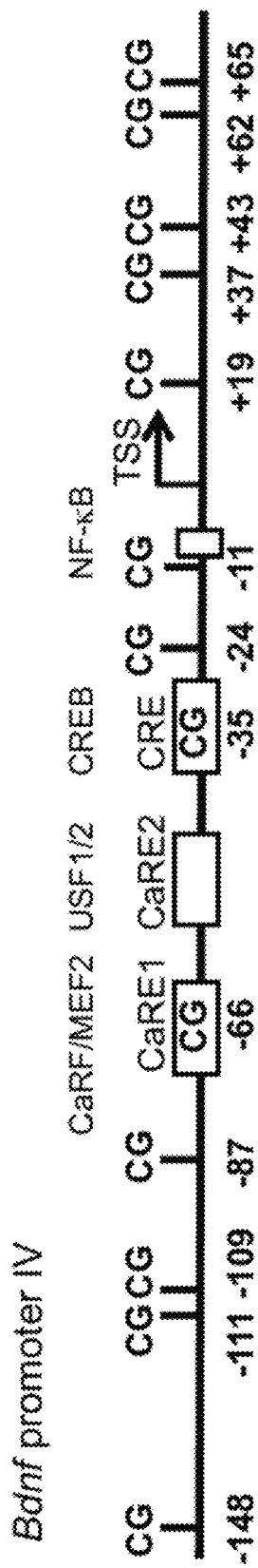
FIG. 4A-4H illustrate that mutant Htt increased the levels of DNA methylation at Bdnf exon IV regulatory region in primary cortical neurons.
Figure 4B:
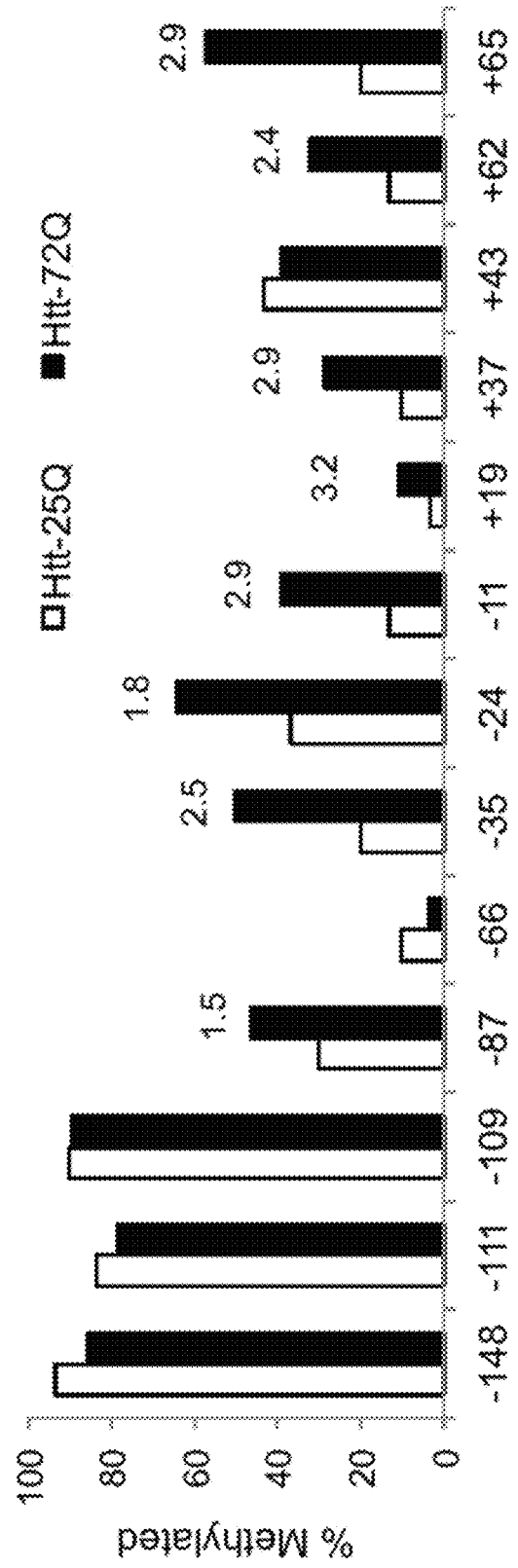
Figure 4C:
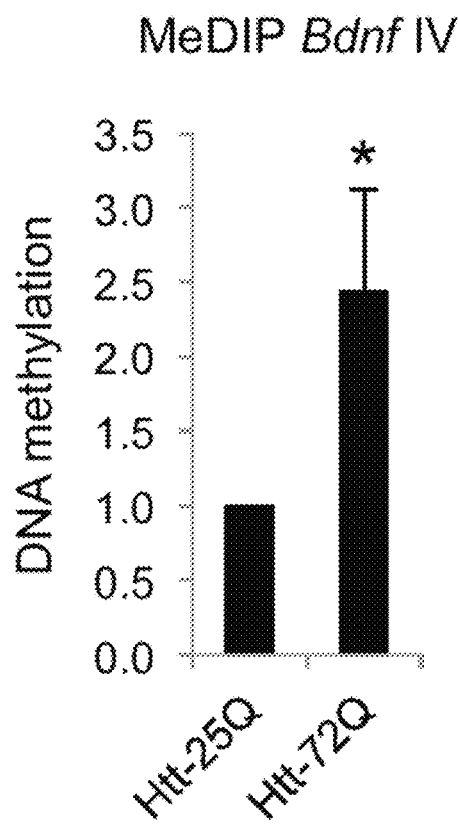
Figure 11A:
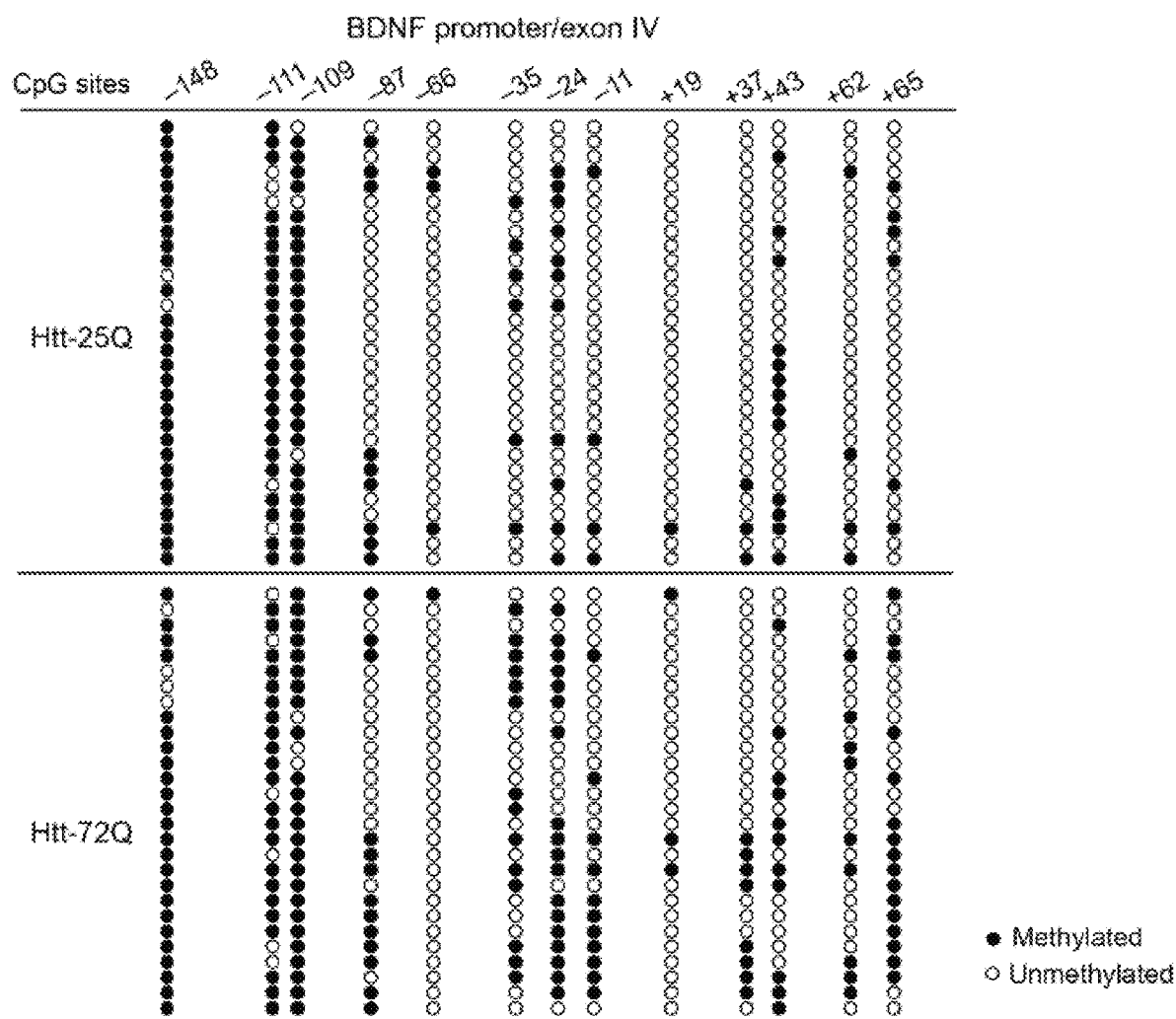
FIG. 11A-B illustrates the analysis of CpG methylation status of Bdnf exon IV and VI regulatory regions in mutant Htt-expressing primary cortical neurons.
Figure 11B:
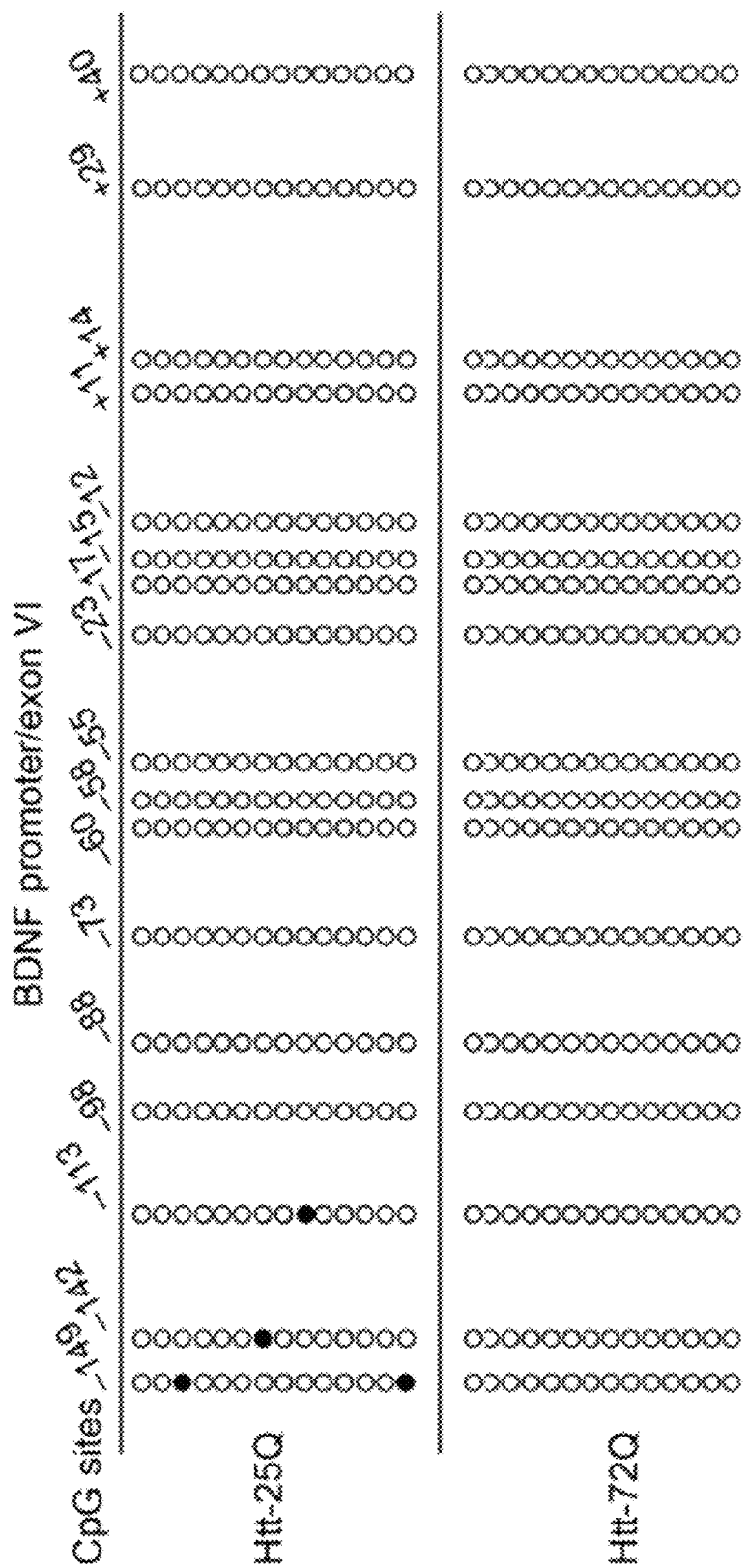

Example 4. Mutant Htt Increased the Levels of DNA Methylation in the Bdnf Exon IV Regulatory Region in Primary Cortical Neurons Because Bdnf exon IV and VI transcripts in mutant Htt-expressing cortical neurons are increased by DNMT inhibition (FIGS. 3D-E, and FIGS. 3G-3I), we next tested the hypothesis that mutant Htt stimulates DNA methylation in the promoter regions of these two exons, leading to repression of these transcripts. The Bdnf promoter IV harbors several transcription factor binding sites, including calcium responsive elements, CaRE1, CaRE2, and CRE (schematic in FIG. 4A) and is activated in response to various extracellular stimuli in vivo[54-56]. The levels of DNA methylation in the Bdnf exon IV regulatory region that contains 13 CpG sites (base pairs −148 to +65 relative to the transcriptional start site (TSS)) was assessed by bisulfite conversion followed by DNA sequencing, a widely used technique to measure levels of cytosine methylation on specific genomic regions with single CpG resolution. Among the 13 CpGs sites examined, methylation of eight CpGs between base pairs −87 to +65 was increased (1.5- to 3.2-fold) by mutant Htt expression (FIG. 4B and FIG. 11A). Three CpG sites located between base pairs −148 and −109, including the previously reported methyl CpG binding protein 2 (MeCP2) binding site at the position −148[55, 56], exhibited robust methylation with no significant difference between WT and mutant Htt-expressing neurons (FIG. 4B). Thus the bisulfite sequencing results revealed that mutant Htt-expressing neurons exhibit an overall increase in the levels of cytosine methylation, compared to WT Htt-expressing neurons, in the regulatory region of the Bdnf exon IV surrounding the TSS (FIG. 4B and FIG. 11A). The increased levels of cytosine methylation (5-mC) in the region was independently confirmed by methylated DNA immunoprecipitation (MeDIP), which uses a specific antibody against 5-mC (FIG. 4C). These data suggest that mutant Htt expression downregulates Bdnf exon IV transcript via increased DNA methylation of the promoter. In contrast, similar bisulfite sequencing analysis for the regulatory region of Bdnf exon VI containing 19 CpG sites displayed little if any DNA methylation in both WT Htt-25Q and mutant Htt-72Q-expressing cortical neurons (FIG. 11B), indicating that Bdnf promoter VI is not a direct target of DNA methylation but is indirectly suppressed by events initiated by aberrant DNA methylation in mutant Htt-expressing neurons.

Figure 4D:
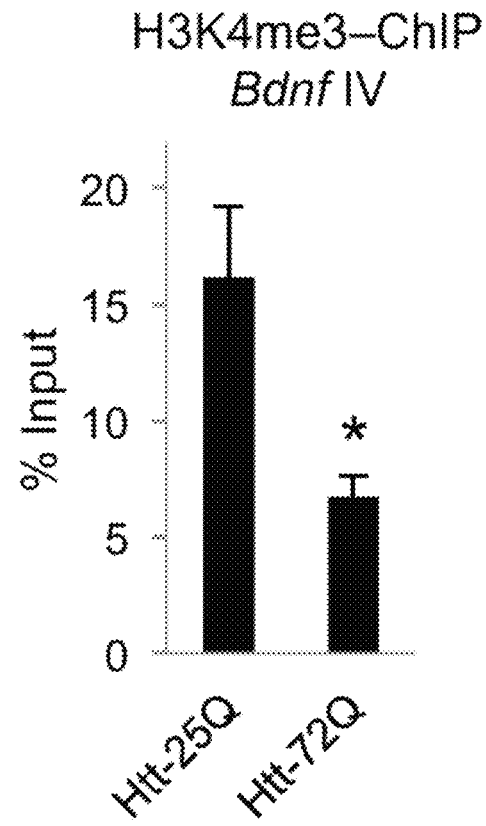

DNA methylation-mediated gene repression is generally associated with a closed chromatin structure, which is induced by cooperation with altered histone modifications[57]. By chromatin immunoprecipitation (ChIP) analysis we found that the mutant Htt-triggered increase in DNA methylation is associated with decreased trimethylation at lysine 4 of histone H3 (H3K4me3), a transcriptionally active histone mark, in the promoter region of Bdnf exon IV in mutant Htt-expressing primary cortical neurons compared to WT Htt-expressing neurons (FIG. 4D). Together, these results illustrate that mutant Htt-induced increases in DNA methylation are associated with loss of active open chromatin in this region, consistent with mutant Htt-induced transcriptional repression of Bdnf exon IV.

Figure 4E:
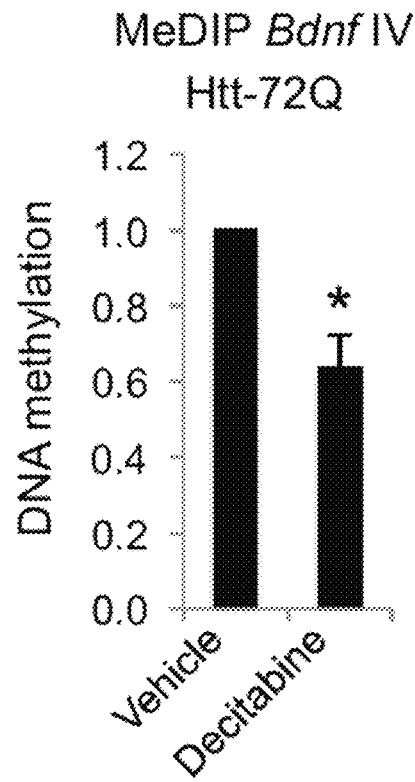
Figure 4F:
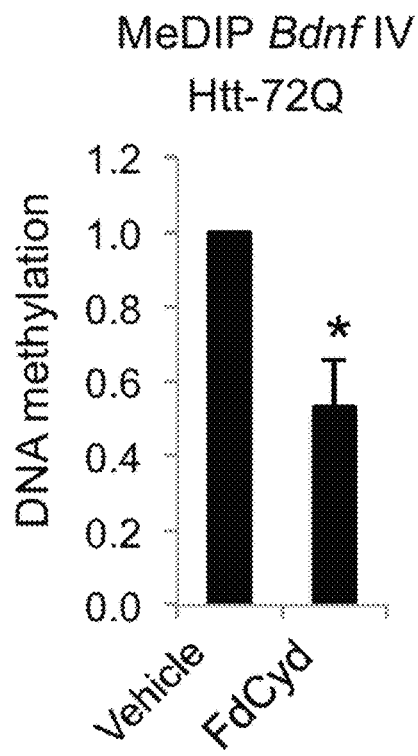
Figure 4G:
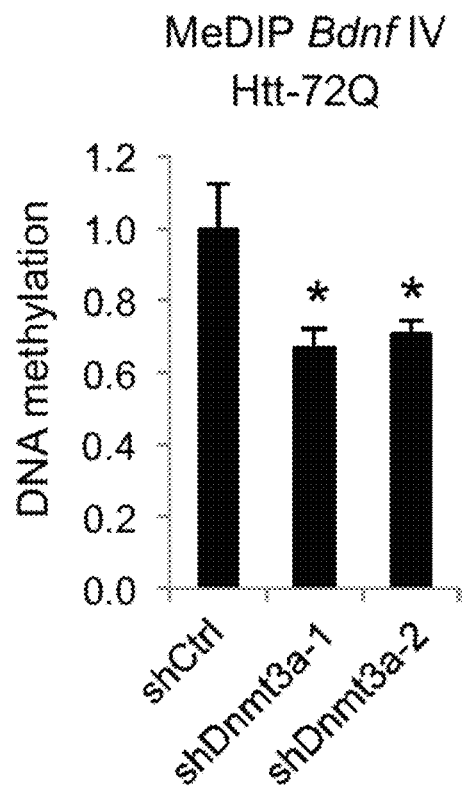
Figure 4H:
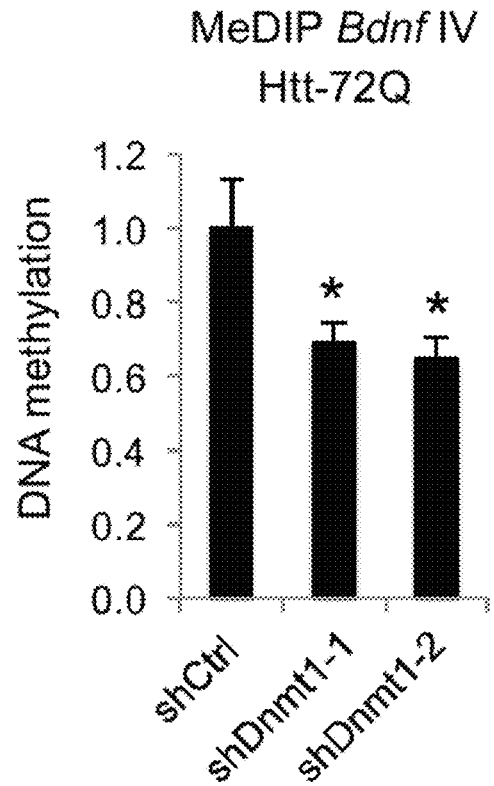

Next, to further support the hypothesis that decreased Bdnf exon IV transcription by mutant Htt is the consequence of changes in DNA methylation at this locus, we examined whether inhibition of DNMTs in mutant Htt-expressing primary cortical neurons decreases DNA methylation in the regulatory region of Bdnf exon IV by MeDIP-qPCR. We found that inhibition of DNMTs by decitabine or FdCyd reversed the increase in DNA methylation triggered by mutant Htt (FIG. 4C, FIG. 4E, and FIG. 4F). Consistently, knockdown of either DNMT3A or DNMT1 decreased the levels of DNA methylation in this region (FIG. 4G-H). Together, our results suggest that altered DNA methylation drives the repression of Bdnf transcription in HD neurons and demonstrate that two distinct DNMTs in neurons are both required for the mutant Htt-induced increase in DNA methylation in the Bdnf regulatory region.

Figure 1K:
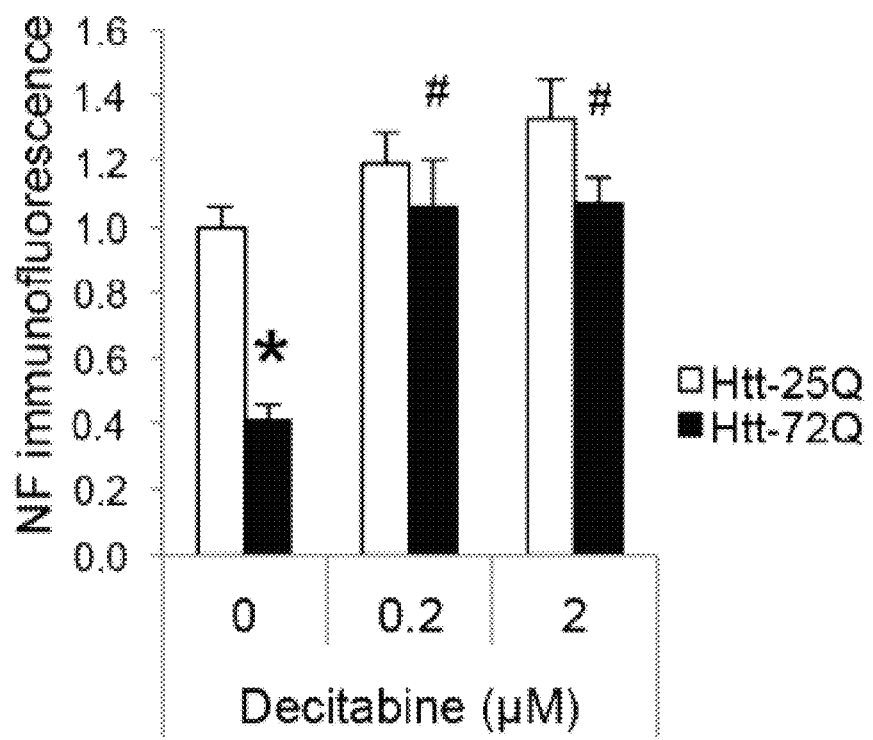
Figure 1L:
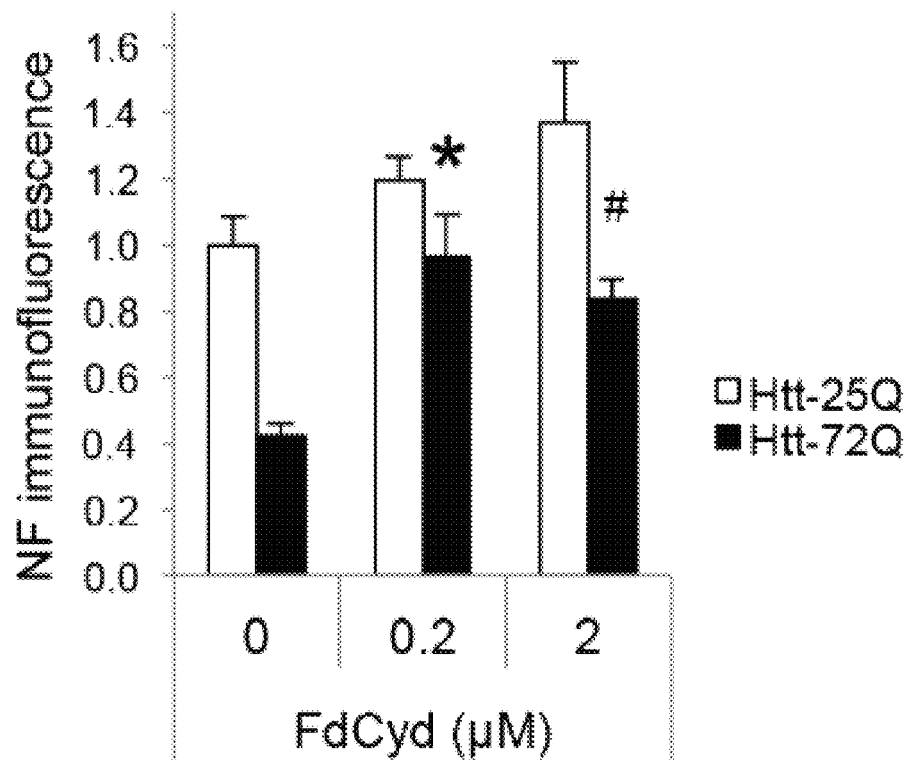
Figure 2A:
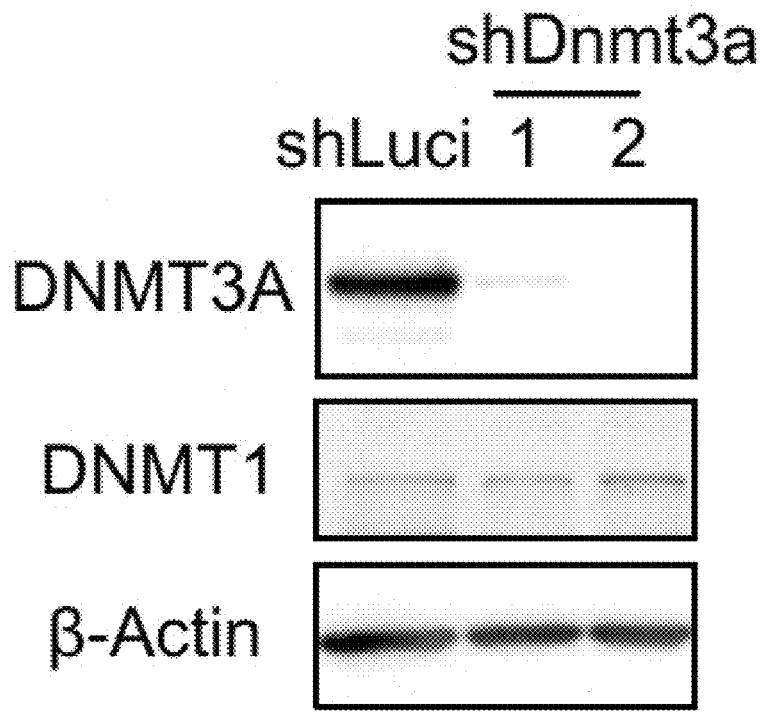
FIG. 2A-2D illustrate that Lentivirus-mediated knockdown of DNMT3A or DNMT1 in primary cortical neurons attenuates mutant Htt-induced toxicity.
Figure 2B:
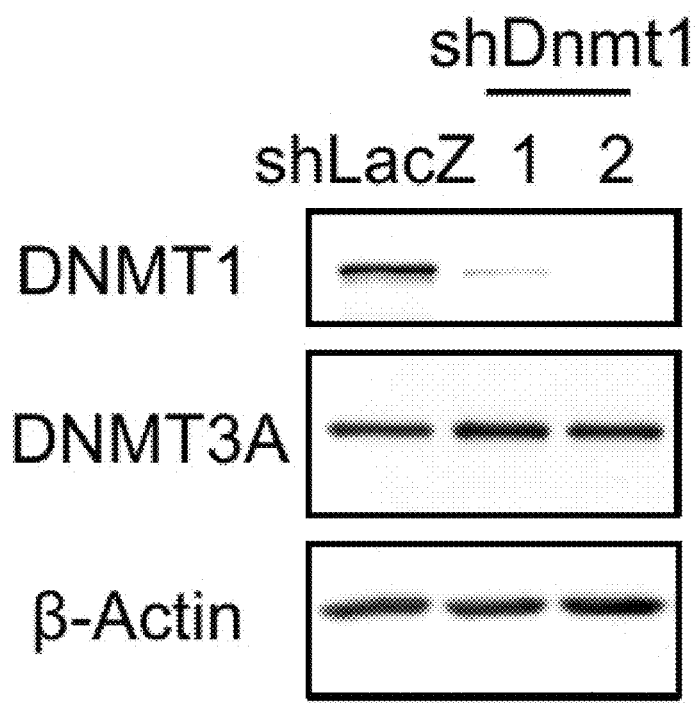
Figure 2C:
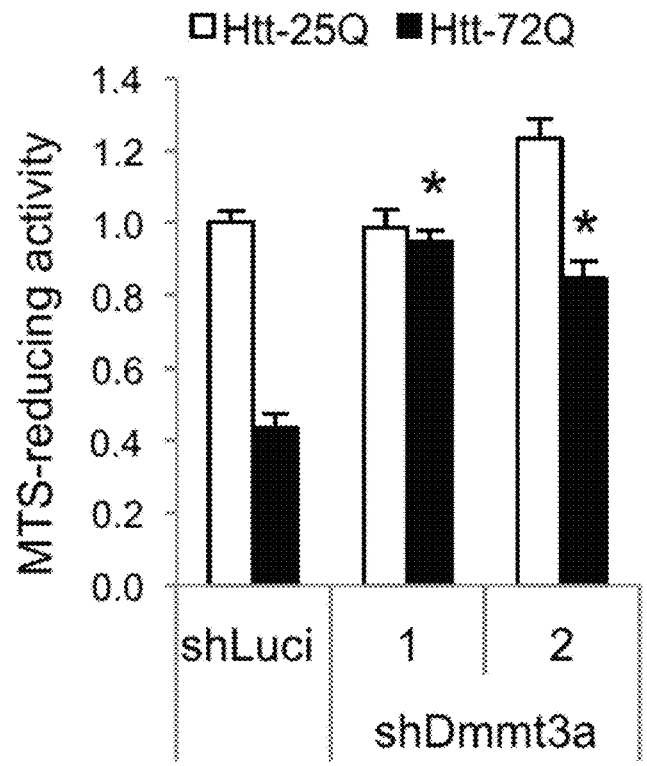
Figure 2D:
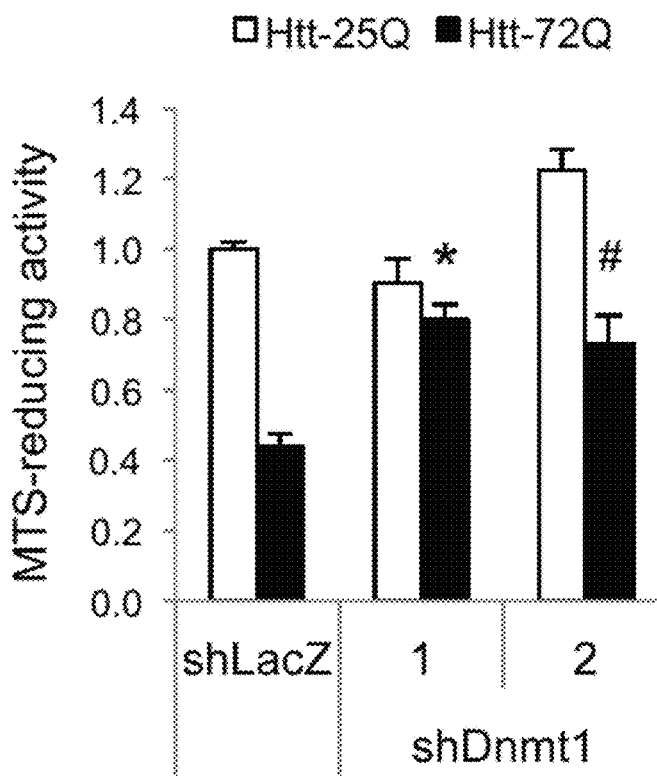
Figure 5A:
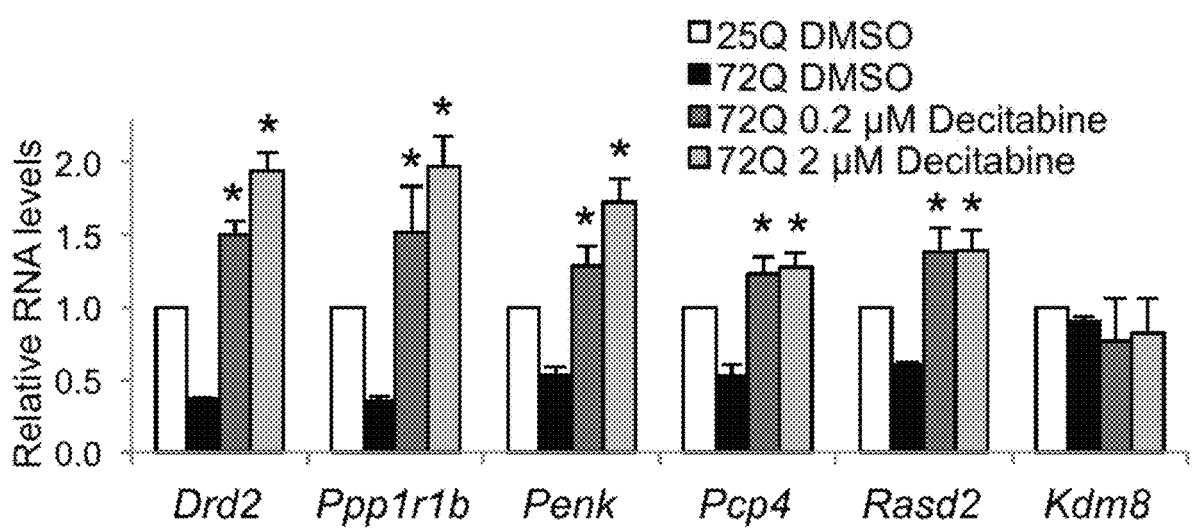
FIG. 5A-5G illustrate that DNMT inhibitors reactivate striatal gene expression in mutant Htt-expressing primary neurons and R6/2 HD mouse brain in vivo.

Example 5. Decitabine Reactivates Expression of Key Striatal Genes in a Primary Striatal Neuron Model of HD Given the neuroprotective effect of decitabine in mutant Htt-expressing striatal neurons (FIG. 1K), we next tested if DNMT inhibition with decitabine restores the expression of other genes that are known to be downregulated in HD. qRT-PCR analyses demonstrated that mutant Htt expression in primary striatal neurons triggers robust changes in gene expression, including downregulation of dopamine receptor D2 (Drd2), protein phosphatase 1, regulatory (inhibitor) subunit 1B (Ppp1r1b, also known as Darpp-32), preproenkephalin (Penk), Purkinje cell protein 4 (Pcp4), and RASD family, member 2 (Rasd2, also known as Rhes) (FIG. 5A). Thus our culture system faithfully reproduces key gene expression changes observed in HD in vivo. These transcriptional changes were detected before mutant Htt neurons exhibit significant neurite degeneration, suggesting that mutant Htt-induced transcriptional changes contribute to striatal neurodegeneration. Inhibition of DNMTs by decitabine dramatically increased the expression of these downregulated transcripts (FIG. 5A). This reactivation of gene expression was specific because the mRNA levels of lysine (K)-specific demethylase 8 (Kdm8) were unchanged by decitabine treatment. Together these results demonstrate that the inhibition of DNA methylation can restore gene expression, which is deficient in HD neurons, suggesting that abnormal DNA methylation plays a critical role in transcriptional dysregulation in HD striatal and cortical neurons.

Figure 5B:
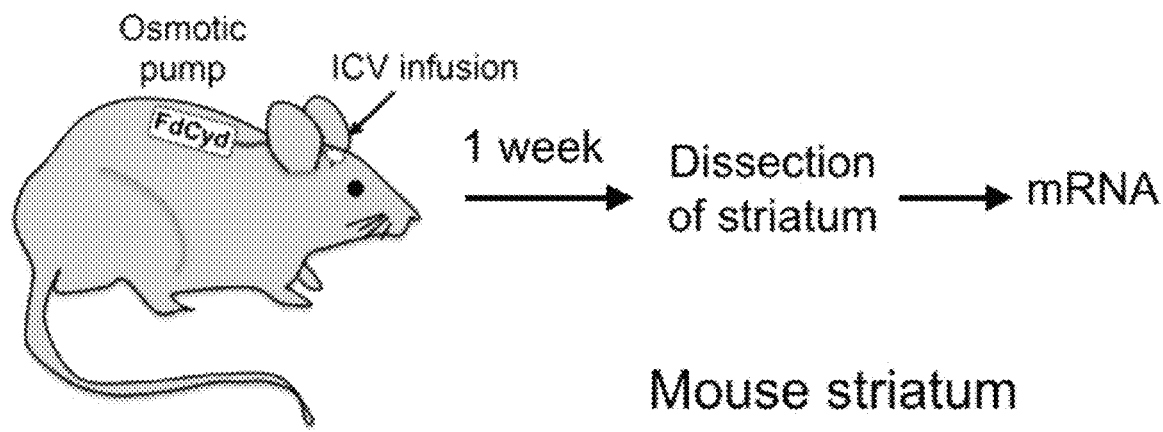
Figure 5C:
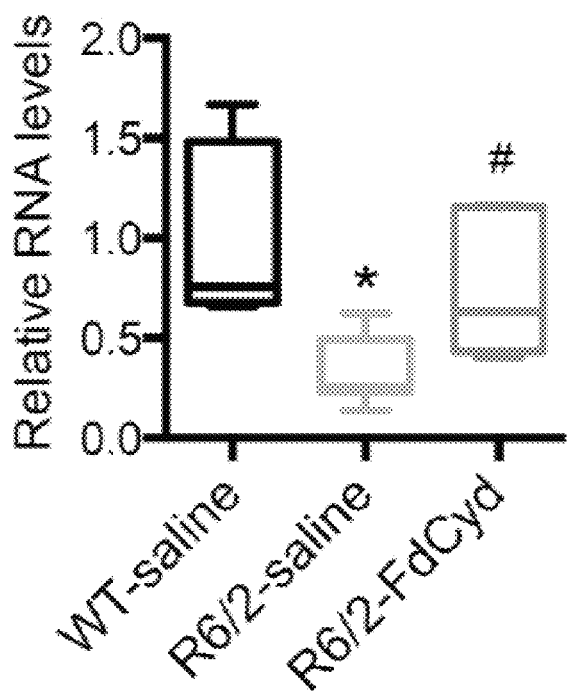
Figure 5D:
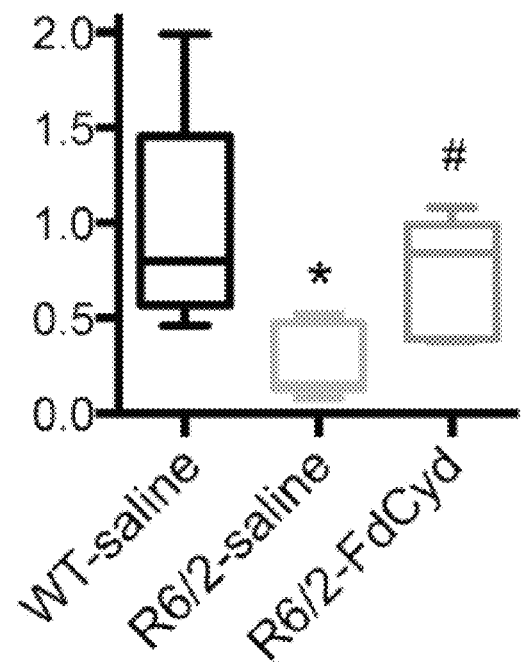
Figure 5E:
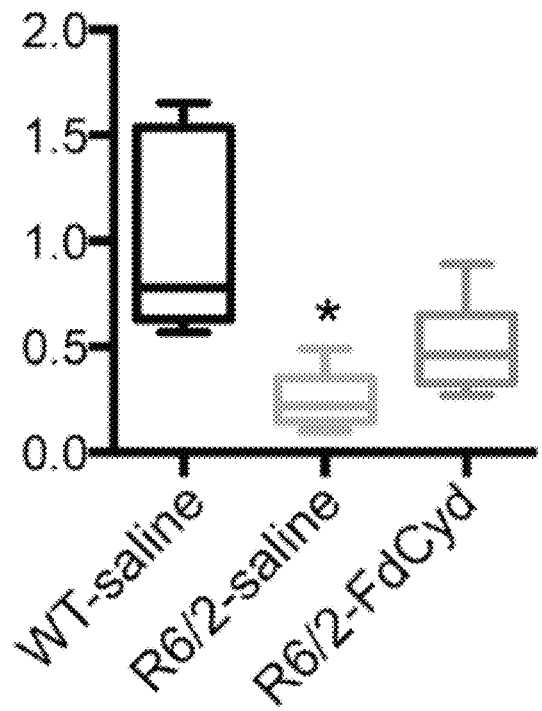
Figure 5F:
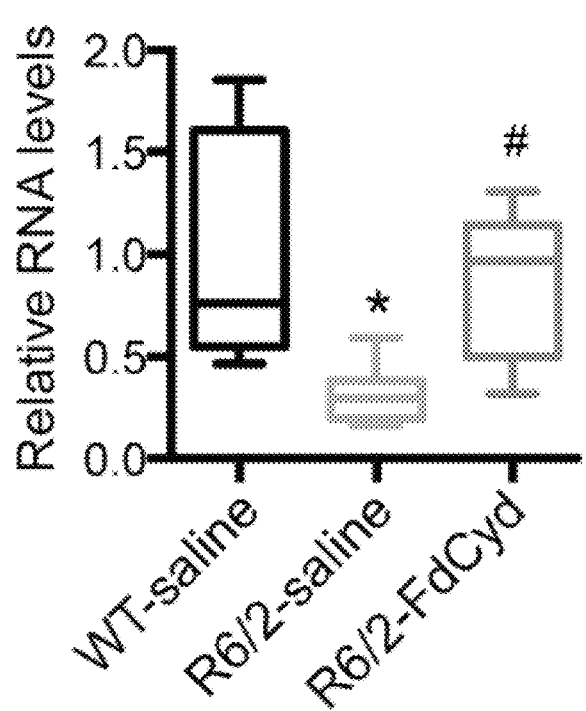
Figure 5G:
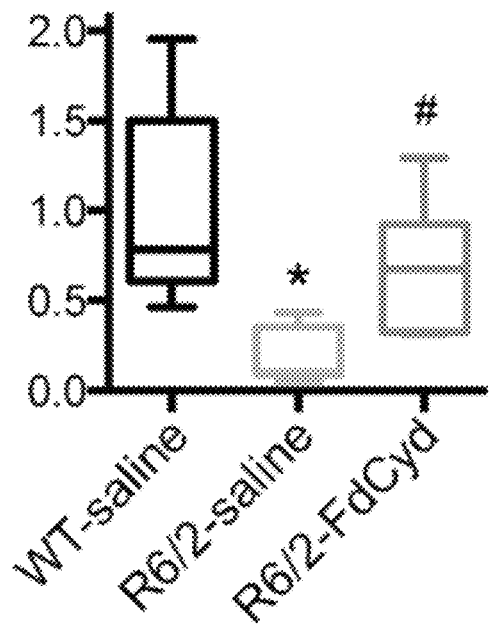
Figure 6:
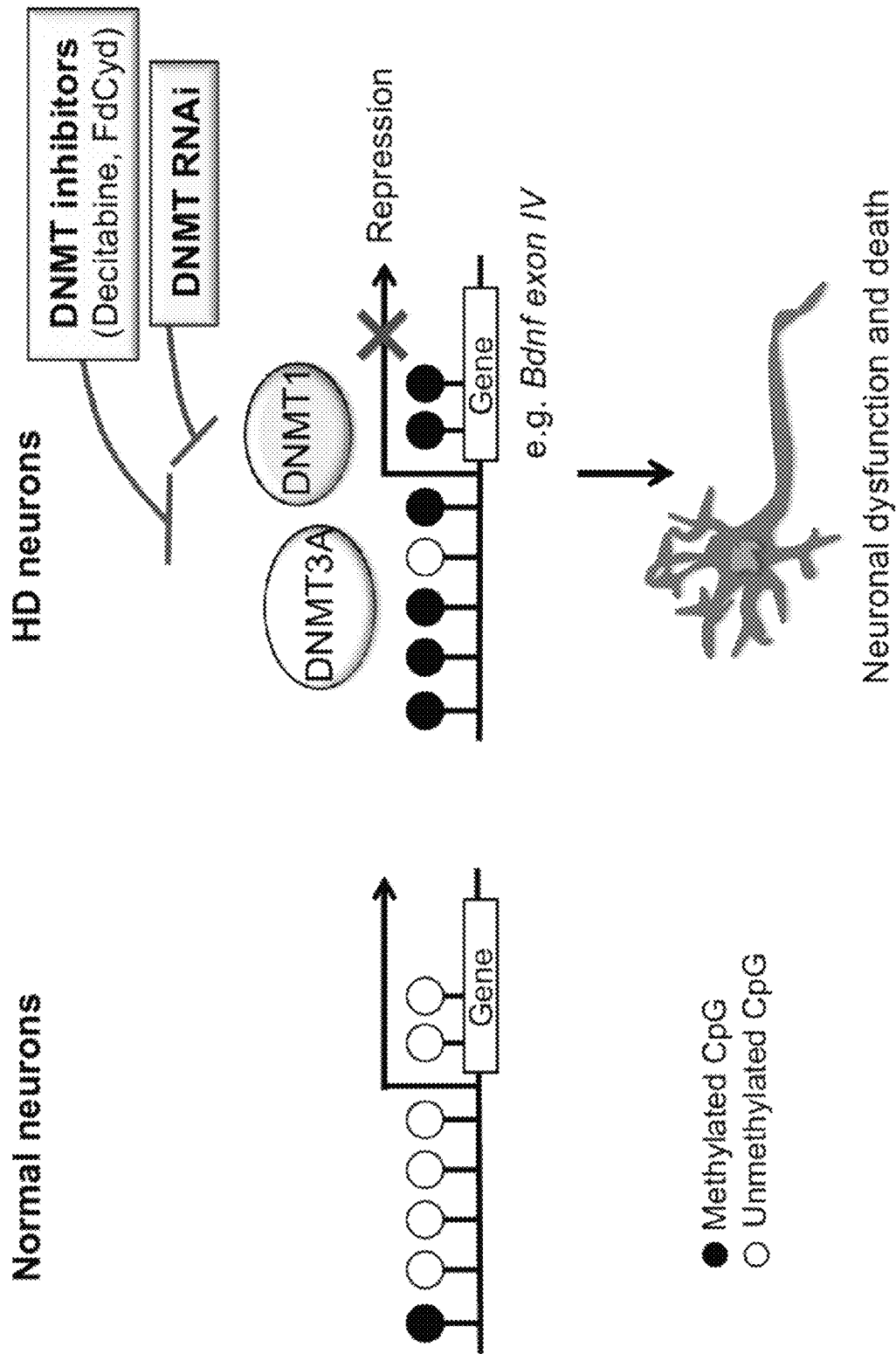
FIG. 6 depicts a model for the role of DNA methylation in HD neurodegeneration. Inhibition of DNMTs in HD neurons by pharmacological inhibitors (decitabine or FdCyd) or RNAi blocks mutant Htt-induced neurotoxicity as well as transcriptional repression of key genes, such as Bdnf, Drd2, Ppp1r1b, and Adora2a. The DNA methylation pathway may thus play an important role in HD neurodegeneration.
Figure 12A:
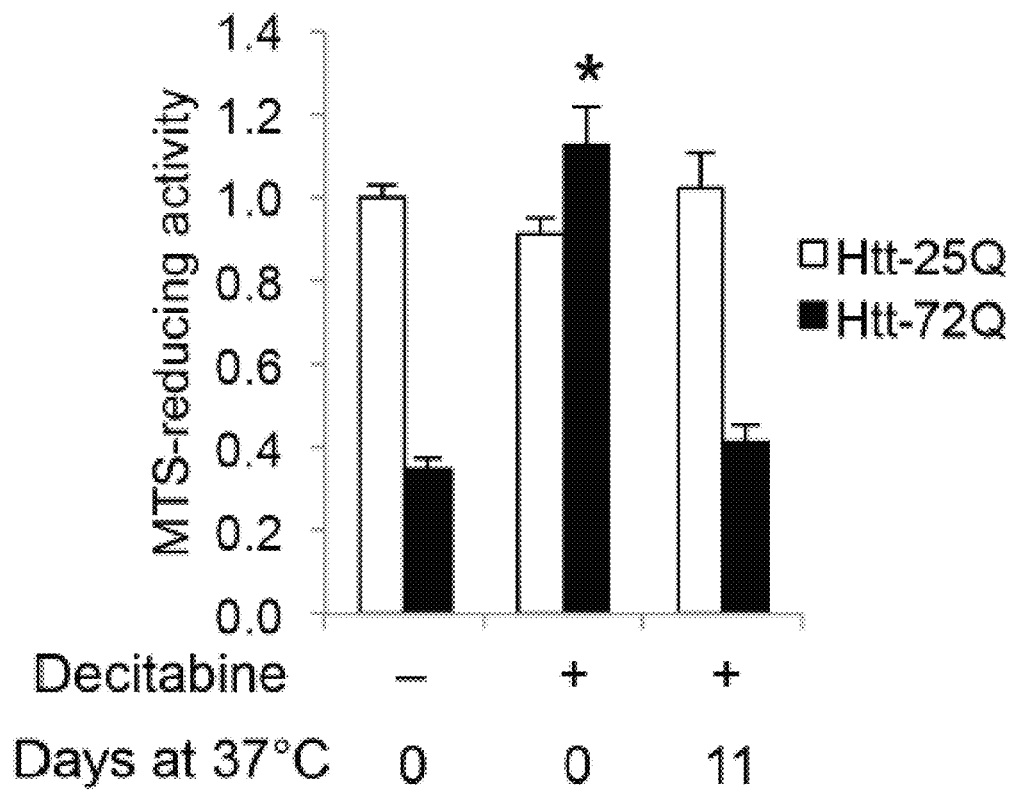
FIG. 12A-B illustrates in vitro stability of decitabine and FdCyd.
Figure 12B:
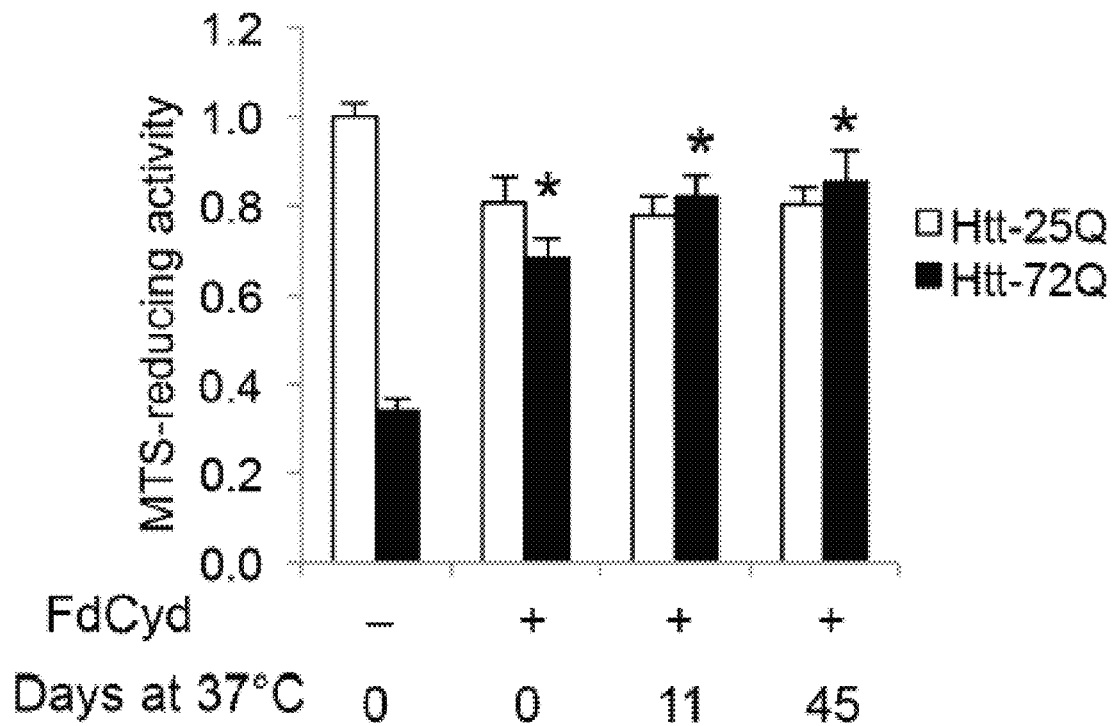

Example 6. Pharmacological Inhibition of DNMTs in HD Mouse Brains Upregulates the Expression of Key Striatal Genes In Vivo We next determined if DNMT inhibition could restore the expression of genes downregulated in HD in vivo using R6/2 HD mouse, a well-characterized transgenic mouse model expressing an N-terminal mutant Htt fragment[60]. This mouse model exhibits robust phenotypes with early disease onset and short life span and recapitulates the altered expression of a number of genes observed in HD patients, including Drd2 and Ppp1r1b in the striatum early in the course of disease progression[12, 60, 61]. Although decitabine has been reported to cross the blood-brain barrier[62, 63], the cytosine nucleoside analog DNMT inhibitors, including decitabine and FdCyd, are known to be degraded rapidly by cytidine deaminase in the liver (in vivo half-life of decitabine <20 min)[62, 64] indicating that systemic administration may not be an effective strategy for drug delivery to the brain. We therefore chose intracerebroventricular (icy) administration using an Alzet osmotic pump, which provides continuous infusion of drug at a consistent rate from a subcutaneous pump (FIG. 5B). Although FdCyd is structurally similar to decitabine, we found that, whereas decitabine lost its in vitro neuroprotective activity after 11 days of pre-incubation at 37° C. in saline, FdCyd fully maintained its neuroprotective activity even after 45 days of pre-incubation (FIG. 12A-B), suggesting that FdCyd is chemically more stable than decitabine at 37° C. in vitro and is better suited for drug delivery with osmotic pumps. The instability of decitabine in vitro has been reported previously[64, 65] We therefore used FdCyd to determine the effect of DNMT inhibition on gene expression in R6/2 brain. One week after the implantation of Alzet osmotic pumps filled with FdCyd or saline in R6/2 mice or WT littermates, RNA was prepared from the striatum (FIG. 5B). Striatal expression of several key mRNAs, Drd2, Ppp1r1b, Rasd2, Adora2a, and Penk mRNAs, was found to be downregulated in HD mouse striatum compared to control animals (FIG. 5B-F), consistent with previous reports in human and mouse HD striata as well as in our HD model striatal neurons (FIG. 5A)[7, 8, 12]. Infusion of FdCyd in R6/2 brains significantly upregulated the expression of striatal Drd2, Ppp1r1b, Rasd2, and Adora2a mRNAs and also showed a trend towards increasing Penk mRNA (FIG. 5B-F), indicating that pharmacological inhibition of DNMTs can correct transcriptional deficiencies in HD mouse brain. Together, these results suggest that DNA methylation plays an important role in transcriptional alterations in HD and potentially, neuronal dysfunction and death in vivo (See a model in FIG. 6).

Discussion for Examples

In this study, we have demonstrated that pharmacological or genetic inhibition of DNMTs substantially attenuates mutant Htt-induced transcriptional dysregulation and neurotoxicity in primary cortical and striatal neurons. We have also provided evidence that aberrant promoter methylation contributes to a reduction in Bdnf expression in mutant Htt-expressing cortical neurons. Given the neuroprotective effects of exogenous BDNF in HD model cortical neurons, blockade of DNMTs may protect neurons from mutant Htt-induced death in part through upregulation of Bdnf gene expression. Remarkably, in vivo experiments demonstrated that treatment of HD mice with DNMT inhibitor FdCyd could reverse the transcriptional repression of key striatal genes in HD mouse brain. Together, we provide evidence that DNA methylation in HD is a critical epigenetic mechanism, which underlies mutant Htt-induced transcriptional alterations and neurodegeneration, raising the possibility that the DNA methylation pathway might represent a new therapeutic target for HD.

Although the causal role of these epigenetic modifications in vulnerable neurons in HD remains unknown, our unbiased drug library screen with 84 chemical compounds, which target known epigenetic pathways, suggests that DNA methylation-mediated gene silencing plays a dominant role in triggering neuronal death.

In primary cortical neuron models, we found that mutant Htt induces increased DNA methylation in the regulatory region of Bdnf exon IV, which is associated with transcriptional repression and a reduction in the transcriptionally active H3K4me3 mark. Additionally, inhibition of DNMTs by pharmacological inhibitors or RNAi could rescue the expression of Bdnf exon IV mRNA in mutant Htt-expressing primary cortical neurons (FIGS. 3D, 3E, and 3G-3I), suggesting that the mutant Htt-triggered increase in DNA methylation in this region directly causes transcriptional repression. Understanding the epigenetic hierarchy downstream of mutant Htt in neurons in relation to RNA expression represents an important future direction.

How mutant Htt promotes DNA methylation at specific Bdnf gene loci at the molecular level remains a significant open question. Possible mechanisms include: 1) mutant Htt expression in neurons increases the levels of DNMT expression, 2) mutant Htt enhances the activity of DNMTs, 3) mutant Htt facilitates the recruitment of the DNA methylation machinery to specific genomic regions, and/or 4)

mutant Htt increases 5-mC levels by decreasing DNA demethylation activity in neurons. The first mechanism, however, is unlikely since we have found that mutant Htt does not significantly increase the mRNA or protein levels of DNMT1 or DNMT3A in primary cortical neurons. The second and third mechanisms are reasonable possibilities and may be caused by aberrant protein-protein interactions and/or abnormal posttranslational modifications of DNMTs downstream of mutant Htt. Regarding the fourth possible mechanism, whether mutant Htt increases 5-mC levels on repressed genes by inhibiting the DNA demethylation pathway in HD is an interesting question.

We focused on Bdnf as a model gene to test the hypothesis that mutant Htt represses neuronal gene expression through promoter hypermethylation. Our results show that mutant Htt expression increases cytosine methylation in the regulatory region of Bdnf exon IV and that inhibition of DNMTs reactivate exon IV transcription, supporting the idea that increased DNA methylation plays a causal role in repression of Bdnf transcription in HD. In contrast, the regulatory region of Bdnf exon VI, appears not to be directly regulated by DNA methylation, suggesting instead that indirect mechanisms are initiated by aberrant DNA methylation in the control of the Bdnf exon VI repression. Our results suggest that manipulation of DNA methylation may offer a new therapeutic approach to increase neuronal BDNF expression in HD brain.

The reduction of either DNMT1 or DNMT3A by RNAi is sufficient to block transcriptional changes and neuronal death induced by mutant Htt (FIGS. 2A-2D, 3G, and 3H), suggesting that both DNMTs are required to exert mutant Htt-mediated toxicity. Although in dividing cells, the roles of DNMT1 and DNMT3A as maintenance and de novo DNMTs, respectively, are known, the specific roles of the two DNMTs in postmitotic neurons remain undefined, necessitating exploration in future studies. Targeting either DNMT1 or DNMT3A in adult neurons may attenuate mutant Htt-induced neurotoxicity with minimal side effects in regard to normal synaptic functions in the brain. It has been demonstrated that the nucleoside analog DNMT inhibitors, such as decitabine and FdCyd, must first be incorporated into DNA to exert their DNMT inhibitory activity[46, 65, 84]. In dividing cells, drug incorporation occurs during DNA synthesis. The mechanism of action of these DNMT inhibitors in non-dividing postmitotic neurons, however, still remains unclear, although it is possible that the base excision repair pathway contributes to the incorporation of nucleoside-analog DNMT inhibitors. Improved molecular understanding of the action of decitabine and FdCyd may identify potential "hot spots" of incorporation in the neuronal genome, providing relevant information regarding specific gene targets undergoing active methylation in the HD epigenome. Integrating genome-wide DNA methylation and transcriptional changes associated with DNMT inhibition in future studies will identify the key gene targets of DNMT inhibition-induced demethylation in HD neurons.

Finally, the findings from the current study immediately suggest that inhibition of DNMTs might ameliorate HD phenotypes in vivo, which will be the subject of important future experiments. Improved understanding of the epigenetic gene regulation in HD neurons will provide important foundational knowledge for the development of therapeutic strategies targeting DNA methylation abnormalities in HD.

METHODS FOR EXAMPLES

Antibodies and Reagents

Mouse monoclonal anti-neurofilament (NF) (165 kDa) (clone 2H3, Developmental Studies Hybridoma Bank) was used for immunofluorescence. Mouse monoclonal anti-β-actin (sc-47778, Santa Cruz Biotechnology), rabbit monoclonal anti-DNMT1 (D63A6, Cell Signaling Technology, Inc.), and rabbit polyclonal anti-DNMT3A (sc-20703, Santa Cruz Biotechnology) antibodies were used for immunoblotting. Mouse monoclonal anti-Htt (EM48) antibody[85] (MAB5374, Millipore) was used for immunofluorescence and immunoblotting. Decitabine was purchased from Cayman Chemical (11166) and LC laboratories (D-3899). 5'fluoro-2'deoxycytidine (FdCyd) was purchased from Sigma (F5307) and Santa Cruz Biotechnology (sc-252267). These drugs were confirmed to exhibit similar effects regardless of the source.

Plasmids

Lentiviral expression plasmids containing Htt exon1-25Q (Htt-25Q) and Htt exon1-72Q (Htt-72Q) constructs under the control of the mouse PGK (Pgk1) promoter (mPGK-Httex1-25Q and mPGK-Httex1-72Q) were kindly provided by D. Krainc (Harvard Medical School, Boston, Mass.) (Northwestern University, Chicago, Ill.). Lentivirus-based Dnmt3a RNAi and Dnmt1 RNAi constructs (pLKO.1-puro), developed at the Broad Institute of MIT and Harvard, were obtained (Sigma-Aldrich). The oligo sequences in the shRNA vectors targeted Dnmt3a and Dnmt1 are as follows:

pLKO.1-Dnmt3a#1 (TRCN0000039034):
(SEQ ID NO: 1)
CCGGCCAGATGTTCTTTGCCAATAACTCGAGTTATTGGCAAAGAACATCT
GGTTTTTG;

pLKO.1-Dnmt3a#2 (TRCN0000039035):
(SEQ ID NO: 2)
CCGGGCAGACCAACATCGAATCCATCTCGAGATGGATTCGATGTTGGTCT
GCTTTTTG;

pLKO.1-Dnmt1#1 (TRCN0000219081):
(SEQ ID NO: 3)
GTACCGGATCTATGGAAGGTGGTATTAACTCGAGTTAATACCACCTTCCA
TAGATTTTTTG;

pLKO.1-Dnmt1#2 (TRCN0000225698):
(SEQ ID NO: 4)
CCGGTATATGAAGACCTGATCAATACTCGAGTATTGATCAGGTCTTCATA
TATTTTTG.

Primary Neuron Cultures, Lentiviral Transduction Drug Treatments

Mouse primary cortical and striatal neurons from embryonic day (E) 15.5 Swiss Webster mouse fetuses (Taconic) were first plated in the minimal essential medium (MEM) containing 10% FBS, 0.45% glucose, 1 mM sodium pyruvate, 2 mM glutamine, 20 U/ml penicillin and 20 µg/ml streptomycin, for 3 h and then maintained in serum-free Neurobasal medium (Life Technologies) containing NeuroCult™ SM1 neuronal supplement (STEMCELL Technologies), 0.5 mM glutamine and 25 µM glutamate for the first 3 d in a humidified incubator (37° C. in 5% $CO_2$). Half of the medium was replaced with Neurobasal medium with SM1 and 0.5 mM glutamine every 3 days. Primary cortical neurons plated on 96-well flat clear bottom black plates (Corning #3904) at $4\times10^4$ cells/well were infected with Htt exon1 expression lentivirus (Htt-25Q or Htt-72Q) or control empty vector lentivirus at 5 days in vitro (DIV 5). Primary striatal neurons plated on 96-well plates at $1\times10^5$ cells/well were infected with Htt exon1 expression lentivirus at DIV 4. Viral copy number was adjusted for transduction of neurons on the basis of titer measured using the Lenti-X qRT-PCR titration kit (Clontech), and equal numbers of viral particles of Htt-25Q and Htt-72Q expressing lentiviruses were used for transduction. For the experiments to test effects of DNMT inhibitors, neurons were treated with inhibitors six hours after Htt lentiviral infection. One half of the media was changed every 3 days with media containing new drug. In knockdown experiments in Htt-expressing neurons, primary cortical neurons were cotransduced with Htt-expressing lentivirus and Dnmt shRNA or control shRNA lentivirus at DIV 5. pLKO.1-TRC1-luciferase (Luci) and pLKO.1-TRC2-LacZ were used as control for RNAi with pLKO.1-TRC1-Dnmt3a and pLKO.1-TRC2-Dnmt1, respectively. Lentiviral particles were prepared by transfecting 293LE cells with the lentiviral plasmid of interest along with packaging plasmid psPAX2 and envelope plasmid pCMV-SVG as described previously[86]. Four days after transfection, viruses in the conditioned media were collected and purified using Lenti-X Concentrator (Clontech). Primary cortical neurons from BACHD mouse embryos (E15.5) were individually plated into separate wells and treated at DIV 4 with decitabine or vehicle for 3.5 days.

Measurements of Cell Viability/Cytotoxicity and in Primary Neurons

Primary cortical neurons grown in a 96-well plate were transduced with Htt-expressing lentiviruses at DIV 5 and assessed for mitochondrial metabolic activity at 9 days post-infection (DIV 14) using 3-(4,5-dimethylthiazol-2-yl)-5-(3-carboxymethoxyphenyl)-2-(4-sulfophenyl)-2H-tetrazolium (MTS) (Promega) per manufacturer's instructions. MTS-reducing activity was normalized for each condition to Htt-25Q lentiviruses treated with vehicle or cotransduced with control RNAi lentivirus (=1). Experiments were performed in 3 or more wells per experiment in three to five independent experiments.

For the measurement of neurofilament (NF) immunofluorescence intensity, cortical and striatal neurons cultured in a 96-well plate were fixed in 4% paraformaldehyde (PFA) in PBS for 20 min nine and seven days after Htt lentiviral infection, respectively, permeabilized with 0.1% Triton X-100 in PBS for 15 min at room temperature, and subjected to indirect immunofluorescence with anti-NF (2H3) primary antibody and Alexa Fluor 568-conjugated goat anti-mouse IgG secondary antibody (Life Technologies). Images of Alexa Fluor 568 and bright field were captured (nine random fields per well) using an Operetta high-content imaging system (PerkinElmer) with a 20× objective lens. Following image background subtraction, the NF immunofluorescence intensity was quantified using an ImageJ-based macro. Image capture and quantification of Htt (EM48) immunofluorescence intensity were performed as described for those of NF. In this quantification analysis, we confirmed that the number of cells in a cultured well are similar among mutant Htt-expressing neurons with or without DNMT inhibitor treatment, by counting the number of nuclei in the images used for quantification: Htt-72Q neurons treated with vehicle (299±7.8 cells), decitabine (299±4.6 cells), n=18 wells from 6 independent experiments, and therefore the data reflect EM48 intensity per cell. For the quantification of cell death, primary cortical neurons grown in a 96-well plate were infected with Htt lentivirus at DIV 5 and fixed nine days after infection as described above. Cell nuclei were labeled with Hoechst 33342 (Life Technologies), and neurons were assessed in a blinded fashion for cell death by scoring condensed or fragmented nuclei. Experiments were performed in 4 to 6 wells per experiment in three independent experiments. About 300 nuclei from three random fields in a well were counted.

Drug Library Screen

Epigenetic drug screen was performed using a primary cortical neuron model of HD with a drug library composed of 84 compounds (Table 1), among which 80 drugs are purchased from Cayman Chemical (Epigenetic Screening Library Item No 11076) and four drugs, SGC0946, EPZ5676, EPZ6438, and GSK126, were obtained from Xcessbio Biosciences Inc. Mouse primary cortical neurons were plated on 96-well flat clear bottom black plates (Corning #3904). WT or mutant Htt exon1 fragment (Htt-25Q or Htt-72Q)-expressing lentiviruses are infected at DIV 5 as described above. The 84 compounds were added to the media at DIV 6 one day after Htt lentiviral infection with three different doses (0.02, 0.2, 2 µM) for each compound at triplicates. DMSO was used as control. Media containing compounds or DMSO were changed every three days to maintain the compounds' activity. At DIV 14, the viability of neurons was determined by resazurin (Alamar blue) assay, a quantitative measurement of mitochondrial metabolic activity. The screen was fully automated and performed in the High-Throughput Screening Center in Washington University School of Medicine. Any possible plate effects were determined using control plates treated with DMSO and used for normalization. Screen hits were validated by MTS assay.

TABLE 1

| | | |
|---|---|---|
| 1 | CAY10433 | HDAC inhibitor |
| 2 | Piceatannol | Resveratrol analog |
| 3 | CAY10591 | SIRT1 activator |
| 4 | EX-527 | SIRT1 inhibitor |
| 5 | SAHA | Calss I and II HDAC inhibitor |
| 6 | 2-PCPA (hydrochloride) | LSD1 inhibitor |
| 7 | 3-amino Benzamide | PARP inhibitor |
| 8 | SB 939 | HDAC inhibitor |
| 9 | PCI 34051 | HDAC8 inhibitor |
| 10 | 4-iodo-SAHA | ClassI and II HDAC inhibitor (SAHA derivative) |
| 11 | Sirtinol | SIRT inhibitor |
| 12 | C646 | HAT p300 inhibitor |
| 13 | Tubastatin A (tri-fluoroacetate salt) | HDAC6 inhibitor |
| 14 | Garcinol | p300 and PCAF HAT inhibitor |
| 15 | Ellagic Acid | Antioxidant; inhibitor of H3R17 methylation |
| 16 | Suberohydroxamic Acid (SBHA) | HDAC inhibitor |
| 17 | Apicidin | HDAC inhibitor |
| 18 | UNC0321 (trifluoro-acetate salt) | G9a HMTase inhibitor |
| 19 | (−)-Neplanocin A | SAH hydrolase inhibitor (SAM-dependent MT inhibitor) |
| 20 | Cl-Amidine | PAD4 deiminase inhibitor |
| 21 | F-Amidine (tri-fluoroacetate salt) | PAD4 deiminase inhibitor |
| 22 | JGB1741 | SIRT1 inhibitor |
| 23 | UNC0638 | G9a HMTase inhibitor |
| 24 | Isoliquiritigenin | Antioxidant, anti-inflammatory, antitumor activities |
| 25 | CCG-100602 | Inhibitor of Rho pathway-mediated signaling and activation of serum response factor transcription |
| 26 | CAY10669 | pCAF (p300/CREB-binding protein-associated factor) HAT inhibitor |
| 27 | Zebularine | DNMT inhibitor |
| 28 | Delphinidin chloride | p300/CBP HAT inhibitor |
| 29 | Suramin (sodium salt) | SIRT1 inhibitor |
| 30 | Nicotinamide | SIRT inhibitor |
| 31 | 2,4-Pyridinedi-carboxylic Acid | Histone demethylase inhibitor |
| 32 | PFI-1 | BET bromodomain inhibitor |

TABLE 1-continued

| | | |
|---|---|---|
| 33 | 5-Azacytidine | DNMT inhibitor |
| 34 | Decitabine | DNMT inhibitor |
| 35 | (+)-JQ1 | BET bromodomain inhibitor |
| 36 | (−)-JQ1 | Negative control for (+)-JQ1 |
| 37 | BSI-201 | PARP1 inhibitor |
| 38 | 1-Naphthoic Acid | SIRT inhibitor |
| 39 | AG-014699 | PARP-1 inhibitor |
| 40 | IOX1 | inhibitor of 2-oxoglutarate oxygenases |
| 41 | MI-2 (hydrochloride) | Inhibitor of the menin-MLL fusion protein interaction |
| 42 | MI-nc (hydrochloride) | Weak inhibitor of the menin-MLL fusion protein interaction; negative control for MI-2 |
| 43 | Lomeguatrib | $O^6$-Methylguanine-DNA methyl-transferase (MGMT) inhibitor |
| 44 | Daminozide | Inhibitor of the human 2-oxoglutarate (JmjC) histone demethylases, KDM2A, PHF8, and KDM7A |
| 45 | GSK-J1 (sodium salt) | JMJD3 selective histone demethylase inhibitor |
| 46 | GSK-J2 (sodium salt) | Poor JMJD3 inhibitor (negative control) |
| 47 | GSK-J4 (hydrochloride) | JMJD3 selective histone demethylase inhibitor |
| 48 | GSK-J5 (hydrochloride) | Weak JMJD3 demethylase inhibitor (inactive control) |
| 49 | Valproic Acid (sodium salt) | HDAC inhibitor |
| 50 | Tenovin-1 | p53 activator; SIRT1 and SIRT2 inhibitor |
| 51 | Tenovin-6 | p53 activator; SIRT1, SIRT2, and SIRT3 inhibitor |
| 52 | Sodium Butyrate | HDAC inhibitor |
| 53 | Anacardic Acid | HAT (p300 and pCAF) inhibitor; anti-inflammatory, anti-tumor, molluscicidal, and anti-microbial activity |
| 54 | AGK2 | SIRT2 inhibitor |
| 55 | CAY10603 | HDAC6 inhibitor |
| 56 | Chaetocin | HMT inhibitor with selectivity for Lys9-HMTs (SU(VAR)3-9, G9a, DIM5) |
| 57 | Splitomicin | Sir2p HDAC inhibitor |
| 58 | CBHA | HDAC inhibitor, |
| 59 | M 344 | HDAC inhibitor |
| 60 | Oxamflatin | HDAC inhibitor |
| 61 | Salermide | SIRT1 and SIRT2 inhibitor |
| 62 | Mirin | Mre11-Rad50-Nbs1 (MRN) inhibitor |
| 63 | Pimelic Diphenylamide 106 | Calss I HDAC inhibitor |
| 64 | (S)-HDAC-42 | HDAC inhibitor |
| 65 | MS-275 | HDAC (HDAC1) inhibitor |
| 66 | RG-108 | DNMT inhibitor |
| 67 | 2′,3′,5′-triacetyl-5-Azacytidine | DNMT inhibitor |
| 68 | S-Adenosylhomo-cysteine (SAH) | Product of SAM-dependent methylation of DNA, RNA, and histones and other proteins |
| 69 | UNC0224 | G9a HMTase inhibitor |
| 70 | Chidamide | HDAC inhibitor |
| 71 | 3-Deazaneplanocin A | S-adenosyl-L-homocysteine hydrolase inhibitor; EZH2 inhibitor |
| 72 | Sinefungin | SET domain-containing methyltransferase inhibitor |
| 73 | N-Oxalylglycine | Inhibitor of α-ketoglutarate-dependent enzymes and prolyl hydroxylase domain-containing proteins PHD1 and PHD2 |
| 74 | AMI-1 (sodium salt) | PRMTs inhibitor |
| 75 | UNC1215 | L3MBTL3 domain inhibitor |
| 76 | trans-Resveratrol | Antioxidant, antiproliferative and anti-inflammatory activity, and cyclooxygenase-1 inhibitor |
| 77 | 2,4-DPD | HIF-PH inhibitor |
| 78 | DMOG | HIF-PH inhibitor |
| 79 | Trichostatin A | HDAC inhibitor |
| 80 | CAY10398 | HDAC1 inhibitor |
| 81 | SGC0946 | DOT1L inhibitor |
| 82 | EPZ5676 | DOT1L inhibitor |
| 83 | EPZ6438 | EZH2 inhibitor |
| 84 | GSK126 | EZH2 inhibitor |

1-80: Epigenetic Screening Library from Cayman Chemical (Item Number 11076)
81-84: Xcessbio Biosciences Inc.

HD Transgenic Mice and Drug Administration

R6/2 mice, which carry the promoter sequence and exon 1 of a mutant human HTT gene, were obtained from JAX (Stock No: 002810) (Bar Harbor, Me.), and a colony was maintained by breeding R6/2 males with B6CBAF1 females (JAX). PCR genotyping was performed using a primer set (CGGCTGAGGCAGCAGCGGCTGT (SEQ. ID NO:5) and GCAGCAGCAGCAGCAACAGCCGCCACCGCC(SEQ ID NO:6)) as described [Mangiarini, L. et al. 1996 Cell]. To maintain mice carrying the same number of CAG repeats, a second PCR analysis was also conducted using a primer set amplifying across the CAG repeats (ATGAAGGCCTTC-GAGTCCCTCAAGTCCTTC (SEQ ID NO: 7) and GGCG-GCTGAGGAAGCTGAGGA (SEQ ID NO: 8)). BACHD mice on the C57BL6/J background, which were generated by the laboratory of X. William Yang (University of California, Los Angeles)[53, 87], were obtained from the CHDI Foundation. All live vertebrate experiments were performed in compliance with the US National Institutes of Health Guide for the Care and Use of Laboratory Animals. Animal protocols were approved by the Institutional Animal Care and Use Committees of Washington University. To determine the effect of DNMT inhibitor on gene expression in HD mouse brain in vivo, FdCyd (0.1 mM in saline) was directly administered into 6 week-old R6/2 mice and control littermates by stereotactic intracerebroventricular (icy) infusion using Alzet mini-osmotic pump (DURET Corporation, MODEL 2001; 1.0 μl/h, 7 days) and the brain infusion kit 3 (DURET Corporation, #0008851). Saline was used as control. One week later, the striatum was dissected and processed for qRT-PCR analysis. The CAG repeat length of R6/2 mice used for the in vivo gene expression analysis was determined by Laragen Inc. (Culver City, Calif.) using tail DNA and was approximately 200.

Quantitative Reverse Transcription PCR (qRT-PCR)

RNAs were isolated from cultured neurons 5 days after infection of Htt lentiviruses and mouse brain using the RNeasy Plus Mini Kit (QIAGEN) and RNeasy Plus Universal Mini Kit (QIAGEN), respectively. Reverse transcription was performed with High-Capacity cDNA Reverse Transcription Kit (Applied Biosystems). qPCR was performed using Power SYBR Green PCR Master Mix (Applied Biosystems) on CFX Connect Real-Time System (Bio-Rad). β-actin and hypoxanthine phosphoribosyltransferase I (Hprt), and/or 18S rRNA were used as reference genes for data normalization unless otherwise stated. Relative mRNA levels were calculated using the ΔΔCq method. Sequences of the primers used for qRT-PCR analysis are listed in Table 2 (SEQ ID NOs: 9-46).

TABLE 2

| SEQ ID NO | Name | Sequence |
|---|---|---|
| 9 | Dnmt3a mRNA analysis Forward Primer | AATAGAGACCCTCGGAGGCA |
| 10 | Dnmt3a mRNA analysis Reverse Primer | CCTGCTGCTAGTTGGGTTCT |
| 11 | Dnmt1 mRNA analysis Forward Primer | AACAGCTCCAGCCCGAGT |
| 12 | Dnmt1 mRNA analysis Reverse Primer | TTTTCTGTTAAGCCATCTCTTTCC |

TABLE 2-continued

| SEQ ID NO | Name | Sequence |
|---|---|---|
| 13 | Bdnf exon IX (protein coding) mRNA analysis Forward Primer | GACAAGGCAACTTGGCCTAC |
| 14 | Bdnf exon IX (protein coding) mRNA analysis Reverse Primer | CGTGCTCAAAAGTGTCAGCC |
| 15 | Bdnf exon I mRNA analysis Forward Primer | CCTGCATCTGTTGGGGAGAC |
| 16 | Bdnf exon I mRNA analysis Reverse Primer | GCCTTGTCCGTGGACGTTTA |
| 17 | Bdnf exon II mRNA analysis Forward Primer | CTAGCCACCGGGGTGGTGTAA |
| 18 | Bdnf exon II mRNA analysis Reverse Primer | CGCCTTCATGCAACCGAAGT |
| 19 | Bdnf exon III mRNA analysis Forward Primer | GCTTCATTGAGCCCAGTTCC |
| 20 | Bdnf exon III mRNA analysis Reverse Primer | GCCTTGTCCGTGGACGTTTA |
| 21 | Bdnf exon IV mRNA analysis Forward Primer | CAGAGCAGCTGCCTTGATGTT |
| 22 | Bdnf exon IV mRNA analysis Reverse Primer | GCCTTGTCCGTGGACGTTTA |
| 23 | Bdnf exon VI mRNA analysis Forward Primer | TTGGGGCAGACGAGAAAGCGC |
| 24 | Bdnf exon VI mRNA analysis Reverse Primer | AGGATGGTCATCACTCTTCTC |
| 25 | 18s mRNA analysis Forward Primer | AGTCGGCATCGTTTATGGTC |
| 26 | 18s mRNA analysis Reverse Primer | CGAAAGCATTTGCCAAGAAT |
| 27 | Hprt mRNA analysis Forward Primer | TTGACACTGGTAAAACAATGCAAAC |
| 28 | Hprt mRNA analysis Reverse Primer | GAGAGGTCCTTTTCACCAGCA |
| 29 | β-actin (Actb) mRNA analysis Forward Primer | AGTGTGACGTTGACATCCGTA |
| 30 | β-actin (Actb) mRNA analysis Reverse Primer | GCCAGAGCAGTAATCTCCTTCT |
| 31 | Drd2 mRNA analysis Forward Primer | CTGGAGCCAAAAGCAGTCTG |
| 32 | Drd2 mRNA analysis Reverse Primer | TCCTTCAGGTTTCCGACGCC |
| 33 | Ppp1r1b mRNA analysis Forward Primer | CCAACCCCTGCCATGCTTT |
| 34 | Ppp1r1b mRNA analysis Reverse Primer | TTGGGTCTCTTCGACTTTGGG |
| 35 | Penk mRNA analysis Forward Primer | TGGCGTAGGGCCTGCGTC |
| 36 | Penk mRNA analysis Reverse Primer | TGTAAAGCGGCCGCGTCG |
| 37 | Pcp4 mRNA analysis Forward Primer | CGACCAACGGAAAAGACAAG |
| 38 | Pcp4 mRNA analysis Reverse Primer | TGTCTCTGGTGCATCCATGT |
| 39 | Rasd2 mRNA analysis Forward Primer | AACTGCGCCTACTTCGAGG |
| 40 | Rasd2 mRNA analysis Reverse Primer | GGTGAAAAGCATCGCCGTACT |
| 41 | Kdm8 mRNA analysis Forward Primer | GCTGGACCTCGGTGAGAAG |
| 42 | Kdm8 mRNA analysis Reverse Primer | TCCCAGGAGTAGTCTAGGACG |
| 43 | Adora2A mRNA analysis Forward Primer | GCCATCCCATTCGCCATCA |
| 44 | Adora2A mRNA analysis Reverse Primer | GCAATAGCCAAGAGGCTGAAGA |
| 45 | human HTT exon1 mRNA analysis Forward Primer | TCAACCTCCTCCACAGGCAC |
| 46 | human HTT exon1 mRNA analysis Reverse Primer | AGGCTCCTCAGCCACAGCT |
| 47 | Bdnf IV bisulfite sequencing analysis Forward Primer | GTGAATTTGTTAGGATTGGAAGTGA AAATA |
| 48 | Bdnf IV bisulfite sequencing analysis Reverse Primer | CTAAACAAAAACTAAAAAATTTCAT ACTAACTC |
| 49 | Bdnf VI bisulfite sequencing analysis Forward Primer | GGTAGGTATAGAGTTTTGGGTTTAA GTAG |
| 50 | Bdnf VI bisulfite sequencing analysis Reverse Primer | ACACTAAAATCAAACATTATTTAAC TCTTC |
| 51 | Bdnf IV MeDIP analysis Forward Primer | GCGCGGAATTCTGATTCTGGTA |
| 52 | Bdnf IV MeDIP analysis Reverse Primer | CTGCCTTGACGTGAGCTGTC |
| 53 | Gapdh MeDIP analysis Forward Primer | CTCTGCTCCTCCCTGTTCC |

TABLE 2-continued

| SEQ ID NO | Name | Sequence |
|---|---|---|
| 54 | Gapdh MeDIP analysis Reverse Primer | TCCCTAGACCCGTACAGTGC |
| 55 | Bdnf IV Chip analysis Forward Primer | CTTCTGTGTGCGTGAATTTGCT |
| 56 | Bdnf IV Chip analysis Reverse Primer | AGTCCACGAGAGGGCTCCA |

Bisulfite Conversion and Sequencing

Genomic DNA was extracted from cells using QIAamp DNA Mini Kit (QIAGEN) and subjected to bisulfite conversion using EZ DNA Methylation-Lightning™ Kit (Zymo Research) according to the manufacturer's instructions. Gene regulatory regions for Bdnf exons IV and VI were PCR amplified using ZymoTaq™ DNA Polymerase (Zymo Research) from the bisulfite-converted DNA templates. The PCR fragments were subcloned into the pCR2.1-TOPO vector using TOPO TA cloning kit (Life Technologies) and sequenced with M13 primer (Genewiz). The primers used for PCR amplification of the bisulfite-converted genomic DNA are listed in Table 2 (SEQ ID NOs: 47-50).

Methylated DNA Immunoprecipitation (MeDIP)

Genomic DNA was isolated from primary cortical neurons using QIAamp DNA Mini Kit (QIAGEN) and fragmented by sonication using Bioruptor (Diagenode). 5-mC-containing DNA fragments were enriched from one μg of the sonicated genomic DNA by immunoprecipitation (IP) with mouse monoclonal anti-5mC antibody (Eurogentec, # BI-MECY-0100) as described previously[88]. IP and 10% input DNA samples were purified using MinElute PCR Purification Kit (QIAGEN) and subjected to qPCR with Bdnf promoter IV and Gapdh primers to measure the enrichment of the DNA fragment containing the Bdnf promoter IV region. Primer sequences are provided in Table 2 (SEQ ID NOs: 51-54). The percentage input was calculated by first normalizing IP to input DNA using the formula $(2^{[(Ct(10\% \; input)-3.32)-Ct(IP)]} \times 100)$ as described previously[89]. Gapdh was used as an internal normalization control.

Chromatin Immunoprecipitation (ChIP)

ChIP assays from mouse primary neurons were performed using Magna ChIP kit (Millipore) and anti-H3K4me3 antibody (Millipore, 17-614). The percentage input was calculated as $2^{[(Ct(10\% \; input)-3.32)-Ct(IP)]} \times 100$ and compared between WT and mutant Htt-expressing neurons. Sequences of the primers used to amplify the BDNF promoter IV fragment are listed in Table 2 (SEQ ID NOs: 55-56).

Statistical Analysis

Statistical differences were tested using XLSTAT and GraphPad Prism 6.0. Two-tailed unpaired Student t test for two group comparisons or one-way ANOVA with post-hoc tests, the Fisher's least significant difference (LSD) for comparison among three groups or the Bonferroni analysis for comparison among three or more than three groups. The Mann-Whitney U test was used for nonparametric test for comparing two groups. The data presented are from at least three independent experiments.

REFERENCES FOR EXAMPLES

1. Walker, F. O. Huntington's disease. *Lancet* 369, 218-228 (2007).
2. Ross, C. A. et al. Huntington disease: natural history, biomarkers and prospects for therapeutics. *Nature reviews. Neurology* 10, 204-216 (2014).
3. The Huntington's Disease Collaborative Research Group. A novel gene containing a trinucleotide repeat that is expanded and unstable on Huntington's disease chromosomes. *Cell* 72, 971-983 (1993).
4. Sugars, K. L. & Rubinsztein, D. C. Transcriptional abnormalities in Huntington disease. *Trends Genet* 19, 233-238 (2003).
5. Cha, J. H. Transcriptional signatures in Huntington's disease. *Prog Neurobiol* 83, 228-248 (2007).
6. Seredenina, T. & Luthi-Carter, R. What have we learned from gene expression profiles in Huntington's disease? *Neurobiol Dis* 45, 83-98 (2012).
7. Luthi-Carter, R. et al. Decreased expression of striatal signaling genes in a mouse model of Huntington's disease. *Hum Mol Genet* 9, 1259-1271 (2000).
8. Hodges, A. et al. Regional and cellular gene expression changes in human Huntington's disease brain. *Hum Mol Genet* 15, 965-977 (2006).
9. Weeks, R. A., Piccini, P., Harding, A. E. & Brooks, D. J. Striatal D1 and D2 dopamine receptor loss in asymptomatic mutation carriers of Huntington's disease. *Ann Neurol* 40, 49-54 (1996).
10. Pavese, N. et al. Progressive striatal and cortical dopamine receptor dysfunction in Huntington's disease: a PET study. *Brain: a journal of neurology* 126, 1127-1135 (2003).
11. Luthi-Carter, R. et al. Dysregulation of gene expression in the R6/2 model of polyglutamine disease: parallel changes in muscle and brain. *Hum Mol Genet* 11, 1911-1926 (2002).
12. Vashishtha, M. et al. Targeting H3K4 trimethylation in Huntington disease. *Proc Natl Acad Sci USA* 110, E3027-3036 (2013).
13. Greenberg, M. E., Xu, B., Lu, B. & Hempstead, B. L. New insights in the biology of BDNF synthesis and release: implications in CNS function. *J Neurosci* 29, 12764-12767 (2009).
14. Zuccato, C. & Cattaneo, E. Role of brain-derived neurotrophic factor in Huntington's disease. *Prog Neurobiol* 81, 294-330 (2007).
15. Zuccato, C. et al. Loss of huntingtin-mediated BDNF gene transcription in Huntington's disease. *Science* 293, 493-498 (2001).
16. Strand, A. D. et al. Expression profiling of Huntington's disease models suggests that brain-derived neurotrophic factor depletion plays a major role in striatal degeneration. *J Neurosci* 27, 11758-11768 (2007).
17. Xie, Y., Hayden, M. R. & Xu, B. BDNF overexpression in the forebrain rescues Huntington's disease phenotypes in YAC128 mice. *J Neurosci* 30, 14708-14718 (2010).
18. Sadri-Vakili, G. & Cha, J. H. Mechanisms of disease: Histone modifications in Huntington's disease. *Nat Clin Pract Neurol* 2, 330-338 (2006).
19. Lardenoije, R. et al. The epigenetics of aging and neurodegeneration. *Prog Neurobiol* 131, 21-64 (2015).
20. Bird, A. DNA methylation patterns and epigenetic memory. *Genes Dev* 16, 6-21 (2002).
21. McFarland, K. N. et al. Genome-wide histone acetylation is altered in a transgenic mouse model of Huntington's disease. *PLoS One* 7, e41423 (2012).
22. Ng, C. W. et al. Extensive changes in DNA methylation are associated with expression of mutant huntingtin. *Proc Natl Acad Sci USA* 110, 2354-2359 (2013).

23. Valor, L. M., Guiretti, D., Lopez-Atalaya, J. P. & Barco, A. Genomic landscape of transcriptional and epigenetic dysregulation in early onset polyglutamine disease. *J Neurosci* 33, 10471-10482 (2013).
24. McFarland, K. N. et al. Genome-wide increase in histone H2A ubiquitylation in a mouse model of Huntington's disease. *Journal of Huntington's disease* 2, 263-277 (2013).
25. Mielcarek, M. et al. HDAC4 reduction: a novel therapeutic strategy to target cytoplasmic huntingtin and ameliorate neurodegeneration. *PLoS Biol* 11, e1001717 (2013).
26. Kelly, T. K., De Carvalho, D. D. & Jones, P. A. Epigenetic modifications as therapeutic targets. *Nat Biotechnol* 28, 1069-1078 (2010).
27. Day, J. J. & Sweatt, J. D. DNA methylation and memory formation. *Nat Neurosci* 13, 1319-1323 (2010).
28. Day, J. J. et al. DNA methylation regulates associative reward learning. *Nat Neurosci* 16, 1445-1452 (2013).
29. Tuesta, L. M. & Zhang, Y. Mechanisms of epigenetic memory and addiction. *The EMBO journal* 33, 1091-1103 (2014).
30. Moore, L. D., Le, T. & Fan, G. DNA methylation and its basic function. *Neuropsychopharmacology* 38, 23-38 (2013).
31. Heyward, F. D. & Sweatt, J. D. DNA Methylation in Memory Formation: Emerging Insights. *The Neuroscientist: a review journal bringing neurobiology, neurology and psychiatry* 21, 475-489 (2015).
32. Feng, J. et al. Dnmt1 and Dnmt3a maintain DNA methylation and regulate synaptic function in adult forebrain neurons. *Nat Neurosci* 13, 423-430 (2010).
33. Grayson, D. R. & Guidotti, A. The dynamics of DNA methylation in schizophrenia and related psychiatric disorders. *Neuropsychopharmacology* 38, 138-166 (2013).
34. Tognini, P. et al. Experience-dependent DNA methylation regulates plasticity in the developing visual cortex. *Nat Neurosci* 18, 956-958 (2015).
35. Inano, K. et al. Maintenance-type DNA methyltransferase is highly expressed in post-mitotic neurons and localized in the cytoplasmic compartment. *Journal of biochemistry* 128, 315-321 (2000).
36. Feng, J., Chang, H., Li, E. & Fan, G. Dynamic expression of de novo DNA methyltransferases Dnmt3a and Dnmt3b in the central nervous system. *Journal of neuroscience research* 79, 734-746 (2005).
37. Veldic, M. et al. DNA-methyltransferase 1 mRNA is selectively overexpressed in telencephalic GABAergic interneurons of schizophrenia brains. *Proc Natl Acad Sci USA* 101, 348-353 (2004).
38. Yano, H. et al. Inhibition of mitochondrial protein import by mutant huntingtin. *Nat Neurosci* 17, 822-831 (2014).
39. Li, H., Li, S. H., Johnston, H., Shelbourne, P. F. & Li, X. J. Amino-terminal fragments of mutant huntingtin show selective accumulation in striatal neurons and synaptic toxicity. *Nat Genet* 25, 385-389 (2000).
40. DiFiglia, M. et al. Aggregation of huntingtin in neuronal intranuclear inclusions and dystrophic neurites in brain. *Science* 277, 1990-1993 (1997).
41. Bates, G. Huntingtin aggregation and toxicity in Huntington's disease. *Lancet* 361, 1642-1644 (2003).
42. Lunkes, A. et al. Proteases acting on mutant huntingtin generate cleaved products that differentially build up cytoplasmic and nuclear inclusions. *Mol Cell* 10, 259-269 (2002).
43. Landles, C. et al. Proteolysis of mutant huntingtin produces an exon 1 fragment that accumulates as an aggregated protein in neuronal nuclei in Huntington disease. *J Biol Chem* 285, 8808-8823 (2010).
44. Sathasivam, K. et al. Aberrant splicing of HTT generates the pathogenic exon 1 protein in Huntington disease. *Proc Natl Acad Sci USA* 110, 2366-2370 (2013).
45. Quintas-Cardama, A., Santos, F. P. & Garcia-Manero, G. Therapy with azanucleosides for myelodysplastic syndromes. *Nature reviews. Clinical oncology* 7, 433-444 (2010).
46. Gnyszka, A., Jastrzebski, Z. & Flis, S. DNA methyltransferase inhibitors and their emerging role in epigenetic therapy of cancer. *Anticancer research* 33, 2989-2996 (2013).
47. Yoo, C. B. & Jones, P. A. Epigenetic therapy of cancer: past, present and future. *Nat Rev Drug Discov* 5, 37-50 (2006).
48. Lu, H., Liu, X., Deng, Y. & Qing, H. DNA methylation, a hand behind neurodegenerative diseases. *Front Aging Neurosci* 5, 85 (2013).
49. Pruunsild, P., Kazantseva, A., Aid, T., Palm, K. & Timmusk, T. Dissecting the human BDNF locus: bidirectional transcription, complex splicing, and multiple promoters. *Genomics* 90, 397-406 (2007).
50. Aid, T., Kazantseva, A., Piirsoo, M., Palm, K. & Timmusk, T. Mouse and rat BDNF gene structure and expression revisited. *Journal of neuroscience research* 85, 525-535 (2007).
51. Gambazzi, L. et al. Diminished activity-dependent brain-derived neurotrophic factor expression underlies cortical neuron microcircuit hypoconnectivity resulting from exposure to mutant huntingtin fragments. *J Pharmacol Exp Ther* 335, 13-22 (2010).
52. Zuccato, C. et al. Systematic assessment of BDNF and its receptor levels in human cortices affected by Huntington's disease. *Brain Pathol* 18, 225-238 (2008).
53. Gray, M. et al. Full-length human mutant huntingtin with a stable polyglutamine repeat can elicit progressive and selective neuropathogenesis in BACHD mice. *J Neurosci* 28, 6182-6195 (2008).
54. Tao, X., West, A. E., Chen, W. G., Corfas, G. & Greenberg, M. E. A calcium-responsive transcription factor, CaRF, that regulates neuronal activity-dependent expression of BDNF. *Neuron* 33, 383-395 (2002).
55. Chen, W. G. et al. Derepression of BDNF transcription involves calcium-dependent phosphorylation of MeCP2. *Science* 302, 885-889 (2003).
56. Martinowich, K. et al. DNA methylation-related chromatin remodeling in activity-dependent BDNF gene regulation. *Science* 302, 890-893 (2003).
57. Rose, N. R. & Klose, R. J. Understanding the relationship between DNA methylation and histone lysine methylation. *Biochim Biophys Acta* 1839, 1362-1372 (2014).
58. Thomas, E. A. Striatal specificity of gene expression dysregulation in Huntington's disease. *Journal of neuroscience research* 84, 1151-1164 (2006).
59. Cha, J. H. et al. Altered brain neurotransmitter receptors in transgenic mice expressing a portion of an abnormal human huntington disease gene. *Proc Natl Acad Sci USA* 95, 6480-6485 (1998).
60. Mangiarini, L. et al. Exon 1 of the HD gene with an expanded CAG repeat is sufficient to cause a progressive neurological phenotype in transgenic mice. *Cell* 87, 493-506 (1996).
61. Crook, Z. R. & Housman, D. Huntington's disease: can mice lead the way to treatment? *Neuron* 69, 423-435 (2011).

62. Karahoca, M. & Momparler, R. L. Pharmacokinetic and pharmacodynamic analysis of 5-aza-2'-deoxycytidine (decitabine) in the design of its dose-schedule for cancer therapy. *Clin Epigenetics* 5, 3 (2013).
63. Chabot, G. G., Rivard, G. E. & Momparler, R. L. Plasma and cerebrospinal fluid pharmacokinetics of 5-Aza-2'-deoxycytidine in rabbits and dogs. *Cancer Res* 43, 592-597 (1983).
64. Rogstad, D. K. et al. Chemical decomposition of 5-aza-2'-deoxycytidine (Decitabine): kinetic analyses and identification of products by NMR, HPLC, and mass spectrometry. *Chem Res Toxicol* 22, 1194-1204 (2009).
65. Stresemann, C. & Lyko, F. Modes of action of the DNA methyltransferase inhibitors azacytidine and decitabine. *Int J Cancer* 123, 8-13 (2008).
66. Wang, F., Fischhaber, P. L., Guo, C. & Tang, T. S. Epigenetic modifications as novel therapeutic targets for Huntington's disease. *Epigenomics* 6, 287-297 (2014).
67. Valor, L. M. & Guiretti, D. What's wrong with epigenetics in Huntington's disease? *Neuropharmacology* 80, 103-114 (2014).
68. Sadri-Vakili, G. et al. Histones associated with down-regulated genes are hypo-acetylated in Huntington's disease models. *Hum Mol Genet* 16, 1293-1306 (2007).
69. Kim, M. O. et al. Altered histone monoubiquitylation mediated by mutant huntingtin induces transcriptional dysregulation. *J Neurosci* 28, 3947-3957 (2008).
70. Ryu, H. et al. ESET/SETDB1 gene expression and histone H3 (K9) trimethylation in Huntington's disease. *Proc Natl Acad Sci USA* 103, 19176-19181 (2006).
71. Wang, F. et al. Genome-wide loss of 5-hmC is a novel epigenetic feature of Huntington's disease. *Hum Mol Genet* 22, 3641-3653 (2013).
72. Cedar, H. & Bergman, Y. Linking DNA methylation and histone modification: patterns and paradigms. *Nat Rev Genet* 10, 295-304 (2009).
73. Kriaucionis, S. & Heintz, N. The nuclear DNA base 5-hydroxymethylcytosine is present in Purkinje neurons and the brain. *Science* 324, 929-930 (2009).
74. Tahiliani, M. et al. Conversion of 5-methylcytosine to 5-hydroxymethylcytosine in mammalian DNA by MLL partner TET1. *Science* 324, 930-935 (2009).
75. Wu, H. & Zhong, Y. Mechanisms and functions of Tet protein-mediated 5-methylcytosine oxidation. *Genes Dev* 25, 2436-2452 (2011).
76. Kaas, G. A. et al. TET1 controls CNS 5-methylcytosine hydroxylation, active DNA demethylation, gene transcription, and memory formation. *Neuron* 79, 1086-1093 (2013).
77. Guo, J. U., Su, Y., Zhong, C., Ming, G. L. & Song, H. Hydroxylation of 5-methylcytosine by TET1 promotes active DNA demethylation in the adult brain. *Cell* 145, 423-434 (2011).
78. Canals, J. M. et al. Brain-derived neurotrophic factor regulates the onset and severity of motor dysfunction associated with enkephalinergic neuronal degeneration in Huntington's disease. *J Neurosci* 24, 7727-7739 (2004).
79. Baydyuk, M. & Xu, B. BDNF signaling and survival of striatal neurons. *Frontiers in cellular neuroscience* 8, 254 (2014).
80. Zuccato, C., Valenza, M. & Cattaneo, E. Molecular mechanisms and potential therapeutical targets in Huntington's disease. *Physiol Rev* 90, 905-981 (2010).
81. Wild, E. J. & Tabrizi, S. J. Targets for future clinical trials in Huntington's disease: what's in the pipeline? *Movement disorders: official journal of the Movement Disorder Society* 29, 1434-1445 (2014).
82. Jiang, M. et al. Small-molecule TrkB receptor agonists improve motor function and extend survival in a mouse model of Huntington's disease. *Hum Mol Genet* 22, 2462-2470 (2013).
83. Simmons, D. A. et al. A small molecule TrkB ligand reduces motor impairment and neuropathology in R6/2 and BACHD mouse models of Huntington's disease. *J Neurosci* 33, 18712-18727 (2013).
84. Creusot, F., Acs, G. & Christman, J. K. Inhibition of DNA methyltransferase and induction of Friend erythroleukemia cell differentiation by 5-azacytidine and 5-aza-2'-deoxycytidine. *J Biol Chem* 257, 2041-2048 (1982).
85. Li, S. H. et al. Interaction of Huntington disease protein with transcriptional activator Sp1. *Molecular and cellular biology* 22, 1277-1287 (2002).
86. Mao, D. D. et al. A CDC20-APC/SOX2 Signaling Axis Regulates Human Glioblastoma Stem-like Cells. *Cell reports* 11, 1809-1821 (2015).
87. Menalled, L. et al. Systematic behavioral evaluation of Huntington's disease transgenic and knock-in mouse models. *Neurobiol Dis* 35, 319-336 (2009).
88. Li, D., Zhang, B., Xing, X. & Wang, T. Combining MeDIP-seq and MRE-seq to investigate genome-wide CpG methylation. *Methods* 72, 29-40 (2015).
89. Taiwo, O. et al. Methylome analysis using MeDIP-seq with low DNA concentrations. *Nat Protoc* 7, 617-636 (2012).

What is claimed is:

1. A method to reduce symptoms associated with Huntington's disease in a subject in need thereof, the method comprising administering to the subject a DNA methylation inhibitor, wherein the DNA methylation inhibitor is a nucleoside analog DNA methyltransferase (DNMT) inhibitor, and wherein the DNMT inhibitor decreases the levels of mutant Htt aggregates.

2. The method of claim 1, wherein the DNMT inhibitor is decitabine or FdCyd.

3. The method of claim 1, wherein the DNA methylation inhibitor is administered by the intracerebroventricular (icy) route.

4. The method of claim 1, wherein the DNA methylation inhibitor is administered intravenously, intramuscularly, or subcutaneously.

5. A method to reduce mutant huntingtin protein (Htt)-induced neurotoxicity, the method comprising contacting a nucleoside analog DNA methyltransferase (DNMT) inhibitor to neurons.

6. The method of claim 5, wherein the DNMT inhibitor is decitabine or FdCyd.

7. The method of claim 5, wherein the neurons are in vivo.

8. A method of preventing the development of the symptoms associated with Huntington's disease in a subject at risk of developing Huntington's disease, the method comprising administering to the subject a DNA methylation inhibitor; wherein the DNA methylation inhibitor is a nucleoside analog DNA methyltransferase (DNMT) inhibitor, and the DNMT inhibitor decreases the levels of mutant Htt aggregates.

9. The method of claim 8, wherein the DNMT inhibitor is decitabine or FdCyd.

10. The method of claim 8, wherein the DNA methylation inhibitor is administered by the intracerebroventricular (icy) route.

11. The method of claim 8, wherein the DNA methylation inhibitor is administered intravenously, intramuscularly, or subcutaneously.

* * * * *

SEQUENCE LISTING

<160> NUMBER OF SEQ ID NOS: 56

<210> SEQ ID NO 1
<211> LENGTH: 58
<212> TYPE: DNA
<213> ORGANISM: Artificial Sequence
<220> FEATURE:
<223> OTHER INFORMATION: SYNTHESIZED

<400> SEQUENCE: 1
ccggccagat gttctttgcc aataactcga gttattggca aagaacatct ggtttttg        58

<210> SEQ ID NO 2
<211> LENGTH: 58
<212> TYPE: DNA
<213> ORGANISM: Artificial Sequence

```
<220> FEATURE:
<223> OTHER INFORMATION: SYNTHESIZED

<400> SEQUENCE: 2
ccgggcagac caacatcgaa tccatctcga gatggattcg atgttggtct gcttttttg      58

<210> SEQ ID NO 3
<211> LENGTH: 62
<212> TYPE: DNA
<213> ORGANISM: Artificial Sequence
<220> FEATURE:
<223> OTHER INFORMATION: SYNTHESIZED

<400> SEQUENCE: 3
gtaccggatc tatggaaggt ggtattaact cgagttaata ccaccttcca tagattttt     60 tg                                                                    62

<210> SEQ ID NO 4
<211> LENGTH: 58
<212> TYPE: DNA
<213> ORGANISM: Artificial Sequence
<220> FEATURE:
<223> OTHER INFORMATION: SYNTHESIZED

<400> SEQUENCE: 4
ccggtatatg aagacctgat caatactcga gtattgatca ggtcttcata tattttttg     58

<210> SEQ ID NO 5
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 5
cggctgaggc agcagcggct gt                                              22

<210> SEQ ID NO 6
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 6
gcagcagcag cagcaacagc cgccaccgcc                                      30

<210> SEQ ID NO 7
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 7
atgaaggcct tcgagtccct caagtccttc                                      30

<210> SEQ ID NO 8
<211> LENGTH: 21
<212> TYPE: DNA
<213> ORGANISM: Artificial Sequence
<220> FEATURE:
<223> OTHER INFORMATION: SYNTHESIZED
```

-continued

<400> SEQUENCE: 8
ggcggctgag gaagctgagg a                                              21

<210> SEQ ID NO 9
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 9
aatagagacc ctcggaggca                                                20

<210> SEQ ID NO 10
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 10
cctgctgcta gttgggttct                                                20

<210> SEQ ID NO 11
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 11
aacagctcca gcccgagt                                                  18

<210> SEQ ID NO 12
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 12
ttttctgtta agccatctct ttcc                                           24

<210> SEQ ID NO 13
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 13
gacaaggcaa cttggcctac                                                20

<210> SEQ ID NO 14
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 14
cgtgctcaaa agtgtcagcc                                                20

```
<210> SEQ ID NO 15
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 15
cctgcatctg ttggggagac                                               20

<210> SEQ ID NO 16
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 16
gccttgtccg tggacgttta                                               20

<210> SEQ ID NO 17
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 17
ctagccaccg gggtggtgta a                                             21

<210> SEQ ID NO 18
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 18
cgccttcatg caaccgaagt                                               20

<210> SEQ ID NO 19
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 19
gcttcattga gcccagttcc                                               20

<210> SEQ ID NO 20
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 20
gccttgtccg tggacgttta                                               20

<210> SEQ ID NO 21
<211> LENGTH: 21
<212> TYPE: DNA
<213> ORGANISM: Artificial Sequence
<220> FEATURE:
<223> OTHER INFORMATION: SYNTHESIZED
```

```
<400> SEQUENCE: 21
cagagcagct gccttgatgt t                                      21

<210> SEQ ID NO 22
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 22
gccttgtccg tggacgttta                                        20

<210> SEQ ID NO 23
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 23
ttggggcaga cgagaaagcg c                                      21

<210> SEQ ID NO 24
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 24
aggatggtca tcactcttct c                                      21

<210> SEQ ID NO 25
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 25
agtcggcatc gtttatggtc                                        20

<210> SEQ ID NO 26
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 26
cgaaagcatt tgccaagaat                                        20

<210> SEQ ID NO 27
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 27
ttgacactgg taaaacaatg caaac                                  25
```

```
<210> SEQ ID NO 28
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 28
gagaggtcct tttcaccagc a                                               21

<210> SEQ ID NO 29
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 29
agtgtgacgt tgacatccgt a                                               21

<210> SEQ ID NO 30
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 30
gccagagcag taatctcctt ct                                              22

<210> SEQ ID NO 31
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 31
ctggagccaa aagcagtctg                                                 20

<210> SEQ ID NO 32
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 32
tccttcaggt ttccgacgcc                                                 20

<210> SEQ ID NO 33
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 33
ccaacccctg ccatgcttt                                                  19

<210> SEQ ID NO 34
<211> LENGTH: 21
<212> TYPE: DNA
<213> ORGANISM: Artificial Sequence
<220> FEATURE:
<223> OTHER INFORMATION: SYNTHESIZED
```

<400> SEQUENCE: 34
ttgggtctct tcgactttgg g                                              21

<210> SEQ ID NO 35
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 35
tggcgtaggg cctgcgtc                                                  18

<210> SEQ ID NO 36
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 36
tgtaaagcgg ccgcgtcg                                                  18

<210> SEQ ID NO 37
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 37
cgaccaacgg aaaagacaag                                                20

<210> SEQ ID NO 38
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 38
tgtctctggt gcatccatgt                                                20

<210> SEQ ID NO 39
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 39
aactgcgcct acttcgagg                                                 19

<210> SEQ ID NO 40
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 40
ggtgaaaagc atcgccgtac t                                              21

```
<210> SEQ ID NO 41
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 41
gctggacctc ggtgagaag                                               19

<210> SEQ ID NO 42
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 42
tcccaggagt agtctaggac g                                            21

<210> SEQ ID NO 43
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 43
gccatcccat tcgccatca                                               19

<210> SEQ ID NO 44
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 44
gcaatagcca agaggctgaa ga                                           22

<210> SEQ ID NO 45
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 45
tcaacctcct ccacaggcac                                              20

<210> SEQ ID NO 46
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 46
aggctcctca gccacagct                                               19

<210> SEQ ID NO 47
<211> LENGTH: 30
<212> TYPE: DNA
<213> ORGANISM: Artificial Sequence
<220> FEATURE:
<223> OTHER INFORMATION: SYNTHESIZED
```

<400> SEQUENCE: 47
gtgaatttgt taggattgga agtgaaaata					30

<210> SEQ ID NO 48
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 48
ctaaacaaaa actaaaaaat ttcatactaa ctc					33

<210> SEQ ID NO 49
<211> LENGTH: 29
<212> TYPE: DNA
<213> ORGANISM: Artificial Sequence
<220> FEATURE:
<223> OTHER INFORMATION: SYNTHESIZED

<400> SEQUENCE: 49
ggtaggtata gagttttggg tttaagtag					29

<210> SEQ ID NO 50
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 50
acactaaaat caaacattat ttaactcttc					30

<210> SEQ ID NO 51
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 51
gcgcggaatt ctgattctgg ta					22

<210> SEQ ID NO 52
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 52
ctgccttgac gtgagctgtc					20

<210> SEQ ID NO 53
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 53
ctctgctcct ccctgttcc					19

```
<210> SEQ ID NO 54
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 54
tccctagacc cgtacagtgc                                           20

<210> SEQ ID NO 55
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 55
cttctgtgtg cgtgaatttg ct                                        22

<210> SEQ ID NO 56
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 56
agtccacgag agggctcca                                            19
```